(12) United States Patent
Kido

(10) Patent No.: US 9,070,892 B2
(45) Date of Patent: Jun. 30, 2015

(54) ORGANIC ELECTROLUMINESCENT DEVICE

(71) Applicant: Junji Kido, Yamagata-Ken (JP)

(72) Inventor: Junji Kido, Yamagata-Ken (JP)

(73) Assignee: ROHM COMPANY, LTD. (JP)

( * ) Notice: Subject to any disclaimer, the term of this patent is extended or adjusted under 35 U.S.C. 154(b) by 0 days.

(21) Appl. No.: 13/892,868

(22) Filed: May 13, 2013

(65) Prior Publication Data
US 2014/0151648 A1    Jun. 5, 2014

Related U.S. Application Data

(60) Continuation of application No. 13/297,359, filed on Jan. 30, 2012, now Pat. No. 8,482,193, and a continuation of application No. 11/732,348, filed on Apr. 3, 2007, now Pat. No. 8,080,934, which is a division of application No. 10/393,952, filed on Mar. 21, 2003, now abandoned.

(30) Foreign Application Priority Data

Mar. 26, 2002 (JP) .................... 2002-86599
Mar. 14, 2003 (JP) .................... 2003-70135

(51) Int. Cl.
| | |
|---|---|
| H01L 51/50 | (2006.01) |
| C07C 211/58 | (2006.01) |
| C07C 211/61 | (2006.01) |
| C09K 11/06 | (2006.01) |
| H01L 51/52 | (2006.01) |
| H01L 51/56 | (2006.01) |

(52) U.S. Cl.
CPC ..... *H01L 51/5044* (2013.01); *Y10T 428/24942* (2015.01); *C07C 211/58* (2013.01); *C07C 211/61* (2013.01); *C07C 2103/18* (2013.01); *C09K 11/06* (2013.01); *C09K 2211/1003* (2013.01); *C09K 2211/1007* (2013.01); *C09K 2211/1011* (2013.01); *C09K 2211/1014* (2013.01); *H01L 51/5036* (2013.01); *H01L 51/5088* (2013.01); *H01L 51/5262* (2013.01); *H01L 51/5278* (2013.01); *H01L 51/56* (2013.01)

(58) Field of Classification Search
USPC .......... 313/498–512; 257/88, 89, 96, 98, 102, 257/103; 428/690, 917
See application file for complete search history.

(56) References Cited

U.S. PATENT DOCUMENTS 7,956,349 B2 * 6/2011 Tsutsui et al. .................. 257/40

* cited by examiner

*Primary Examiner* — Joseph L Williams
(74) *Attorney, Agent, or Firm* — Baker Hostetler LLP

(57) ABSTRACT

An organic electroluminescent device includes at least two light-emissive units provided between a cathode electrode and an anode electrode opposed to the cathode electrode, each of the light-emissive units including at least one light-emissive layer. The light-emissive units are partitioned from each other by at least one charge generation layer, the charge generation layer being an electrically insulating layer having a resistivity of not less than $1.0 \times 10^2$ $\Omega$cm.

20 Claims, 44 Drawing Sheets

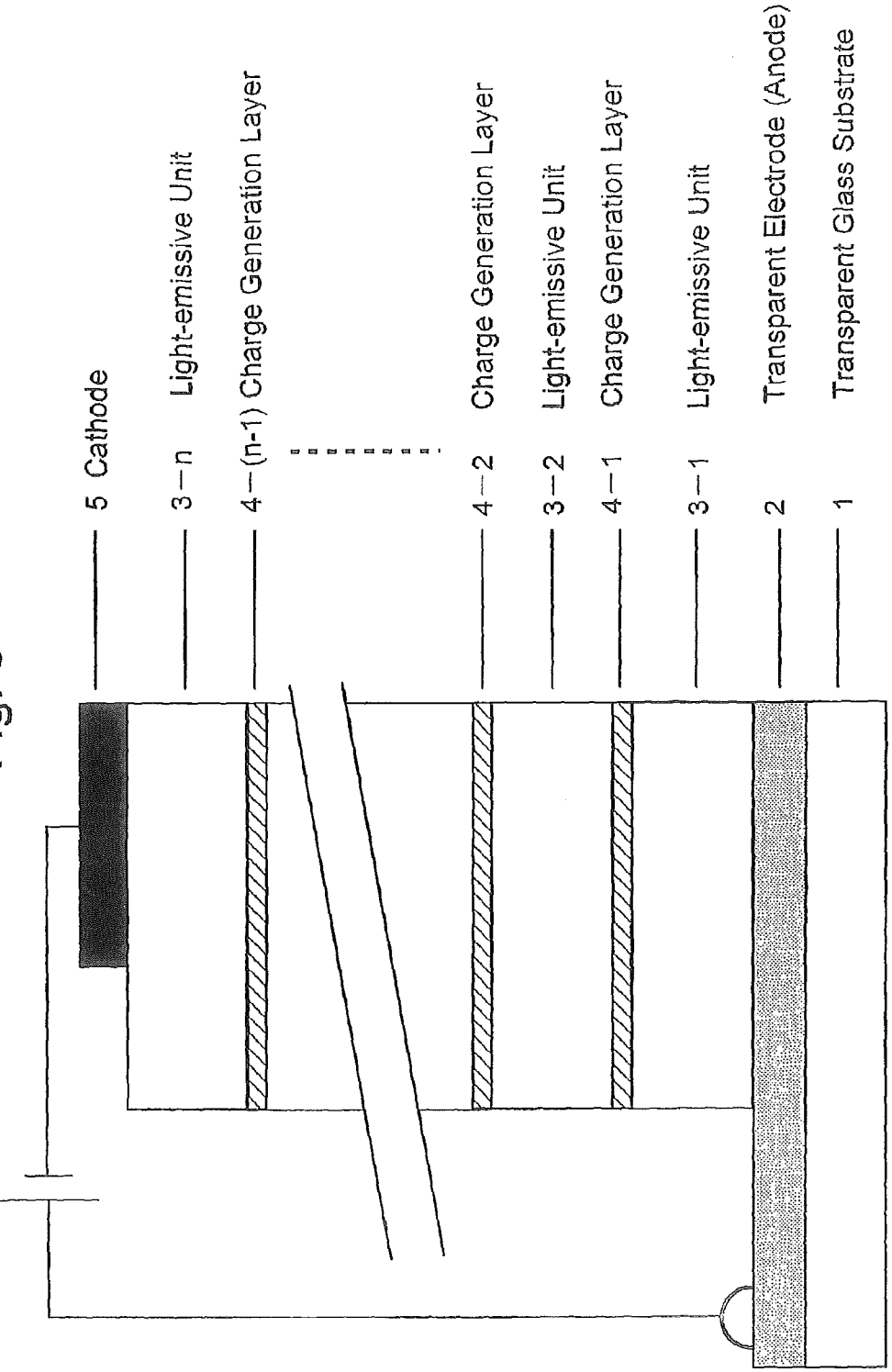

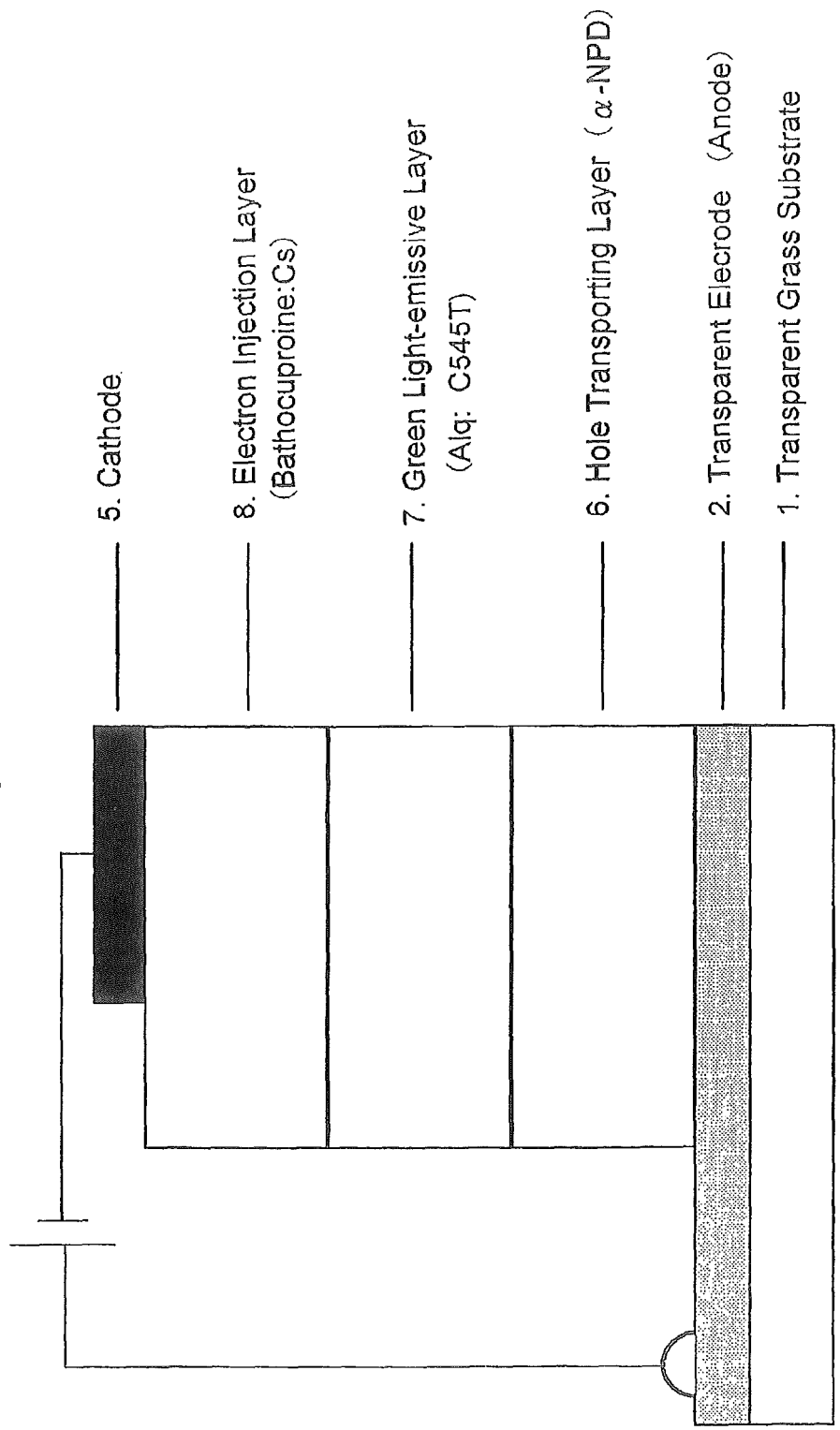

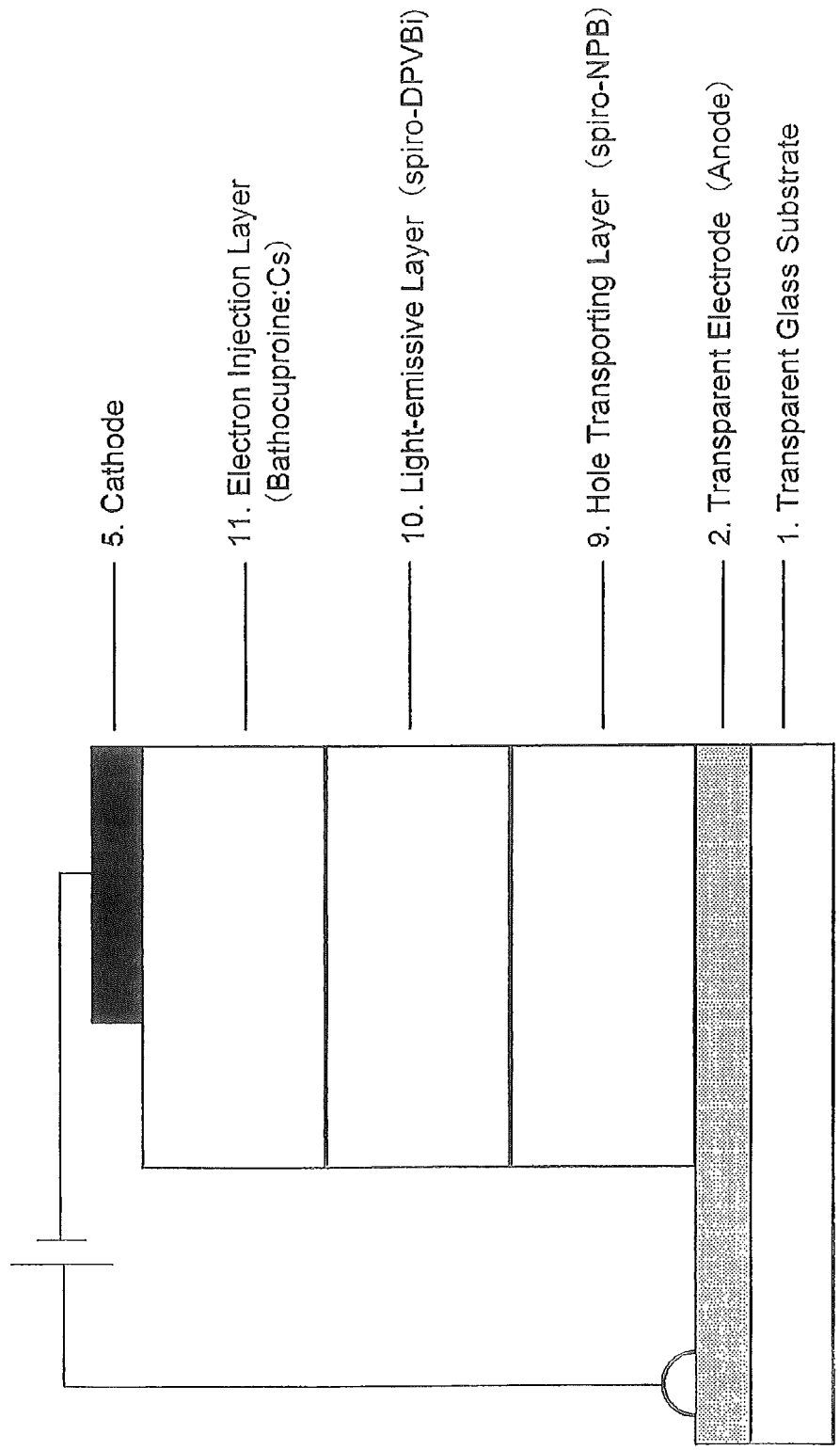

Fig. 27 ITO/α-NPD(70)/C545T doped Alq(60)/Cs doped Bathocuproine(10)/V2O5(30)
/α-NPD(x)/C545T doped Alq(60)/Cs doped Bathocuproine(10)/V2O5(30)
/α-NPD(x)/C545T doped Alq(60)/Cs doped Bathocuproine(10)/Al ○ x=70nm
□ x=50nm
+ x=30nm

ORGANIC ELECTROLUMINESCENT DEVICE

This application is a CON of Ser. No. 13/297,359 filed on Nov. 16, 2011 which is a continuation of U.S. Ser. No. 11/732,348 filed on Apr. 3, 2007, which, in turn is a DIV of Ser. No. 10/393,952 filed on Mar. 21, 2003, and claims priority from Foreign Applications JAPAN 2002-86599 dated Mar. 26, 2002 and JAPAN 2003-70135 dated Mar. 14, 2003, respectively.

BACKGROUND OF THE INVENTION

1. Field of the Invention

The present invention relates to an organic electroluminescent device (hereinafter, abbreviated as an "organic EL device" or "device") which can be used in planar light sources and display devices.

2. Description of the Related Art

Recently, attention has been drawn to organic electroluminescent devices having a light-emitting or luminescent layer including an organic compound between a cathode electrode and an anode electrode opposed to the cathode electrode as a large area display device operable at a low driving voltage. For the purpose of higher efficiency in an EL device, Tang et al., as is disclosed in Appl. Phys. Lett., 51, 913 (1987), have successfully achieved a sufficiently high luminance and high efficiency for practice use, i.e., a luminance of 1,000 $cd/m^2$ and an external quantum efficiency of 1% at an applied voltage no more(greater) than 10 volts, by adopting a structure in which organic compound layers having different carrier transporting properties are laminated to thereby introduce holes and electrons with good balance from an anode and a cathode, respectively, and by having the thickness of the organic compound layer no more(greater) than 2,000 Å.

Furthermore, according to the disclosures of the patents invented by Tang et al., (such as Japanese Laid-open Patent Application Nos. 59-194393, 63-264692 and 2-15595 and U.S. Pat. Nos. 4,539,507, 4,769,292 and 4,885,211) it is stated that if a total layer thickness of the organic layers sandwiched between an anode and a cathode does not exceed about 1 µm, an EL device capable of emitting light at a lower level of the applied voltage can be provided, and that desirably, if the total layer thickness is reduced to a range of 1,000 to 5,000 Å, an electric field (V/cm) useful in obtaining a light emission at an applied voltage no more than about 25 volts can be obtained.

The reason why Tang et al. have directed their attention to a reduction of the layer thickness of the organic layers in attaining a reduction of the driving voltage, as described in the above-referenced article, resides in overcoming the problem suggested by Helfrich et al. in the 1960s. Namely, Helfrich et al. have observed that an external quantum efficiency of about 5% can be obtained when a sufficient electric field electroluminescence (EL) is applied to an anthracene single crystal; however, according to their method, only a low power conversion efficiency (w/w) could be obtained, since the voltage required to drive such devices is quite high (greater than 100V).

Referring to the above-reference Tang et al. patents, the organic EL devices suggested therein have a multilayered structure in which an anode, a hole injection (transporting) layer, a light-emitting layer (having an electron transporting property) and a cathode are laminated in that order, and the devices can provide a quantum efficiency of at least about $5\times10^{-4}$ (0.05%). Furthermore, the quantum efficiency is defined in Japanese Laid-open Patent Application No. 59-194393 as the EL quantum efficiency simply equaling the ratio of photons per second emitted from the cell, to the electrons per second measured in the external circuit.

Presently, as has been already disclosed, when a fluorescent material (utilizing emission from a singlet excitation state) is used in the thin layer EL devices suggested by Tang et al., a quantum efficiency above 5% can be obtained. Furthermore, when a phosphorescent material (utilizing emission from a triplet excitation state) is used in the EL devices, a quantum efficiency approaching to 20% can be obtained.

As can be appreciated from the above description, the quantum efficiency is calculated from the number of the photons actually emitted from (outside of) the device, and thus the quantum efficiency is called external quantum efficiency. On the other hand, the number of photons generated internally in the device might be quite large when compared with the value observed externally, and it is predicted that such efficiency, called internal quantum efficiency might reach about 5 times of the external quantum efficiency. Accordingly, even presently, when using a phosphorescent material, an internal quantum efficiency can be exhibited at 100%, and thus it seems that the remaining problem in the organic EL devices resides only in an increase of the reliability concerning the operational life-time of the devices.

As described above, the suggestions by Tang et al. in their patents and articles have accelerated a worldwide research and development in the field of organic EL devices, and thus a great number of improved EL devices have been developed based on the basic device structure suggested by Tang et al. Presently, commercialization of the EL devices has already started in regard to their use as a display device on a dashboard or in a cellular phone.

However, from a viewpoint of durability of the device, the above-described conventional organic EL devices can barely attain a half-decay life time exceeding 10,000 hours with a luminance of only the order of 100 $cd/m^2$, which is required in display use. Presently, it is still difficult to attain a required practical operational life-time (10,000 hours or more) with a luminance of about 1,000 to 10,000 $cd/m^2$, which is required in illumination use, etc. In fact, an organic EL device having a high luminance and long operational life-time is still not realized and not commercially available.

As described above, attention that has recently been drawn to organic EL devices has been based on the discovery of a thin film-forming material which drives the resulting device at a low voltage of not more than 10 volts. However, the resulting device still suffers from the disadvantage that if the device is intended to obtain a high luminance emission necessary for illumination purposes, a higher current density approaching tens of $mA/cm^2$ to hundreds of $mA/cm^2$ is necessary. Note that in the best green light-emitting devices currently available, a luminance of about thousands to tens of thousands of $cd/m^2$ still needs the above-mentioned current density of about 10 to 100 $mA/cm^2$. It can be considered that this property is characteristic of charge injection type devices (like this organic EL device), and such characteristics can cause a relatively large problem with the operational life-time of organic EL devices in comparison with an inorganic LED (light-emitting diode) which is also a charge injection device and uses an inorganic compound semiconductor which can be more robust than organic compounds.

In an organic layer formed from a low molecular organic material via a vacuum vapor deposition method, the nature of the electric current passing through the organic layer is defined as a hopping conduction of electrons and holes between the molecules of the material. Furthermore, when observing the molecules from the chemical aspect, it can be described like this; the electron transporting molecules and the hole transporting molecules which are generally being as electrically neutral molecules are repeatedly subjected to a process in which the electron transporting and hole transporting molecules are shifted to a radical anion state or a radical cation state, i.e., the oxidation-reduction reaction in terms of Lewis' chemistry is being repeated between these molecules. Referring to the above-described property in the organic EL devices, i.e., that a higher current density is required to attain higher luminance, this property means that the oxidation-reduction reactions are repeated at a higher frequency. Obviously, the deterioration speed of the organic molecules is proportional to a frequency of the oxidation-reduction reactions, namely, the current density.

To solve the above problem, Japanese Laid-open Patent Application No. 11-329748 (corresponding U.S. Pat. No. 6,107,734) suggests an organic EL device in which a plurality of organic light-emitting layers are electrically connected in series through an intermediate conductive layer, and with regard to the intermediate conductive layer, describes that many types of materials may be used in the formation of the intermediate conductive layer, as long as they (the intermediate conductive layer) are capable of injecting holes and electrons to one or the other primary surface side, and capable of keeping an approximate equipotential in the layer.

This EL device, however, suffers from the following problem. For instance, in the display device having a simple matrix structure, the light emission area upon voltage application should be defined only to the pixel, i.e., the intersection area, sandwiched by cathode and anode line, thereby enabling to display a motion picture. However, in the above-described case in which the intermediate conductive layer having a substantially equipotential surface is formed in a substantially overall surface in an area which is equal to the area of the organic light-emitting layers, i.e., when the intermediate conductive layer is also formed in areas other than the intersection area sandwiched by cathode and anode line, light emission can be generated in areas other than the intersection areas in which the light emission is desired to be generated. Specifically, there is a possibility of generating light emission in all of the crossed area of the cathode with the intermediate conductive layer, the crossed area of the anode and with the intermediate conductive layer, and if two or more intermediate conductive layers are contained, the crossed area between one intermediate conductive layer and another intermediate conductive layer.

Accordingly, it is described in Japanese Laid-open Patent Application No. 11-329748 that the intermediate conductive layers of each pixel are separated not only from the intermediate conductive layer of the adjacent pixels, but also from a power source. Furthermore, one idea to separate the intermediate conductive layers from each other in the pixels in the EL device having a simple matrix structure is also described in this publication. If an interlayer insulation film is previously formed and disposed at a layer thickness above 1 μm and in the form of a sharp step pattern, the conductive layer can be automatically separated in the presence of a suddenly-changed shape of the interlayer insulation film, even if the conductive layer is formed using the shadow mask identical to the one for an organic material deposition.

However, in this case, although the cathode should not be separated, the cathode can be separated by the interlayer insulation film if the cathode has only a thickness of about 0.1 μm (100 nm) as in the conventional organic EL devices. To avoid this problem, Japanese Laid-open Patent Application No. 11-329748 teaches use of In (indium) as the cathode material at large thickness, thereby preventing electrical separation of the cathode line, because indium cannot easily cause problems due to crystallization (this problem is generally referred to as "hillock"), even if the cathode is formed at a thickness of 1 μm or more.

In this alternative case, however, a problem of the throughput reduction cannot be also avoided, because a metal such as Al (aluminum), which is a conventional and low-cost wiring material, cannot be used as a cathode material and also it is necessary to stably form "an interlayer insulation film having a layer thickness above 1 μm and a suddenly-changed shape of the interlayer".

Furthermore, the inventors of the present invention have also proposed another organic EL device in Japanese Patent Application No. 2001-225847, and has at least two light-emitting units constituting the conventional organic EL device (the components in all the elements constituting the conventional organic EL device except for a cathode and an anode), and the contained light-emitting units are separated from each other with a transparent layer acting as an equipotential surface.

The "equipotential surface" used herein means that when a voltage is applied, the transparent layer cannot exhibit a substantial potential difference in both a thickness direction and a planar (lateral) direction in the layer. In other words, although the inventors have not specifically disclosed, they have implied the necessity to construct the equipotential surface from an electrically conductive material, i.e., any material having a resistivity less than $1.0 \times 10^2$ Ωcm.

However, as in the above-discussed Japanese Laid-open Patent Application No. 11-329748, if the two or more light-emitting units are separated using a material having a high electrical conductivity (low resistivity) described above, there may be difficulties in defining light emission areas as required, due to the conductivity in a planar (lateral) direction (direction parallel to a substrate).

In practice, as shown in FIG. 38B, even if the production of the EL device is carried out in accordance with the method of Japanese Laid-open Patent Application No. 11-329748 by producing a cathode 55 and an anode 52, both in the form of a strip having a width of 2 mm, and arranging the cathode 55 and the anode 52 so that they are crossed at right angles, thereby producing a light emission area corresponding to the crossed (intersection) area, i.e., 2 mm square (☐), unexpected light emission may be caused in other areas when there is an area having an equipotential surface 54 is extended to another area. The undesirable emission in the EL device is shown in the photograph of FIG. 38A.

To avoid the above problem, as disclosed in the examples of Japanese Patent Application No. 2001-225847, the inventors had to form an equipotential surface using a shadow mask (2 mm square pattern; ☐) having a patterned opening which corresponds to the desired light emission area, thereby selectively forming the equipotential surface only in the desired emission layer. However, in this method, it is difficult to attain selective emission only in the desired pixels in the display device, because the display device has to be produced at a pixel length and pitch (between each pixel) of about 0.1 mm or less.

In regard to improving productivity in mass-production of the EL devices, frequent changing and precise positioning operations of the shadow mask is not desirable, because it causes tremendous reduction of throughput.

SUMMARY OF THE INVENTION

In view of the above problems in the conventional organic electroluminescent (EL) devices, the present invention provides an organic EL device which can effectively and stably provide a device structure capable of achieving a long operational life time with a light-emission at a higher luminance, which cannot be easily attained in conventional EL devices. In the production of such organic electroluminescent (EL) devices, the formation of two or more light-emissive units (mainly formed from an organic material), sandwiched between a cathode and an anode, frequent change and precise positioning of shadow masks for defining a deposition area is not required during the formation of a charge generation layer, which is newly introduced in the present invention. A formation of the interlayer insulation film in a sudden-changed shape which has a risk of causing disconnection of a cathode line is also not required, thus enabling to enhance productivity and to simplify the process of manufacturing simple matrix-type display devices, etc. According to an aspect of the present invention, an organic electroluminescent device is provided, including at least two light-emissive units provided between a cathode electrode and an anode electrode opposed to the cathode electrode, each of the light-emissive units including at least one light-emissive layer. The light-emissive units are partitioned from each other by at least one charge generation layer, the charge generation layer constituting an electrically insulating layer having a resistivity of not less than $1.0 \times 10^2$ Ωcm.

It is desirable for the charge generation layer to constitute an electrically insulating layer having a resistivity of not less than $1.0 \times 10^5$ Ωcm.

It is desirable for the charge generation layer to include a laminated and/or mixed layer formed from two different materials. A charge transfer complex including a radical cation and a radical anion is formed upon an oxidation-reduction reaction between the two materials, and a radical cation state and a radical anion state in the charge transfer complex is transferred to a direction of the cathode and a direction of the anode, respectively, when a voltage is applied to the device, so that a hole is injected into the light-emissive unit which is located on a cathode side of the charge generation layer and is adjacent thereto, and an electron is injected into the light-emissive unit which is located on an anode side of the charge generation layer and is adjacent thereto.

It is desirable for the charge generation layer to include a laminated and/or a mixed layer including an organic compound having an ionization potential of less than 5.7 eV and a hole transporting property or electron donating property; and an inorganic and/or organic material capable of forming a charge transfer complex through the oxidation-reduction reaction thereof with the organic compound. The charge generation layer contains a charge transfer complex formed upon the oxidation-reduction reaction between the organic compound and one of an inorganic and organic material.

The organic compound can include an arylamine compound, wherein the arylamine compound is represented by the following formula (I):

wherein Ar1, Ar2 and Ar3 each independently represents an aromatic hydrocarbon group which may have substituents.

It is desirable for the organic compound to include an arylamine compound having a glass transition temperature of not lower than 90° C.

The arylamine can include one of α-NPD, 2-TNATA, Spiro-TAD, and spiro-NPB.

The inorganic material can be a metal oxide.

The inorganic material can be a metal halide.

The metal oxide can be vanadium pentaoxide or rhenium heptaoxide.

The inorganic material can be deposited by one of a resistive heating vapor deposition method, an electron beam vapor deposition method and a laser beam vapor deposition method.

The inorganic material can be deposited by a sputtering method. A sputtering apparatus used in the sputtering method is a facing target sputtering system which includes a pair of opposed targets provided at a certain distance, a reflection electrode capable of reflecting electrons towards a front peripheral area of each target, and a magnetic field generation device capable of forming a parallel magnetic field in the vicinity of the peripheral portion of each target, the magnetic field having a portion parallel to the peripheral portion of the target.

The organic material can include at least one fluorine as a substituent group, and possess at least one of an electron injection property and an electron accepting property.

The organic material can include at least one cyano group as a substituent group, and possess at least one of an electron injection property and an electron accepting property.

The organic material can be tetrafluoro-tetracyanoquinodimethane (4F-TCNQ).

The light-emissive unit can include, as a layer located on an anode side of the charge generation layer and being adjacent thereto, an electron injection layer having a mixture including an organic compound and a metal functioning as an electron donating dopant.

The electron donating dopant can include at least one metal selected from a group including an alkaline metal, an alkaline earth metal and a rare earth metal.

The metal of the electron donating dopant can be provided in a molar ratio of 0.1 to 10 with respect to the organic compound in the electron injection layer.

The light-emissive unit can include, as a layer located on an anode side of the charge generation layer and being adjacent thereto, a metal layer having a thickness of not more than 5 nm formed from a metal selected from an alkaline metal, an alkaline earth metal and a rare earth metal. The metal constituting the layer diffuses in the adjacent electron transporting layer to react with electron transporting organic material. As a result of the diffusion, an electron injection layer being composed of a mixture including the electron transporting organic material and a metal functioning as an electron donating dopant is formed.

The light-emissive unit can include, as a layer located on an anode side of the charge generation layer and being adjacent thereto, a layer including an organic metal complex compound including at least one metal ion selected from an alkaline metal ion, an alkaline earth metal ion and a rare earth metal ion, and a reaction generating layer which is formed by an in-situ reduction reaction when a thermally reducible metal, which can reduce a metal ion in the organic metal complex to a metal in a vacuum is deposited on the organic metal complex constituting the layer.

The light-emissive unit can include, as a layer located on an anode side of the charge generation layer and being adjacent thereto, a layer including an inorganic compound including at least one metal ion selected from an alkaline metal ion, an alkaline earth metal ion and a rare earth metal ion, and a reaction generating layer which is formed by an in-situ reduction reaction when a thermally reducible metal, which can reduce a metal ion in the inorganic compound to a metal in a vacuum is deposited on the inorganic compound constituting the layer.

It is desirable for the thermally reducible metal to include at least one selected from Aluminum, Zirconium, Silicon, Titanium and Tungsten.

The light-emissive unit can include a structure, as a layer located on an anode side of the charge generation layer and being adjacent thereto, in which a layer of a mixture including an organic compound and an electron donating dopant is formed, thereafter, a reaction generating layer is generated by an in-situ reduction reaction when a thermally reducible metal, which can reduce an alkaline metal ion, an alkaline earth metal ion or a rare earth metal ion to a metal in a vacuum, is deposited on an organic metal complex compound containing at least one metal ion selected from an alkaline metal ion, an alkaline earth metal ion and a rare earth metal ion.

The light-emissive unit can include a structure, as a layer located on an anode side of the charge generation layer and being adjacent thereto, in which a layer of a mixture including an organic compound and an electron donating dopant is formed, a reaction generating layer is generated by an in-situ reduction reaction when a thermally reducible metal, which can reduce an alkaline metal ion, an alkaline earth metal ion or a rare earth metal ion to a metal in a vacuum, is deposited on an inorganic compound containing at least one metal ion selected from an alkaline metal ion, an alkaline earth metal ion and a rare earth metal ion.

The light-emissive unit can include, as a layer located on a cathode side of the charge generation layer and being adjacent thereto, a hole injection layer including a mixture of an organic compound and an electron accepting compound having a property capable of oxidizing the organic compound in terms of Lewis acid chemistry.

The electron accepting compound having a property capable of oxidizing the organic compound in the hole injection layer in terms of Lewis acid chemistry can be provided in a molar ratio of 0.01 to 10 with respect to the organic compound.

The light-emissive unit can include, as a layer located on a cathode side of the charge generation layer and being adjacent thereto, a hole injection layer including an electron accepting compound and having a thickness of not more than 30 nm.

The light-emissive units can each have different emission spectrums.

The organic electroluminescent device can emit white light due to superimposing of different lights from each light-emissive unit.

At least one of the light-emissive units can include a light-emissive layer containing a phosphorescent material.

In each of the light-emissive units, it is desirable for an optical path length from a light-emissive site to a light-reflective metal electrode to be an odd-numbered times a quarter wavelength of light.

All the layers including the light-emissive units, the charge generation layer and the electrode layer can be formed on a substrate by heating a vaporizable material in a vacuum to deposit one of a vaporized and sublimed material on the substrate. Upon depositing the vaporized or sublimed material on the substrate, a substrate is transported in a direction of a planar surface thereof, a deposition area being open in a lower surface of the substrate; a container is provided, in a lower position of the transporting substrate, including a vaporizable material having a deposition width which can cover the deposition area extending in a direction perpendicular to the transportation direction of the substrate; and the container is heated to thereby one of vaporize and sublime so as to deposit the vaporizable material provided in the container.

It is desirable for a combined thickness of the light-emissive units and the charge generation layers, sandwiched between the cathode and the anode, to be greater than 1,000 nm (1 μm).

It is desirable for the organic electroluminescent device to be operated at a driving voltage of more than 25 volts.

It is desirable for light to be able to be passed in only one direction which is one of an anode electrode direction and a cathode electrode direction, from a light generation site in the organic electroluminescent device, wherein light advancing in a direction opposite to the only one direction is absorbed by a light-absorbing medium, and wherein, in each of the light-emissive units, a light interference effect is removed so that an adjustment of an optical path length from a light-emissive site of the light-emissive-layers to a light-reflective metal electrode is substantially not necessary.

It is desirable for light advancing in one direction which is one of an anode electrode direction and a cathode electrode direction, from a light generation site in the organic electroluminescent device to be reflected diffusely by a diffused reflection medium, and in each of the light-emissive units, a light interference effect to be removed, so that an adjustment of an optical path length from a light-emissive site of the light-emissive layers to a light-reflective metal electrode is substantially not necessary.

The present disclosure relates to subject matter contained in Japanese Patent Application Nos. 2002-86599 (filed on Mar. 26, 2002) and 2003-70135 (filed on Mar. 14, 2003) which are expressly incorporated herein by reference in their entireties.

BRIEF DESCRIPTION OF THE DRAWINGS

FIG. 8 is a schematic cross-sectional view illustrating a lamination structure of the organic EL device according to the present invention;

FIG. 9 is a schematic cross-sectional view illustrating a lamination structure of the organic EL device produced in Reference Example 1;

FIG. 11 is a schematic cross-sectional view illustrating a lamination structure of the organic EL device produced in Reference Example 2;

DESCRIPTION OF THE PREFERRED EMBODIMENTS

Figure 1:
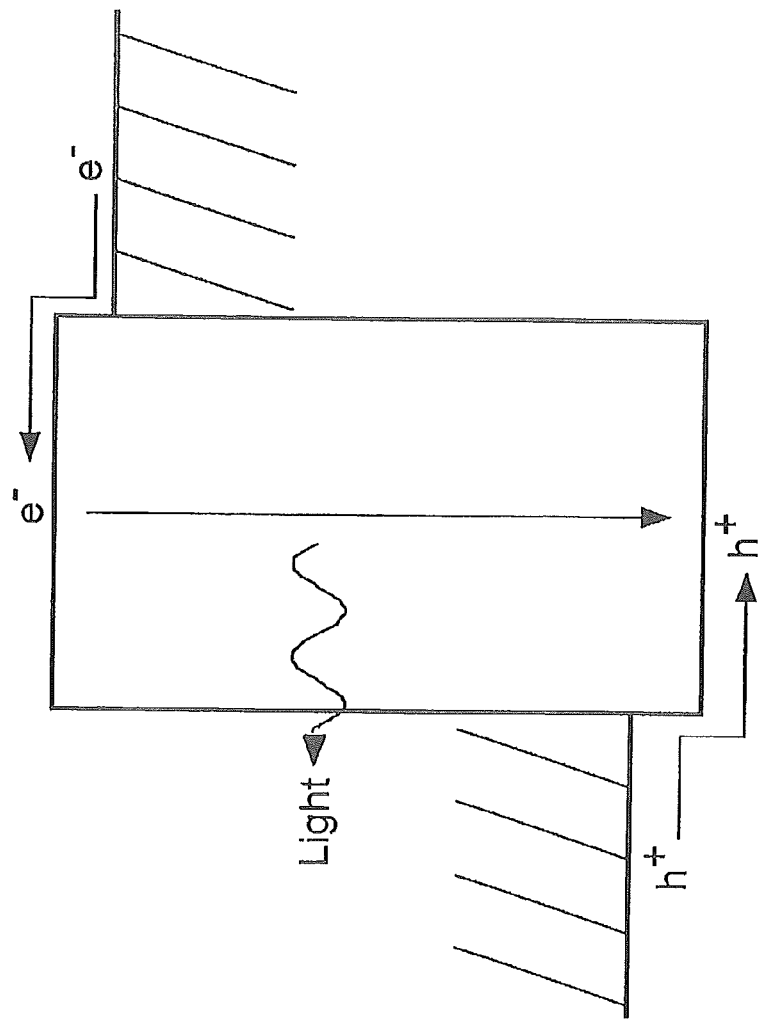
FIG. 1 is a schematic view showing a light emission mechanism of prior art organic EL device.

The inventors of the present invention have conducted intensive studies for solving the above-mentioned problems, and have found that a solution can be attained if two or more laminated light-emissive units are sandwiched between a cathode electrode and an anode electrode opposed to the cathode electrode, and each of the light-emissive units are partitioned with a charge generation layer having a resistivity of at least $1.0 \times 10^2$ Ωcm, desirably at least $1.0 \times 10^5$ Ωcm. Hereinafter, the property having such a resistivity is abbreviated as "electrically insulating".

When a certain level of the voltage was applied between a cathode and an anode in the EL device having the above structure, only the two or more light-emissive units located in a crossed area of the cathode and the anode can be connected as if connected in series, and thus they can simultaneously emit light. Because of this simultaneous emission, using the EL device, it becomes possible to achieve a high quantum efficiency or current efficiency which cannot be obtained in any conventional EL device.

As described above, according to the present invention, the light-emissive units are connected "as if connected in series" throughout the charge generation layer. Such a series connection of the light-emissive, units means that when a certain level of the voltage was applied to the EL device, each charge generation layer can inject holes in a cathode direction of the device, thus playing a role for injecting electrons in an anode direction, and as a result of injection of both the electrons and the holes, although all the layers (light-emissive units and the charge generation layers) sandwiched between the anode and the cathode are formed from an electrically insulating layer, the two or more light-emissive units can act just as they are electrically connected in series as in an electrical circuit.

In other words, the organic EL device according to the present invention resides in an organic EL device including two or more light-emissive units between a cathode electrode and an anode electrode opposed to the cathode electrode, each light-emissive unit having at least one light-emissive layer, in which the light-emissive units are partitioned from each other by at least one charge generation layer, and the charge generation layer is an electrically insulating layer having a resistivity of at least more than $1.0 \times 10^2$ Ωcm, desirably at least $1.0 \times 10^5$ Ωcm.

Furthermore, the material used in the formation of layers constituting each light-emissive unit corresponds to a component sandwiched between the anode and the cathode in the conventional EL devices, and thus all the layers formed therein are electrically insulating layers having a resistivity of not less than $1.0 \times 10^2$ Ωcm.

The "light-emissive unit" refers to a component of the EL device having a layer structure including at least one light-emissive layer including an organic compound, i.e., the component of the conventional organic EL device from which an anode and a cathode are omitted.

Furthermore, the "charge generation layer" refers to an electrically insulating layer having a resistivity of not less than $1.0 \times 10^2$ Ωcm, desirably at least $1.0 \times 10^5$ Ωcm, and as described above, represents a layer capable of injecting an electron for an anode direction of the device as well as injecting a hole for a cathode direction of the device upon voltage being applied.

In the organic EL device of the present invention, the charge generation layer desirably includes a laminate or a mixed layer formed from two different materials. A charge transfer complex having a radical cation and a radical anion is formed upon an oxidation-reduction reaction between these two materials. When a voltage is applied to the EL device, a radical cation state (hole) and a radical anion state (electron) in the charge transfer complex is transferred to a direction of the cathode and a direction of the anode, respectively, so that a hole is injected into the light-emissive unit which is located on a cathode side of the charge generation layer and is adjacent thereto, and an electron is injected into the light-emissive unit which is located on an anode side of the charge generation layer and is adjacent thereto.

Moreover, in the organic EL device of the present invention, the charge generation layer desirably includes a laminated or a mixed layer which has the following components:

(a) an organic compound having an ionization potential of less than 5.7 eV and a hole transporting property or electron donating property; and (b) an inorganic or organic material capable of forming a charge transfer complex through its oxidation-reduction reaction with the organic compound (a); and a charge transfer complex formed upon the oxidation-reduction reaction between the components (a) and (b) being contained in the charge generation layer.

In addition, in order to easily obtain a radical cation state from an organic compound which generally has an electron donating property, it is desirable that the organic compound has an ionization potential of less, than 5.7 eV. If the ionization potential of the organic compound used as the component (a) is 5.7 eV or more, it is difficult to cause an oxidation-reduction between the organic compound and the compound used as the component (b) with result of difficulty in producing a charge transfer complex which is required in when applying the present invention.

More particularly, the organic compound used as the component (a) is desirably an arylamine compound, and the arylamine compound is desirably represented by the following formula (I):

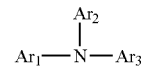

wherein Ar1, Ar2 and Ar3 each independently represent an aromatic hydrocarbon group which can hav$_e$ substituents.

tetra-p-tolyl-4,4'-diaminobiphenyl, bis(4-di-p-tolylaminophenyl)phenylmethane, N,N'-diphenyl-N,N'-di(4-methoxyphenyl)-4,4'-diaminobiphenyl, N,N,N',N'-tetraphenyl-4,4'-diaminodiphenylether, 4,4'-bis(diphenylamino)quadriphenyl, 4-N,N-diphenylamino-(2-diphenylvinyl)benzene, 3-methoxy-4'-N,N-diphenylaminostylbenzene, N-phenylcarbazole, 1,1-bis(4-di-p-triaminophenyl)cyclohexane, 1,1-bis(4-di-p-triaminophenyl)-4-phenylcyclohexane, bis(4-dimethylamino-2-methylphenyl)phenylmethane, N,N,N-tri(p-tolyl)amine, 4-(di-p-tolylamino)-4'-[4-(di-p-tolylamino)styryl]stilbene, N,N,N',N'-tetraphenyl-4,4'-diaminobiphenyl N-phenylcarbazole, 4,4'-bis[N-(1-naphthyl)-N-phenylamino]biphenyl, 4,4''-bis[N-(1-naphthyl)-N-phenylamino]p-terphenyl, 4,4'-bis[N-(3-acenaphthenyl)-N-phenylamino]biphenyl, 1,5-bis[N-(1-naphthyl)-N-phenylamino]naphthalene, 4,4'-bis[N-(9-anthryl)-N-phenylamino]biphenyl, 4,4''-bis[N-(1-anthryl)-N-phenylamino]p-terphenyl, 4,4'-bis[N-(2-phenanthryl)-N-phenylamino]biphenyl, 4,4'-bis[N-(8-fluoranthenyl)-N-phenylamino]biphenyl, 4,4'-bis[N-(2-pyrenyl)-N-phenylamino]biphenyl, 4,4'-bis[N-(2-perylenyl)-N-phenylamino]biphenyl, 4,4'-bis[N-(1-coronenyl)-N-phenylamino]biphenyl, 2,6-bis(di-p-tolylamino)naphthalene, 2,6-bis[di-(1-naphthyl)amino]naphthalene, 2,6-bis[N-(1-naphthyl)-N-(2-naphthyl)amino]naphthalene, 4,4''-bis[N,N-di(2-naphthyl)amino]terphenyl, 4,4'-bis(N-phenyl-N-[4-(1-naphthyl)phenyl]amino) biphenyl, 4,4'-bis[N-phenyl-N-(2-pyrenyl)amino]biphenyl, 2,6-bis[N,N-di(2-naphthyl)amino]fluorene, 4,4''-bis(N,N-di-p-tolylamino)terphenyl, bis(N-1-naphthyl)(N-2-naphthyl)amine, 4,4'-bis[N-(2-naphthyl)-N-phenylamino]biphenyl (α-NPD), represented by the following formula:

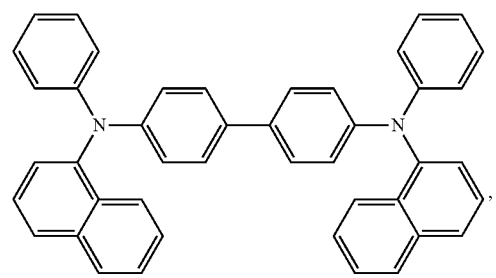

spiro-NPD represented by the following formula:

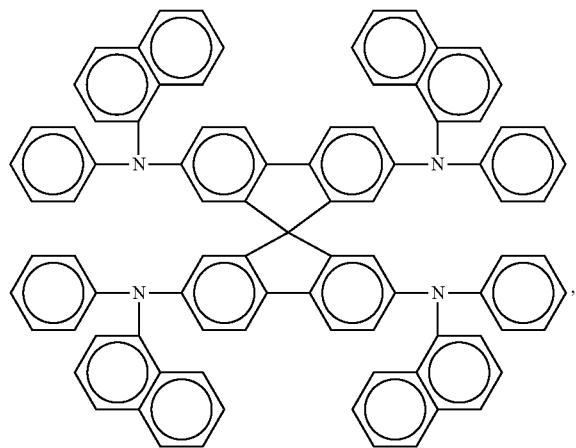

spiro-TAD represented by the following formula:

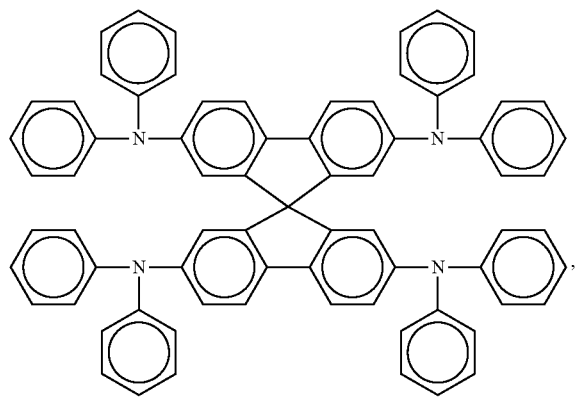

2-TNATA represented by the following formula:

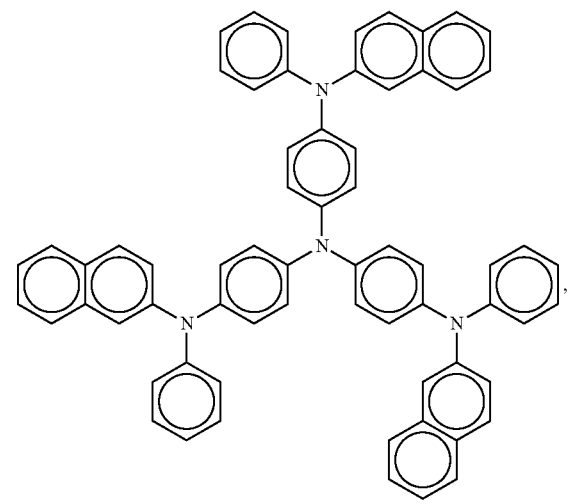

and the like.

Furthermore, any well-known arylamine compound used in the production of a conventional organic EL devices can be suitably used.

Furthermore, in regard to increasing a heat resistance of the devices, it is desirable that the arylamine compound used herein is an arylamine compound having a glass transition temperature of not lower than 90° C.

Among many arylamine compounds listed above, α-NPD, spiro-NPB, spiro-TAD and 2-TNATA are typical examples of a suitable arylamine compound because they have a glass transition temperature of not lower than 90° C.

In the organic EL device of the present invention, if the charge generation layer is constructed from a laminate including two different materials, one material constituting the laminate can be an organic material which constitutes a hole transporting layer in the light-emissive unit adjacent to the charge generation layer. Furthermore, in such a case, the hole transporting layer is desirably constructed from an arylamine compound used as the component (a).

The present invention will be further described with reference to the accompanying drawings.

As described above, the organic EL device according to the present invention is characterized in that the device includes an anode electrode/a plurality of light-emissive units (includes at least one light-emissive layer, principally consists of an organic material and generally has a laminated structure of two or more layers)/a cathode electrode. The plurality of light-emissive units are provided between the anode and cathode electrodes, and each light-emissive unit is partitioned with an electrically insulating charge generation layer having a resistivity or specific resistance of not less than $1.0 \times 10^2$ Ωcm, desirably not less than $1.0 \times 10^5$ Ωcm.

As shown in FIG. 1, the prior art organic EL device has a construction in which a single light-emissive unit is sandwiched in between the electrodes, and an electron ($e^-$) is injected from a cathode side into the unit, while a hole ($h^+$) is injected from an anode side into the unit so that the electron and the hole can be recombined inside the unit, thereby an excitation state to cause light emission.

Figure 2:
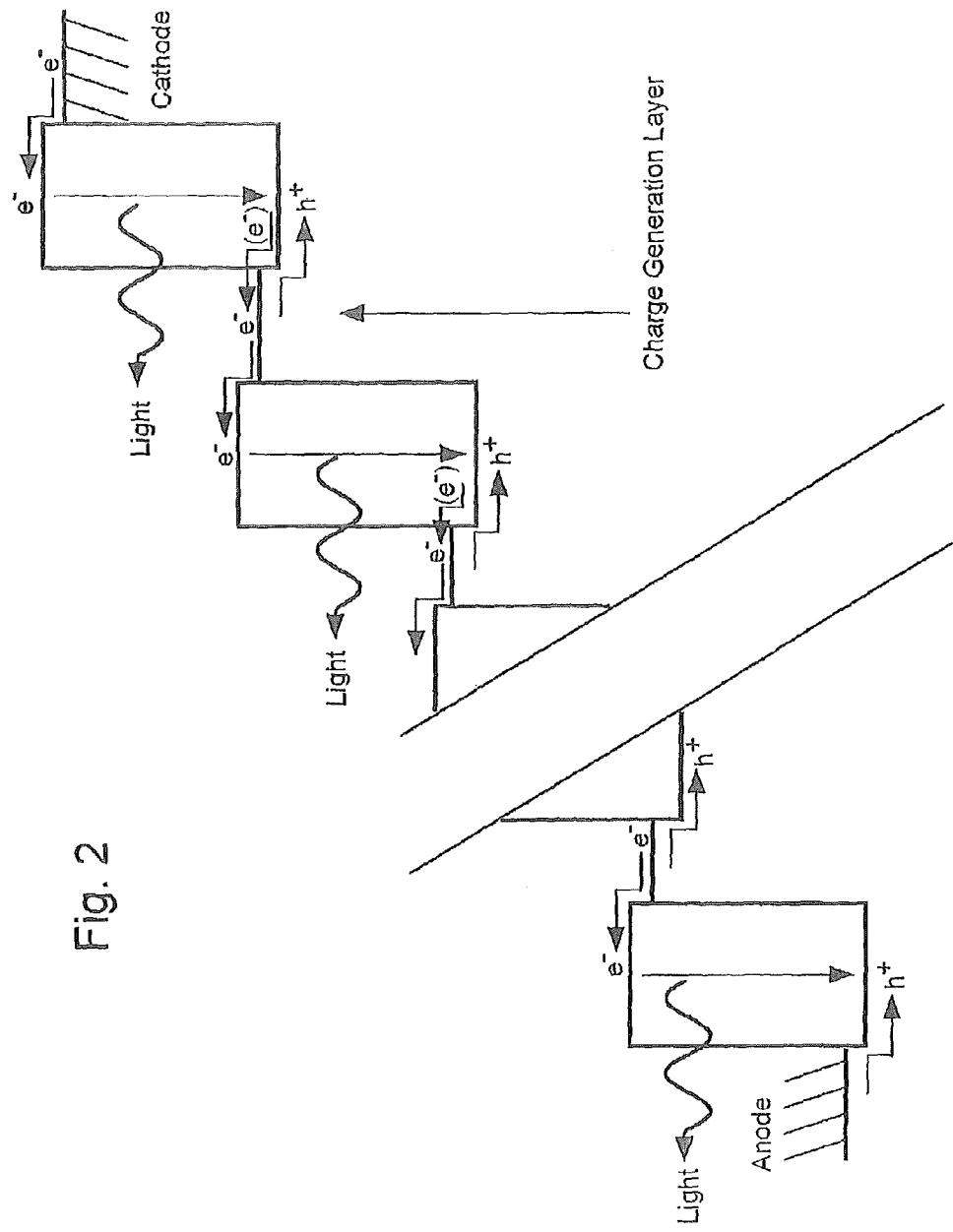
FIG. 2 a schematic view showing a light emission mechanism of the organic EL device according to the present invention.

Conversely, in the organic EL device according to the present invention, as shown in FIG. 2, a recombination of the electron and the hole can be made within the plurality of light-emissive units, each being partitioned by a charge generation layer, and thus a plurality of light emissions can be generated between the electrodes.

In the organic EL device of the present invention an electrically insulating material having a resistivity of not less than $1.0 \times 10^2$ Ωcm, desirably not less than $1.0 \times 10^5$ Ωcm is used as a material for forming a charge generation layer. Furthermore, generally, the charge generation layer is desirably a layer having a visible light transmittance of, not less than 50%. A transmittance of less than 50% will not provide the desired quantum efficiency (current efficiency) even if the device has a plurality of the light-emissive units because the light generated in the units is absorbed during its transmission through the charge generation layer.

Furthermore, both an inorganic material and an organic material can be used as a material for forming a charge generation layer, providing the material used has a specific resistivity described above. However, a suitable construction of the charge generation layer of the present invention, as described above, includes a laminate or a mixed layer formed from two different materials. Upon oxidation-reduction reaction between these two materials, a charge transfer complex including a radical cation and a radical anion is formed in the charge generation layer. Since a radical cation state and a radical anion state in the charge transfer complex are moved to a cathode direction and an anode direction, respectively, when a voltage is applied, the charge generation layer can inject a hole in a light-emissive unit adjacent to the layer on a cathode side and also can inject an electron in a light-emissive unit adjacent to the layer on an anode side.

As described above, the charge generation layer in the device of the present invention is desirably a laminate or a mixed layer formed from an arylamine compound such as the component (a) and a substance, such as the component (b), which may be an inorganic substance or an organic substance, capable of forming a charge transfer complex upon the oxidation-reduction reaction with the arylamine compound.

Figure 3:
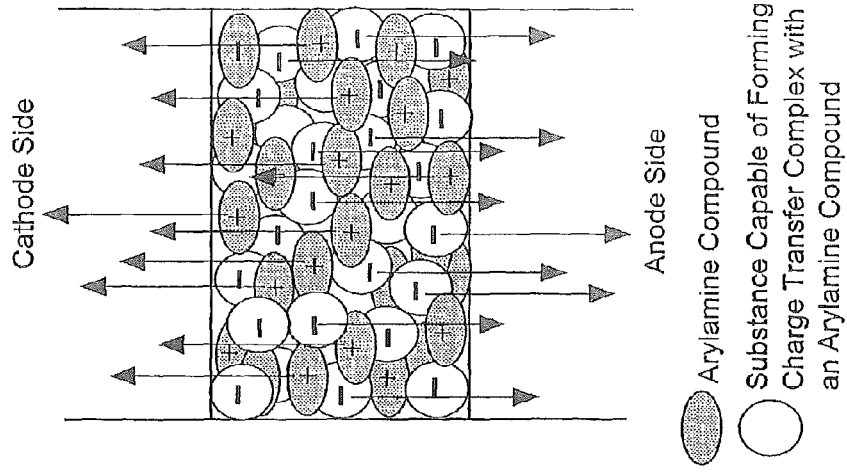
FIG. 3 is a schematic view showing a charge transfer complex formation and transfer of electrons and holes upon application of voltage in a charge generation layer having a laminated layer structure, according to the device of the present invention.

FIG. 3 is a schematic view showing a charge transfer complex formation in a charge generation layer which is a laminate including the above-described components (a) and (b), and the transfer of electrons and holes in the charge generation layer upon application of the voltage.

Figure 4:
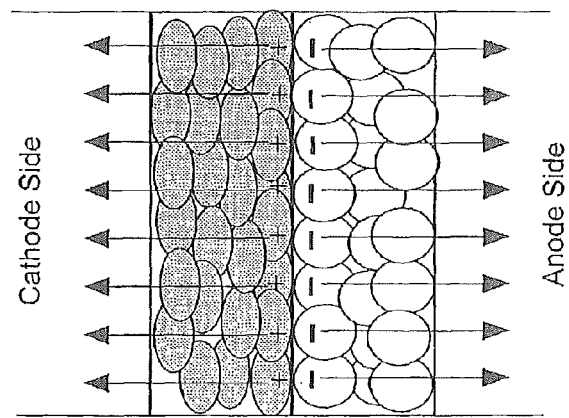
FIG. 4 is a schematic view showing a charge transfer complex formation and transfer of electrons and holes upon application of voltage in a charge generation layer having a mixed layer structure, according to the device of the present invention.

Furthermore, FIG. 4 is a schematic view showing a charge transfer complex formation and transfer of electrons and holes upon application of voltage in a charge generation layer which is a mixed layer including the above components (a) and (b).

Furthermore, whether or not the two compounds constituting the charge generation layer can form a charge transfer complex can be confirmed by using a spectroscopic analysis. For example, when the two compounds are examined, it can be confirmed that in separate use, the each compound does not exhibit an absorption peak in a near infrared region of the wavelength of 800 to 2,000 nm, however, if they are used as a mixed layer, the layer, can show an absorption peak in a near infrared region of the wavelength of 800 to 2,000 nm, i.e., the confirmed absorption peak clearly teaches the presence (or evidence) of an electron transfer between the two compounds.

Figure 5:
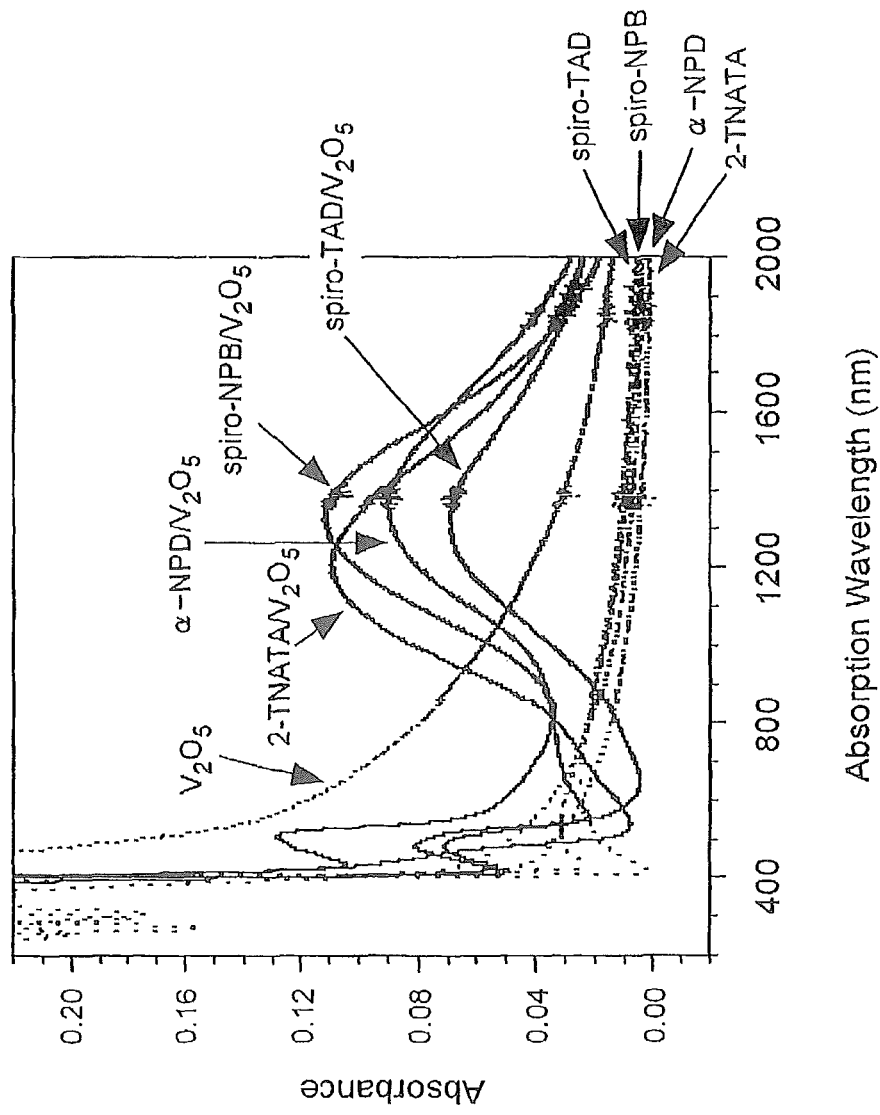
FIG. 5 is a graph of the absorption spectrum obtained in a single layer or mixed layer of an arylamine compound and vanadium pentaoxide.

FIG. 5 shows an absorption spectrum obtained in a sole use of each of arylamine compounds: 2-TNATA, α-NPD, spiro-TAD and spiro-NPB, and $V_2O_5$ (vanadium pentaoxide), and an absorption spectrum obtained in a mixed layer of each arylamine compound and vanadium pentaoxide. As can be appreciated from the graph of FIG. 5, the arylamine compounds and vanadium pentaoxide each cannot show a peak in a near IR region of the wavelength of 800 to 2,000 nm when they are used alone, but, if they are used in the form of a mixed layer including the arylamine compound and vanadium pentaoxide, the layer can show a prominent peak in a near IR region of the wavelength of 800 to 2,000 nm, from which a charge transfer complex formation can be confirmed.

Figure 6:
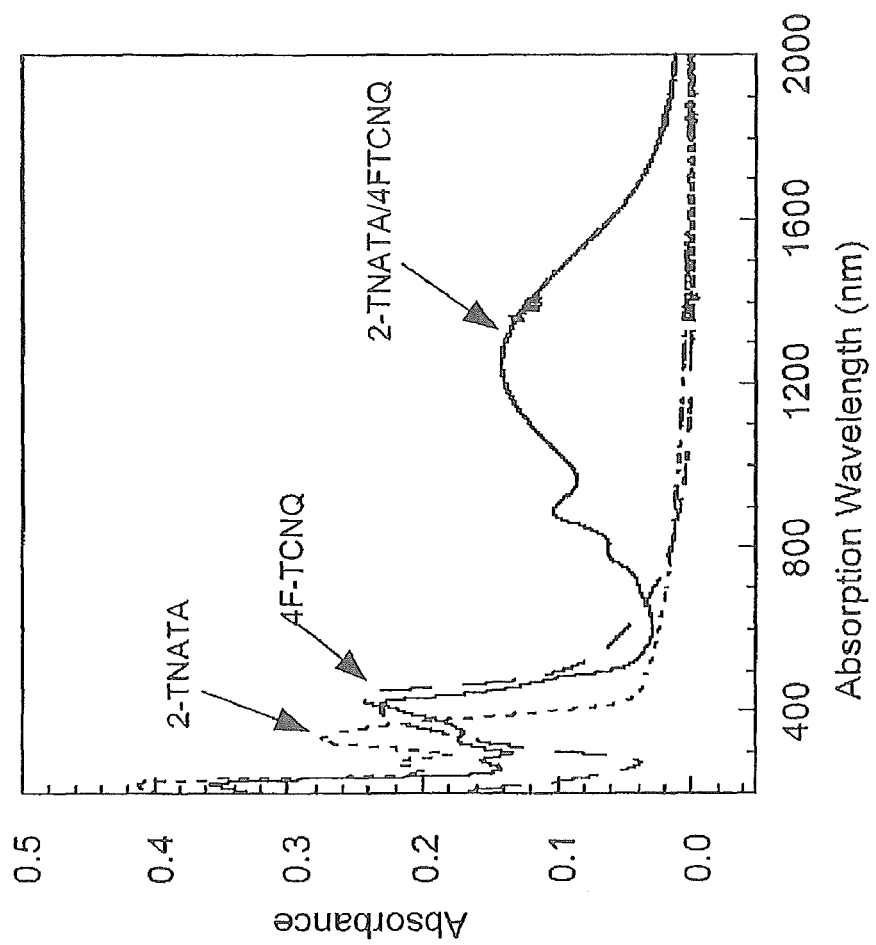
FIG. 6 is a graph of the absorption spectrum obtained in a single layer or mixed layer of 2-TNATA and 4F-TCNQ.
Figure 7:
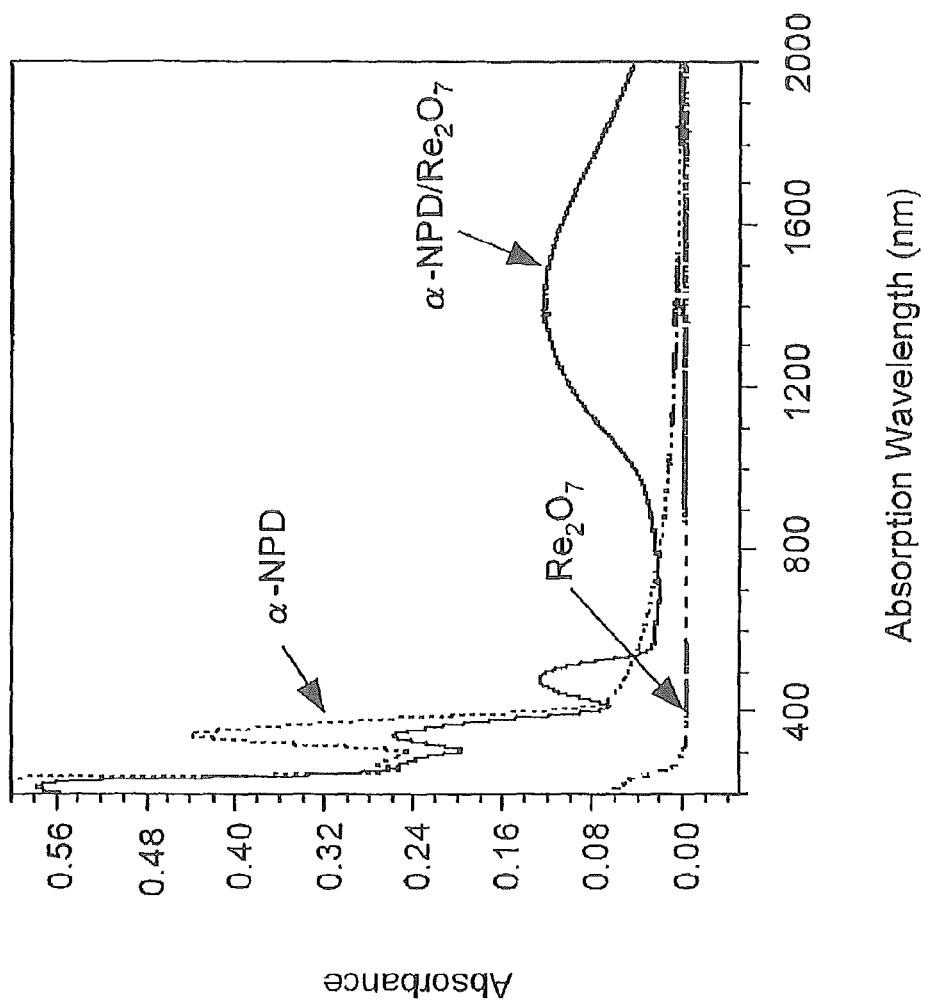
FIG. 7 is a graph of the absorption spectrum obtained in a single layer or mixed layer of α-NPD and rhenium heptaoxide.

FIG. 6 shows an absorption spectrum of each of 2-TNATA and 4F-TCNQ obtained when they are used in the form of a single layer or a mixed layer, and FIG. 7 shows an absorption spectrum obtained in a mixed layer of α-NPD and Re2O7 (di-rhenium heptaoxide).

The inventors of the present invention could observe from the absorption, spectrums of each of the mixed layers shown in FIGS. 5 to 7 that a new and third absorption spectrum was produced in a position of the near IR region (800 to 2,000 nm) upon the reaction caused with the electron transfer, and the third absorption spectrum is not a simply piled up spectrum curve obtained as a result of combination of a spectrum of one single substance with a spectrum of another single substance. The inventors have studied and found that a chemical reaction generated in the mixed layer is an important factor to ensure a charge transfer upon application of the voltage.

When two compounds (or layers) are laminated, it is easily conceived that a chemical reaction can be generated in an interfacial surface between the two layers. Thus, it is true that the intended and desired properties can be obtained in a charge generation layer when the layer is formed by lamination of the two compounds.

In the present invention, the terms "light-emissive unit", as explained above, means a "component of the conventional organic EL device" excluding an anode and a cathode.

The "component of the conventional organic EL device" includes, for example, (anode)/a light-emissive layer/(cathode), (anode)/a hole-transporting layer/a light-emissive layer/(cathode), (anode)/a hole-transporting layer/a light-emissive layer/an electron-transporting layer/(cathode), (anode)/a hole injection layer/a hole-transporting layer/a light-emissive layer/an electron-transporting layer/(cathode) and the like.

In the organic EL device according to the present invention, the light-emissive units may have any laminate structure, providing the laminate structure satisfies the requirement that each light-emissive unit is partitioned with an electrically insulating charge generation layer and that there are a plurality of light-emissive units. Furthermore, the materials used in the formation of a light-emissive layer, a hole-transporting layer, a hole injection layer, an electron-transporting layer, an electron injection layer, and the like are not restricted to any specific material and can be any conventional material used in the formation of these layers.

Furthermore, the light-emissive or luminescent materials which may be added to a light-emissive layer are also not restricted to a specific material, and can be any well-known material which includes, for example, a wide variety of fluorescent materials and phosphorescent materials.

Generally, a metal having a low work function or a metal alloy, a metal oxide, and the like, containing such a low work function metal is mainly used as the cathode material. Specifically, the cathode material includes, for example, a single body of a metal, for example, an alkaline metal such as Li, and the like, an alkaline earth metal such as Mg, Ca, and the like, a rare earth metal such as Eu, and the like, and a metal alloy of these metals and Al, Ag, In, and the like. Furthermore, in the device construction suggested by the inventors in Japanese Laid-open Patent Application Nos. 10-270171 and 2001-102175, in which a metal-doped organic layer is used in an interfacial surface between a cathode and an organic layer, any electrically conducting material may be used as the cathode material. In this construction, the selection of the cathode material is not restricted by properties such as work function of the selected material.

Moreover, if an organic layer adjacent to a cathode is constructed from an organic metal complex compound containing at least one of alkaline metal ions, alkaline earth metal ions and rare metal ions using the technologies disclosed by the inventors in their Japanese Laid-open Patent Application Nos. 11-233262 and 2000-182774, a metal capable of reducing a metal ion contained in the complex compound in vacuum to the corresponding metal, for example, a thermally reducible metal such as Al, Zr, Ti, Si, and the like, or an alloy including these metals may be used as the cathode material. Among these metals, aluminum (Al) which is generally and widely used as a wiring material is particularly desired as the cathode material in view of its easy vapor deposition, high light reflectance and chemical stability.

Similarly, the anode material is not restricted to a specific material. For example, a transparent conducting material such as ITO (indium tin oxide), IZO (indium zinc oxide), and the like, can be used as the anode material.

Furthermore, assuming that an ITO coating is formed with a sputtering method using the process suggested in Japanese Patent Application No. 2001-142672 to avoid damage in an organic layer, a transparent conducting material such as above described ITO and IZO may be used as the cathode material if a metal-doped organic layer described in Japanese Laid-open Patent Application No. 10-270171 is used as an electron injection layer in the manner described above. Accordingly, it becomes possible to produce a transparent light-emitting device by forming both of the cathode and the anode as a transparent electrode, because the organic layer and the charge generation layer are also transparent. Alternatively, contrary to the structure of the above-described general organic EL device, if an anode is formed from any metal material and a cathode is formed as a transparent electrode, it is possible to provide a device structure in which the emitted light can be projected from a laminated-layers side of the device, not from a substrate side of the device.

In addition, the order of the steps for forming layers is not restricted to any specific order. Namely, the layer formation may not always be started from an anode side of the device, and the layers may be formed from a cathode side of the device.

In the organic EL device of the present invention, types of the material used in the formation of cathode and anode electrodes or the method for forming a charge injection layer adjacent to these electrodes may be based on well-known technology widely used in the conventional EL devices, providing that two or more light-emissive units are contained between the opposed cathode and anode electrodes and each light-emissive unit is partitioned by a charge generation layer having a resistivity of not less than $1.0 \times 10^2$ Ωcm, desirably not less than $1.0 \times 10^5$ Ωcm.

The organic EL device of the present invention having a novel device structure is distinguishable from the conventional organic EL devices in view of the following notably different characteristics.

Firstly, in the organic EL device of the present invention, a theoretical limitation is not applied to the quantum efficiency of the device, whereas in the conventional EL devices, an upper limitation of the quantum efficiency which is a ratio of photon (number)/sec vs. electron (number)/sec, simply determined in an external circuit, is 1 (=100%) in theory. This is because an injection of hole ($h^+$) shown in FIG. 2 means a generation of a radical cation as a function of withdrawal of electrons from a valance band (or HOMO, highest occupied molecular orbital) of an organic layer, and thus the electrons withdrawn from a valance band of the organic layer constituting a layer adjacent to the charge generation layer on a cathode side is injected into an electron conduction band (or LUMO, lowest unoccupied molecular orbital) of an organic layer constituting a layer adjacent to the layer on an anode side, thereby producing a light-emissive excitation state. Namely, the withdrawn electrons are again utilized in the formation of a light-emissive excitation state.

Accordingly, in the organic EL device of the present invention, the quantum efficiency thereof is calculated as a sum of the quantum efficiency of each light-emissive unit partitioned with a charge generation layer wherein the quantum efficiency is defined as a ratio of electrons (apparent number) passing thorough each light-emissive unit/sec vs. photons (number), emitted from each light-emissive unit/sec, and therefore the quantum efficiency has no upper limit.

Namely, the organic EL device of the present invention can still be operated as a planar and thin film-shaped light-emissive device capable of emitting light only from a crossed area of the cathode and the anode as in the conventional organic EL devices, although it has a circuit structure the same as that of the conventional devices in which plural EL devices are connected in series with a metal wiring, because the present device has a charge generation layer having a very thin and transparent layer structure and the charge generation layer is constructed from an (electrically) insulating layer having a resistivity which is substantially the same as that of the organic layer.

Although the organic EL device of the present invention is only constructed from an insulating material having a resistivity of not less than $1.0 \times 10^2$ Ωcm, desirably not less than $1.0 \times 10^5$ Ωcm, except for the electrodes, the organic EL device can be operated at a driving voltage which is a sum of the potential reduction amount (Vn) consumed in each of the light-emissive units, i.e., V=V1+V2+ . . . +Vn, because the present device is consequently operated just as if the plurality (n) of the conventional EL devices were connected in series. Accordingly, an advantage obtained in conventional devices, i.e., a low voltage driving at 10 volts or less, cannot be obtained in the present device with increase of the number (n) of the light-emissive units.

However, the organic EL device of the present invention still has some advantages over conventional organic EL devices. In conventional devices, since the luminance is substantially proportional to a current density, it was essentially required to apply a higher current density to obtain an increased luminance. On the other hand, since, as previously mentioned, the operational life-time of the device was inversely proportional to the current density (not to a driving voltage), a high luminance emission results in a shortened operational life-time of the device.

Contrary to the drawbacks of conventional devices, in the organic EL device of the present invention, if it is desired to obtain an n-times increased luminance at a desired current density, such a increase of the luminance can be attained by increasing the number of the light-emissive units (each having the same construction) used between the electrodes by n-times, without increasing the current density.

In this method, the driving voltage will be also increased to a level of n-times or more. However, it should be noted that an unexpected and important advantage is that an n-times increased luminance can be achieved without sacrificing the operational life-time.

Furthermore, in the organic EL device of the present invention, a layer thickness between the cathode and the anode can be naturally increased by increasing the number of the light-emissive units used therein. For example, assuming that the number of the light-emissive units between the electrodes is "n", a layer thickness of the present device is increased to about n-times of that of the conventional EL devices. In addition, since the number of the light-emissive units in the present device is not restrictive, layer thickness between the electrodes is also not restrictive. In view of the fact that in conventional EL devices, a layer thickness between the electrodes of not exceeding 1 μm (practically, not more than 2000 Å (not more than 200 nm)) and that a driving voltage of 25 volts or less must be applied, the present EL device has an essentially different characteristics which cannot be found, in the conventional EL devices (above mentioned Kodak Patent, Japanese Laid-open Patent Application Nos. 59-194393, 63-264692 and 2-15595, U.S. Pat. Nos. 4,539,507, 4,769, 292, and 4,885,211).

Namely, in the organic EL device of the present invention, there is no necessity to define an upper limit of the layer thickness between the electrodes, an upper limit of the driving voltage and an upper limit of the quantum efficiency (current efficiency).

On the other hand, in conventional organic EL devices, an increase of the driving voltage results only in a reduction of the power conversion efficiency (w/w). Conversely, according to the organic EL device of the present invention, in principle, the conversion efficiency (w/w) can be maintained without any change, because if "n" of the light-emissive units are introduced between the electrodes, the light-emission starting voltage (turn on voltage), and the like, are increased by about n-times, and accordingly the voltage for obtaining the desired luminance is increased by about n-times, and in addition to the increase of these voltages, the quantum efficiency (current efficiency) can be also increased by about n-times.

Moreover, the organic EL device of the present invention containing a plurality of the light-emissive units has a secondary advantage of being able to reduce the risk of short circuiting in the device. In conventional EL devices containing only one light-emissive unit, if an electrical short circuit is caused between a cathode and an anode due to presence of pin-holes, etc., in the layer of the unit, the EL devices could immediately change to a state of emitting no light. Conversely, in the organic EL device of the present invention, since the layer thickness between the electrodes is thick, a risk of short circuiting can be reduced, and at the same time, even if short circuiting is caused in some light-emissive units, the worst scenario result such as non-light emission can be avoided because the remaining light-emissive units can still emit light. Specifically, when the EL device is designed to be driven at a constant current, a driving voltage is only reduced by an amount corresponding to the short circuited units, and the remaining non-short circuited units can emit light normally.

In addition to the above advantages, for example, when the organic EL device of the present invention is applied to an EL display device having a simple matrix structure, a reduction of the current density means that a voltage reduction due to the wiring resistance and a temperature increase in the substrate can be largely reduced in comparison with a conventional display device. Furthermore, a higher driving voltage between the electrodes, which sandwich the light-emissive element portion, in comparison with the conventional devices means that a voltage reduction due to the wiring resistance does not largely cause a reduction of the luminance (the effect due the higher driving voltage can be sufficiently understood just from considering the influence of the possible potential reduction of 1 volt due to the wiring resistance to a reduction of the luminance in comparison with an EL device capable of providing a luminance of 1,000 cd/m$^2$ at 5 volts and an EL device capable of providing a luminance of 1,000 cd/m$^2$ at 50 volts). This effect, in combination with another characteristic of the EL device of the present invention where the device naturally has a low voltage reduction in the wiring portion thereof, enables to achieve a display device controllable a constant voltage which can not be provided using a conventional device.

Furthermore, the above-described characteristics advantageously affect other uses for obtaining an uniform light emission in a large surface area, in particular, for use as an illumination apparatus. In conventional organic EL devices, since an electrode material used therein, especially a transparent electrode material, typically ITO, etc., has a resistivity of up to $10^{-4}$ Ωcm, which is about 100 Ωcm higher than a resistivity of metal (up to $10^{-6}$ cm), a voltage (V) or electric field E (V/cm) applied to the light-emissive unit reduces with an increase of the distance from a contact point of electric power, so that unevenness (difference of luminance) in the luminance occurs between a near portion to and a far portion from a contact point of electric power. Conversely, according to the organic EL device of the present invention, since an electric current in obtaining the desired luminance can be largely reduced in comparison with conventional EL devices, the potential reduction can be diminished with the result that substantially uniform light emission can be obtained in a large surface illumination apparatus.

Furthermore, in the formation of the charge generation layer, since the present invention is characterized by intentionally using a material having a considerably-increased resistivity (of not less than $1.0 \times 10^2$ Ωcm, desirably not less than $1.0 \times 10^5$ Ωcm) than that of an ITO and other electrically conductive materials (about $10^{-4}$ Ωcm), a shadow mask for defining a vapor deposition area, which is with the same as that used in the formation of the patterned organic layer, can be used in the layer formation process of the charge generation layer, and thus the frequent change and precise positioning of the shadow mask can be excluded from the production process except for the formation of the electrodes. Namely, according to the present invention, it becomes possible to achieve a remarkably increased productivity.

FIG. 8 is a schematic cross-sectional view illustrating a laminated structure of the organic EL device according to an embodiment of the present invention. A glass substrate (transparent substrate) 1 includes, laminated in sequence thereon, a transparent electrode 2 constituting an anode electrode, a light-emissive unit 3-1, a charge generation layer 4-1, a light-emissive unit 3-2, a charge generation layer 4-2, ..., a charge generation layer 4-($n$−1), a light-emissive unit (3-$n$) wherein the n=1, 2, 3, ..., and finally a cathode electrode (metal electrode) 5. In these elements (layers), the glass substrate (transparent substrate) 1, the transparent anode electrode 2, the light-emissive unit (3-$n$) wherein n is 1, 2, 3, ..., and the cathode electrode 5 each is a well-known element (layer). The new feature in the EL device of the present invention resides in that a plurality of light-emissive units (3-$n$, wherein n is 1, 2, 3, ... ) are contained between both electrodes and are partitioned with an electrically insulating charge generation layer (4-$n$, wherein n is 1, 2, 3, ... ) having a resistivity of not less than $1.0 \times 10^2$ Ωcm.

Furthermore, in regard to organic EL devices, it is known that the characteristics thereof such as driving voltage, etc., can be varied depending upon the work function; the work function being one property of the electrode material. Referring to the organic EL device of the present invention, the charge generation layer 4-$n$ used therein is not acting as an electrode. However, since an electron is injected into a direction of the anode electrode and a hole is injected in a direction of the cathode electrode, in the formation of the above-described components of the light-emissive unit, particularly the method for forming a electron injection (transporting) layer and a hole injection (transporting) layer, both being adjacent to a charge generation layer, is essential for reducing an energy barrier in the injection of the charge (electron and hole) into each light-emissive unit.

For example, if it is intended to inject an electron from each charge generation layer 4-$n$ to a direction of the anode electrode, it is desirable that, as is disclosed in Japanese Laid-open Patent Application Nos. 10-270171 and 2001-102175, an electron injection layer having a mixed layer of an organic compound and a metal functioning as an electron donating (donor) dopant, is formed as a layer adjacent to the charge generation layer in anode side. The donor dopant desirably includes at least one metal selected from alkaline metals, alkaline earth metals and rare earth metals.

Furthermore, in the electron injection layer, a molar ratio of the metal as the donor dopant is desirably in the range of 0.1 to 10 with respect to the organic compound. A molar ratio of less than 0.1 results in a reduction of the doping effect because a concentration of the molecule reduced with the dopant (hereinafter, referred to as a "reduced molecule") is reduced excessively. A molar ratio above 10 also results in a reduction of the doping effects because a concentration of the dopant in the layer is significantly increased in comparison with concentration of the organic compound, thus causing an excessive reduction of the reduced molecule in the layer.

The application of the above-described electron injection layer-containing structure to a light-emissive unit of the organic EL device achieves an energy barrier-free electron injection to each of the light-emissive units regardless of the work function of the material constituting a charge generation layer.

Furthermore, the light-emissive unit may have a structure in which an electron injection layer including a metal selected from alkaline metals, alkaline earth metals and rare earth metals, and having a layer thickness of up to 5 nm (desirably 0.2 to 5 nm) is disposed as a layer adjacent to the charge generation layer on an anode side. A layer thickness of above 5 nm is not desirable because it reduces a light transmittance, and at the same time, makes the device unstable because the content of the metal which has a high reactivity and is unstable in air is excessively increased in the layer. Moreover, in this metal layer having a layer thickness of up to 5 nm, it is considered that a substantial amount of the metal layer can be diffused into an organic layer, to result in a layer having a composition which is substantially the same as that of the above-described metal doping layer. The resulting layer at least has no form of the metal layer having an electrical conductivity.

For example, if the electron is injected from each charge generation layer 4-$n$ in the anode direction, it is also desirable that the electron injection layer, which is disclosed in Japanese Laid-open Patent Application Nos. 11-233262 and 2000-182774 (corresponding U.S. Pat. No. 6,396,209) (J. Endo, T. Matsumoto, and J. Kido, Jpn. J. Appl. Phys. Vol. 41 (2002) pp. L800-L803), is provided on the anode side of the charge generation layer. The electron injection layer of this type is explained as an "in-situ reaction generating layer" which is generated by depositing a thermally reducible metal such as aluminum on a compound containing an alkaline metal ion, an alkaline earth metal ion and a rare earth metal ion to reduce the metal ions into a metal condition. In the device of the present invention, it is desirable to supply the very thin thermally reducible metal on the compound by a minimum amount required for the reduction reaction. If the metal ion in the compound is reduced, the supplied thermally reducible metal itself is oxidized to be a insulative compound having a resistivity not less than $1.0 \times 10^2$ $\Omega$cm. The very thin thermally reducible metal has a layer thickness not more than 10 nm. If the layer thickness of the thermally reducible metal is more than 10 nm, a metal atom, which does not contribute to the reduction reaction, remains so that the transparency and insulation property are lost.

In addition to an organic metal complex compound described in the above mentioned patent document (Japanese Laid-open Patent Application Nos. 11-233262 and 2000-182774), an inorganic compound can be used as the compound including the alkaline metal ion, alkaline earth metal ion and rare earth metal ion, which are used for the above mentioned "in-situ reaction generating layer". An oxide and halide including the alkaline metal ion, alkaline earth metal ion and rare earth metal ion can be used as the compound for the in-situ reaction generating layer, and further, any inorganic compound including the alkaline metal ion, alkaline earth metal ion and rare earth metal ion can be used as the compound.

Furthermore, it is also desirable to use different types of electron injection (transporting) layers in above mentioned Japanese Laid-open Patent Application Nos. 10-270171, 2001-102175, 11-233262 and 2000-182774 (corresponding to U.S. Pat. No. 6,396,209) in a superposed condition. The metal doping layer in the Japanese Laid-open Patent Application No. 10-270171 or 2001-102175 is desirably deposited on the organic layer (including light-emissive layer), by a predetermined thickness, as a low resistance electron transporting layer, then the in-situ reaction generating layer described in the Japanese Laid-open Patent Application Nos. 11-233262 and 2000-182774 is superposed on the metal doping layer. As mentioned above, a technical idea in which an electron injection layer contacting the cathode electrode of the conventional electroluminescent device is formed by using superposed different types of electron injection (transporting) layers is described in the Japanese Patent Application No. 2002-273656 by the inventors of the present invention.

In this case, the in-situ reaction generating layer contacts the charge generation layer on an anode side. According to the present invention, an interaction between a material used for the charge generation layer and a reactive metal such as alkaline metal can be avoided. As a result, it is found that such method is a desirable for forming an electron injection layer on a point that the electron injection barrier from the charge generation layer to the light emissive unit can be lowered.

Furthermore, for example in the injection of holes from each charge generation layer 4-$n$ to a direction of the cathode electrode, a hole injection layer, suggested by the inventors in Japanese Laid-open Patent Application Nos. 11-251067 and 2001-244079, which contains a doped electron-accepting compound (Lewis acid compound) having a property of oxidizing an organic compound in terms of Lewis, acid chemistry may be formed as a layer adjacent to the charge generation layer in a cathode side. Regardless of the work function of the material constituting the charge generation layer 4-$n$, hole injection in the absence of an energy barrier can be achieved.

Moreover, a layer of the electron-accepting compound (Lewis acid compound) which is very thin and thus ensures a transparency may be formed as a hole injection layer. In this method, a layer thickness of the hole injection layer is desirably 30 nm or less, more desirably in the range of 0.5 to 30 nm. The layer thickness above 30 nm causes a reduction of the light transmittance, and at the same time, makes the device unstable because a content of the Lewis acid compound which has a high reactiveness and is unstable in air is excessively included in the layer.

The electron-accepting compound (Lewis acid compound) used herein is not restricted to a specific compound. For example, electron-accepting compound includes an inorganic compound such as ferric chloride, ferric bromide, ferric iodide, aluminum chloride, aluminum bromide, aluminum iodide, gallium chloride, gallium bromide, gallium iodide, indium chloride, indium bromide, indium iodide, antimony pentachloride, arsenic pentafluoride, boron trifluoride, and the like, and an organic compound such as DDQ (dicyanodichloroquinone), TNF (trinitro-fluorenone), TCNQ (tetracyanoquinodimethane), 4F-TCNQ (tetrafluoro-tetracyanoquinodimethane), and the like.

In the hole injection layer, a molar ratio of the organic compound and the electron-accepting compound (dopant compound) is desirably in the range of 0.01 to 10 with respect to the organic compound. A molar ratio of less than 0.01 results in a reduction of the doping effects because a concentration of the molecule oxidized with the dopant (hereinafter, referred also to an "oxidized molecule") is excessively reduced. A molar ratio above 10 also results in a reduction of the doping effects because a concentration of the dopant in the layer is remarkably increased in comparison with concentration of the organic compound, thus causing an excessive reduction of a concentration of the oxidized molecule in the layer.

Further, if the material forming a charge generation layer has a work function of not less than 4.5 eV, it may be sometimes possible to inject holes to each: light-emissive unit without specially using an electron-accepting compound (Lewis acid compound).

Conversely, as shown in Example 2 described hereinafter, the Lewis acid compound itself may sometimes act as a component of the charge generation layer.

In the light-emissive units used in the present invention, the layers which are formed in direct contact with the cathode or anode may have the same composition as that of the layer adjacent to the charge generation layer on an anode side or the layer adjacent to the charge generation layer on a cathode side, respectively, or the electron injection layer and the hole injection layer each may have some other compositions. Of course, the electron injection layer and the hole injection layer used in the conventional EL devices may be suitably used.

In comparison with conventional organic EL devices, the amount of time it takes for the layer to be formed in the production of the organic EL device of the present invention is necessarily longer. Furthermore, since the present method is characterized in that the substantially same processes are repeatedly carried out, conventional batch system-based vapor deposition apparatuses which are currently widely used for layer formation require an excessively long processing time. Moreover, an increase, of the production costs is of concern because a large amount of expensive organic materials must be used, compared to conventional organic EL devices.

In such a case, it is suggested by the inventors in Japanese Patent Application No. 2001-153367 to use an in line-line system-based continuous layer formation apparatus. Using this apparatus, the time required for layer formation can be largely shortened and the efficiency of materials use can be increased so as to approach 100%.

Furthermore, in the formation of the organic layer, the charge generation layer and the electrode layer which constitute the organic EL device of the present invention, any well-known deposition method which is conventionally used such as a resistive heating vapor deposition method, an electron beam vapor deposition method, a laser beam vapor deposition method, a sputtering method, and the like, can be used.

In particular, when an inorganic substance or compound such as metal oxide is used as an element for forming a charge generation layer, a vapor deposition method must be carried out with care, because there is a tendency that a deposited layer may have a composition which is outside of the desired stoichiometric composition due to separation, etc., of oxygen atoms from the compound.

Furthermore, when an inorganic substance or compound is deposited using a sputtering method, it is important to use a method in which a substrate having the formed organic layer is disposed separately from the plasma generated during the deposition process to thereby avoid damage of the organic layer. At the same time, it is also important that the molecules of the sputtered inorganic compounds are softly deposited on the organic layer with a kinetic energy up to a predetermined level in order to reduce damage in the device.

For example, the facing target sputtering apparatus in which a pair of opposed targets arranged separately from each other at a certain distance have a reflection electrode for reflecting electrons against a front peripheral portion of each of the targets, and a magnetic field generating device which is included to form a parallel magnetic field having a portion parallel to a surface of the target in the vicinity of the peripheral portion of each target (see, Japanese Patent Application No. 2001-142672) can be suitably used in the formation of the charge generation layer of the present invention, too.

In addition, all the layers to be formed on a substrate can be formed by the vapor deposition method in which all layers are formed on a substrate by heating a vaporizable material in a vacuum to deposit a vaporized or sublimed material on the substrate, and includes transporting a substrate in a direction of planar surface thereof, a deposition area being open in a lower surface of the substrate; providing a container, in a lower position of the transporting substrate, including a vaporizable material having a deposition width which can cover the deposition area extending in a direction perpendicular to the transportation direction of the substrate; and heating the container, thereby vaporizing or subliming and thus depositing the vaporizable material in the container (Japanese Patent Application No. 2001-153367).

Furthermore, contrary to conventional EL devices, using the organic EL device of the present invention, the highest light emission efficiency can be obtained when an optical path length from light-emissive site to light-reflective electrode is almost an odd-numbered times greater than a quarter wavelength of light, i.e., $\lambda \times (2n-1)/4$ wherein n is 1, 2, 3, . . . , since an important feature in the present invention is that two or more light-emissive site are provided at intervals.

In conventional EL devices, a structure is adopted wherein an optical path length from light-emissive site to light-reflective electrode is adjusted to approximately an odd-numbered times a quarter wavelength of light. In such devices, even if the organic layer is formed at a larger thickness above the quarter wavelength of light, the result is only an undesirable increase of the driving voltage.

However, as disclosed in above mentioned Japanese Laid-open Patent Application No. 2001-102175, if a combination of the electron transporting organic compound and the alkaline metal (both constituting an electron injection layer adjacent to a light-reflective cathode) are appropriately selected, it becomes possible to inhibit an increase of the driving voltage at a larger layer thickness of about 1 μm, and a color hue (namely, a profile of the emission spectrum) can be largely changed because an interference effect can be remarkably increased with an increase of the layer thickness.

For example, assuming that an optical path length of the electron injection layer is adjusted to be approximately an odd-numbered times a quarter wavelength of light, i.e., $\lambda \times (2n-1)/4$ wherein n is 1, 2, 3, . . . , a profile of the resulting emission spectrum is narrowed by an increase of n. On the other hand, if an optical path length of the electron injection layer is adjusted to be approximately an even-numbered times a quarter wavelength of light, i.e., $\lambda \times (2n)/4$ wherein n is 1, 2, 3, . . . , there arises a notable interference effect with an increase of n, with the result that the emission efficiency is largely deteriorated because an emission in the original light-emitting peak is offset with the notable interference effect.

Accordingly, when the organic EL device has the resultant structure in which n is large and a plurality of light-emissive site are contained as in the EL device of the present invention, it is essential to exactly control the layer thickness from each light-emissive site to a light-reflective electrode.

To be free from such troublesome fine adjustment of layer thickness, it is desirable to construct the cathode electrode, which was light reflective electrode conventionally when the anode electrode is a transparent electrode, a non-reflective black electrode, or to construct at least one layer existed in the cathode electrode direction so as to function as a light absorbing layer. Accordingly, problems with light interference can be avoided.

Conversely, if the anode electrode is the light reflective electrode, it is desirable that the anode electrode itself or at least one layer existing in the anode electrode direction have a light absorbing function.

If a light diffuse reflection surface is provided on one of the electrodes when the other electrode is the transparent electrode, problems with light interference can be avoided in theory.

Furthermore, as is shown in the appended examples, another feature of the present invention is that the light-emissive units each have different emission colors so that a desired mixed (superimposed) color emission can be obtained. In this case, it is also necessary to optimize the optical path length from light-emissive site to light-reflective electrode in the manner described above. The necessity for the optimization of the layer thickness will depend on the emission color in each light-emissive unit.

EXAMPLES

The present invention will be further described with reference to the examples below. Note, however, that the present invention is not restricted to these examples.

In the following examples, the vapor deposition of the organic compound and the metal, as well as formation of the charge generation layer, was carried out by using a vapor deposition apparatus commercially available from VIEETECH JAPAN. The control of the deposition rate of the vapor deposition material and of the thickness of the deposited layers is carried out by using a thickness monitor, provided with a quartz oscillator and attached to the vapor deposition apparatus, "CRTM-8000" commercially available from ULVAC. Furthermore, to determine an actual layer thickness after the layer formation, a stylus step meter "P10" commercially available from Tencor, Co., was used. Furthermore, the characteristics of the organic EL device were evaluated with the source meter "2400", commercially available from KEITHLEY, and the luminance meter "BM-8", commercially available from TOPCON. A DC voltage was stepwise applied at an increasing rate of 0.2 volts per 2 seconds to the EL device having an ITO anode and an aluminum (Al) cathode, and the luminance and the electric current were determined after a lapse of one second from the completion of each increase of the voltage. The EL spectrum was determined by using the optical multi-channel analyzer, "PMA-11" commercially available from HAMAMATSU PHOTONICS, driven at a constant electric current.

Reference Example 1

Example for the Production of the Conventional Organic EL Device-Green Light-Emitting Device The conventional organic EL device having a laminate structure shown in FIG. 9 was produced as follows.

A glass substrate 1 used herein includes, coated in the predetermined pattern on a surface thereof, a transparent anode electrode 2 including an ITO (indium-tin oxide, sputtered product commercially available from ASAHI GLASS, or ion plating product commercially available from Nippon Sheet Glass Co., Ltd.) having a sheet resistance of about 20Ω/□ (Ω/sq.) (see, FIG. 10A). Alpha(α)-NPD having a hole transporting property was deposited, through a metal mask (shadow mask) 40 for organic layer formation (see FIG. 10B), onto the ITO-coated glass substrate 1 under vacuum of about $10^{-6}$ Torr and at a deposition rate of about 2 Å/sec to form a hole transportation layer 6 having a thickness of about 700 Å.

An organic-metal complex of tris(8-quinolinolato) aluminum (hereinafter, briefly referred to as "Alq") is represented by the following formula:

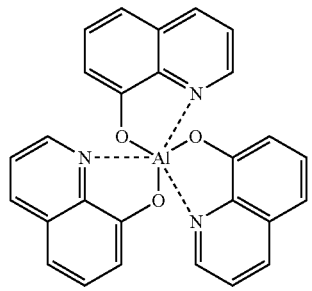

and a coumarin derivative which is a green light-emissive fluorescent dye, "C545T"(trade name) commercially available from KODAK, were deposited onto the hole transportation layer 6 under vacuum vapor deposition conditions to form a light-emissive layer 7 having a thickness of about 400 Å. Each deposition rate was adjusted so that the resulting light-emissive layer 7 contains a fluorescent dye in a concentration of about 1% by weight.

Thereafter, bathocuproine represented by the following formula:

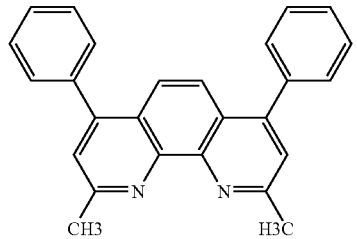 [SMILES: Cc1cc(-c2ccccc2)c2ccc3c(-c4ccccc4)cc(C)nc3c2n1]

and metal cesium (Cs) in a molar ratio of about 1:1 were co-deposited under vacuum vapor deposition conditions to form a metal (Cs)-doped electron injection layer 8 having a thickness of about 200 Å on the light-emissive layer 7. Each deposition rate was adjusted to obtain the molar ratio of about 1:1.

Finally, aluminum (Al) was deposited through a metal mask (shadow mask) 41 for cathode layer formation (see, FIG. 10C) at a deposition rate of about 10 Å/sec onto the electron injection layer 8 to form a cathode electrode 5 having a thickness of about 1,000 Å. An organic EL device having a square light-emissive area of 0.2 cm (length) by 0.2 cm (width) was thus obtained (see, FIG. 10D).

Figure 16:
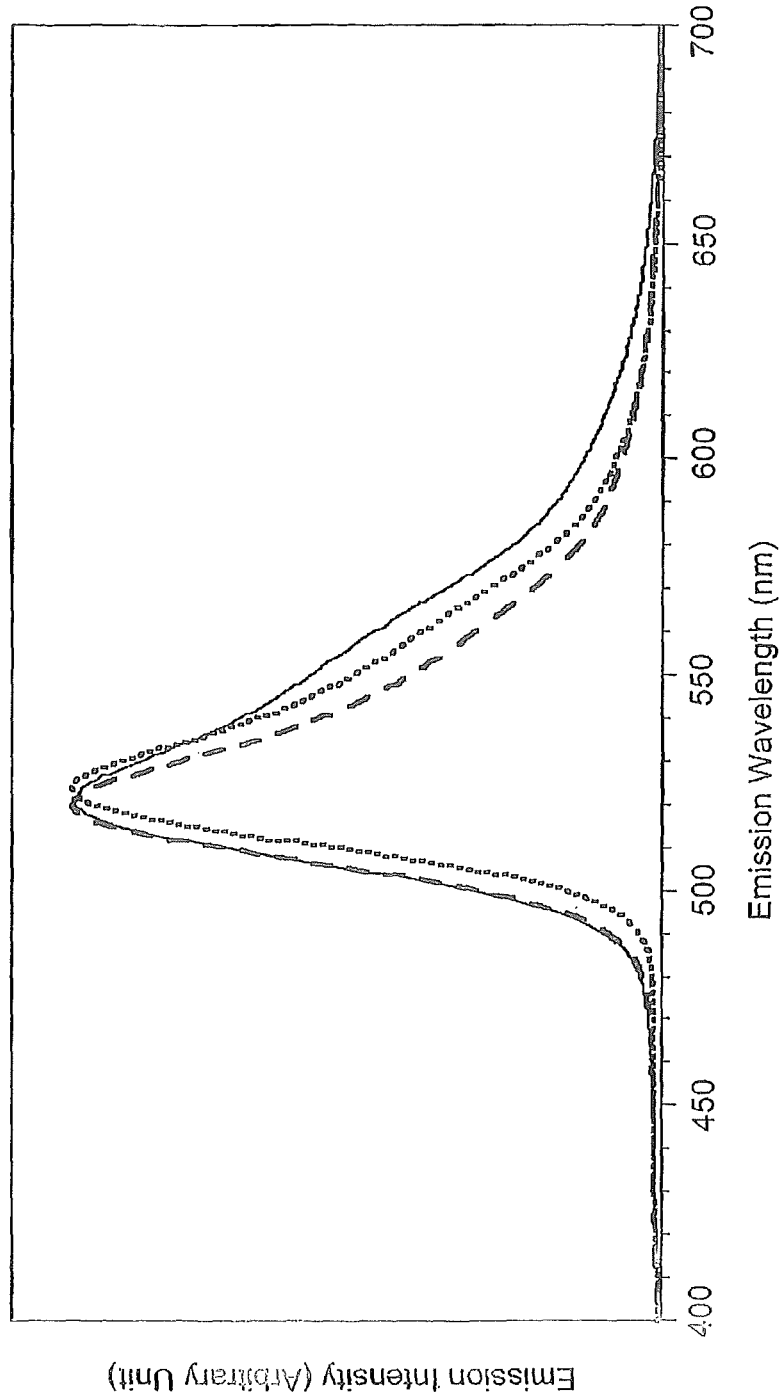
FIG. 16 is a graph of the emission spectrum obtained in Reference Example 1, and Examples 1 and 4.

FIG. 16 shows an emission spectrum of the resultant organic EL device.

Figure 21:
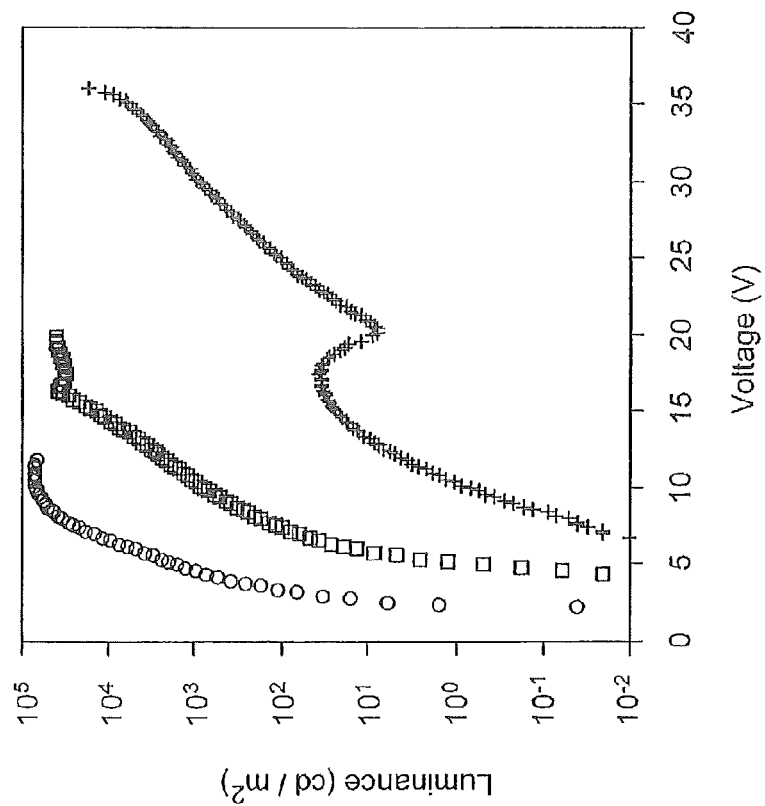
FIG. 21 is a graph of the luminance-voltage curve of the organic EL devices produced in Reference Example 1, and Examples 1 and 2.
Figure 22:
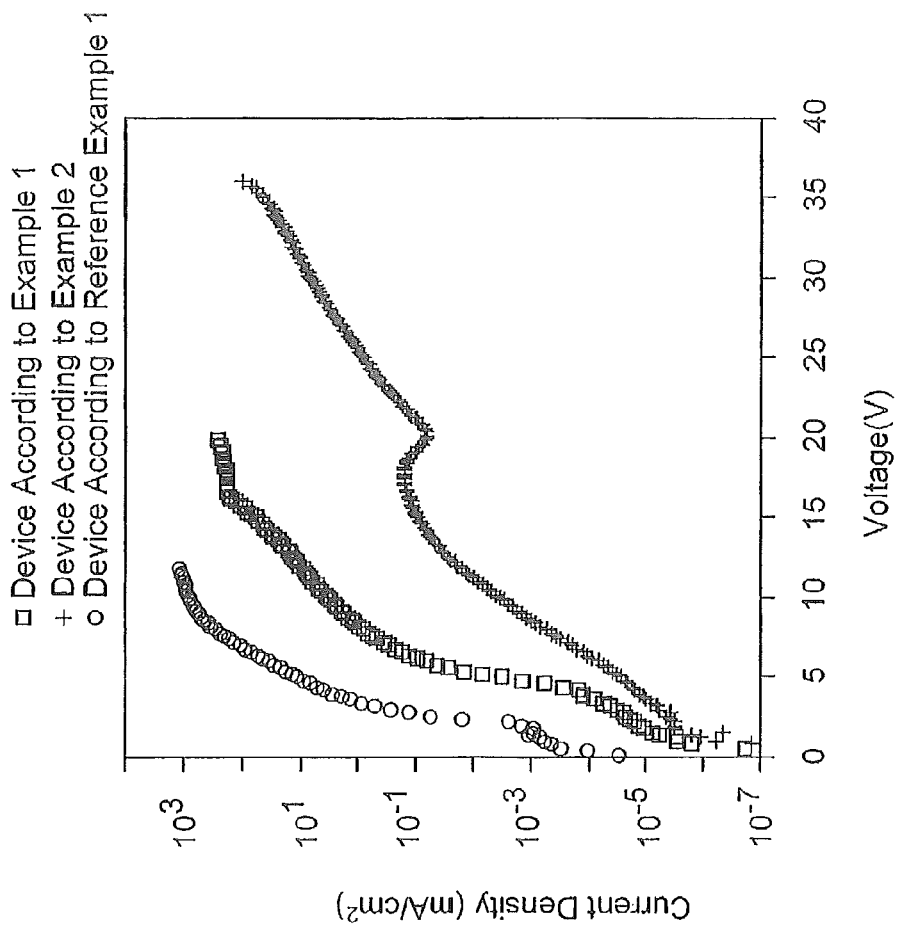
FIG. 22 is a graph of the current density-voltage curve of the EL devices produced in Reference Example 1, and Examples 1 and 2.
Figure 23:
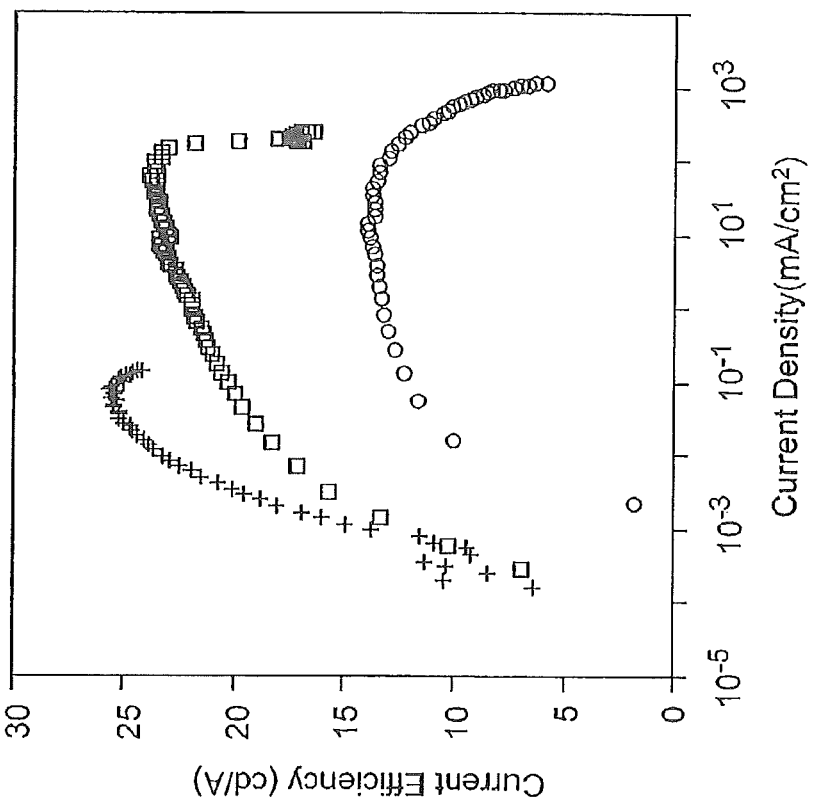
FIG. 23 is a graph of the current efficiency-current density curve of the EL devices produced in Reference Example 1, and Examples 1 and 2.

In this organic EL device, a DC voltage was applied between the anode electrode (ITO) and the cathode electrode (Al), and the characteristics of the green light emitted from the light-emissive layer (co-deposited layer of Alq and C545T) 7 were measured to obtain the results plotted in FIGS. 21, 22 and 23.

In FIGS. 21, 22 and 23, the circle symbols (○) designate the luminance (cd/m²)—voltage (v) characteristic curve, a graph of current density (mA/cm²)—voltage (v) characteristic curve and a graph of current efficiency (cd/A)—current density (mA/cm²) characteristic curve, respectively, of the EL device of Reference Example 1.

In the EL device of Reference Example 1, a voltage at which the emission was started was 2.2 volts.

Reference Example 2

Example for the Production of the Conventional Organic EL Device-Blue Light-Emitting Device A conventional organic EL device having a laminate structure shown in FIG. 11 was produced in accordance with the manner similar to Reference Example 1 as follows.

Figure 10A:
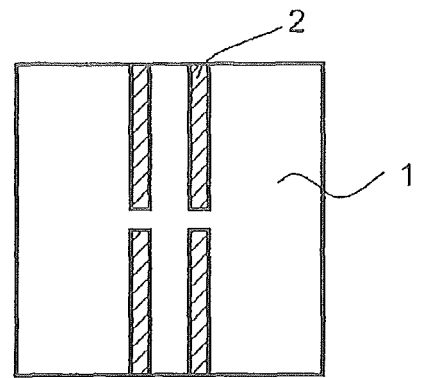
FIG. 10A shows a glass substrate on which a transparent anode electrode is coated.

A glass substrate 1 used herein includes, coated in the predetermined pattern on a surface thereof, a transparent anode electrode 2 including an ITO (indium-tin oxide, sputtered product commercially available from ASAHI GLASS) having a sheet resistance of about 20Ω/□ (see, FIG. 10A). Spiro-NPB having a hole transporting property was deposited, through a metal mask 40 for organic layer formation (see, FIG. 10B), onto the ITO-coated glass substrate 1 under vacuum of about $10^{-6}$ Torr and at a deposition rate of about 2 Å/sec to form a hole transportation layer 9 having a thickness of about 800 Å.

Spiro-DPVBi represented by the following formula:

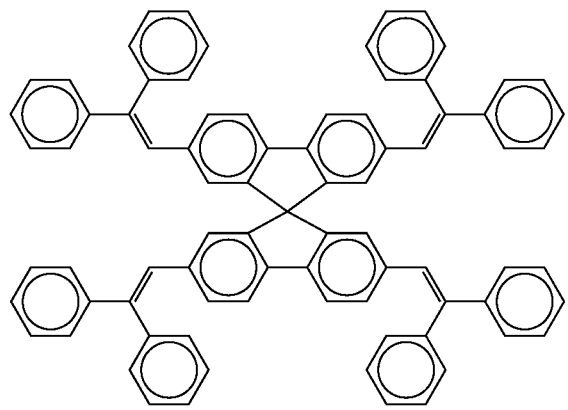

was deposited onto the hole transportation layer 9 under vacuum vapor deposition conditions to form a light-emissive layer 10 having a thickness of about 4001.

Thereafter, as in Reference Example 1, bathocuproine and metal cesium (Cs) in a molar ratio of about 1:1 were co-deposited under the controlled vacuum vapor deposition conditions to form a metal (Cs)-doped electron injection layer 11 having a thickness of about 200 Å on the light-emissive layer 10.

Figure 17:
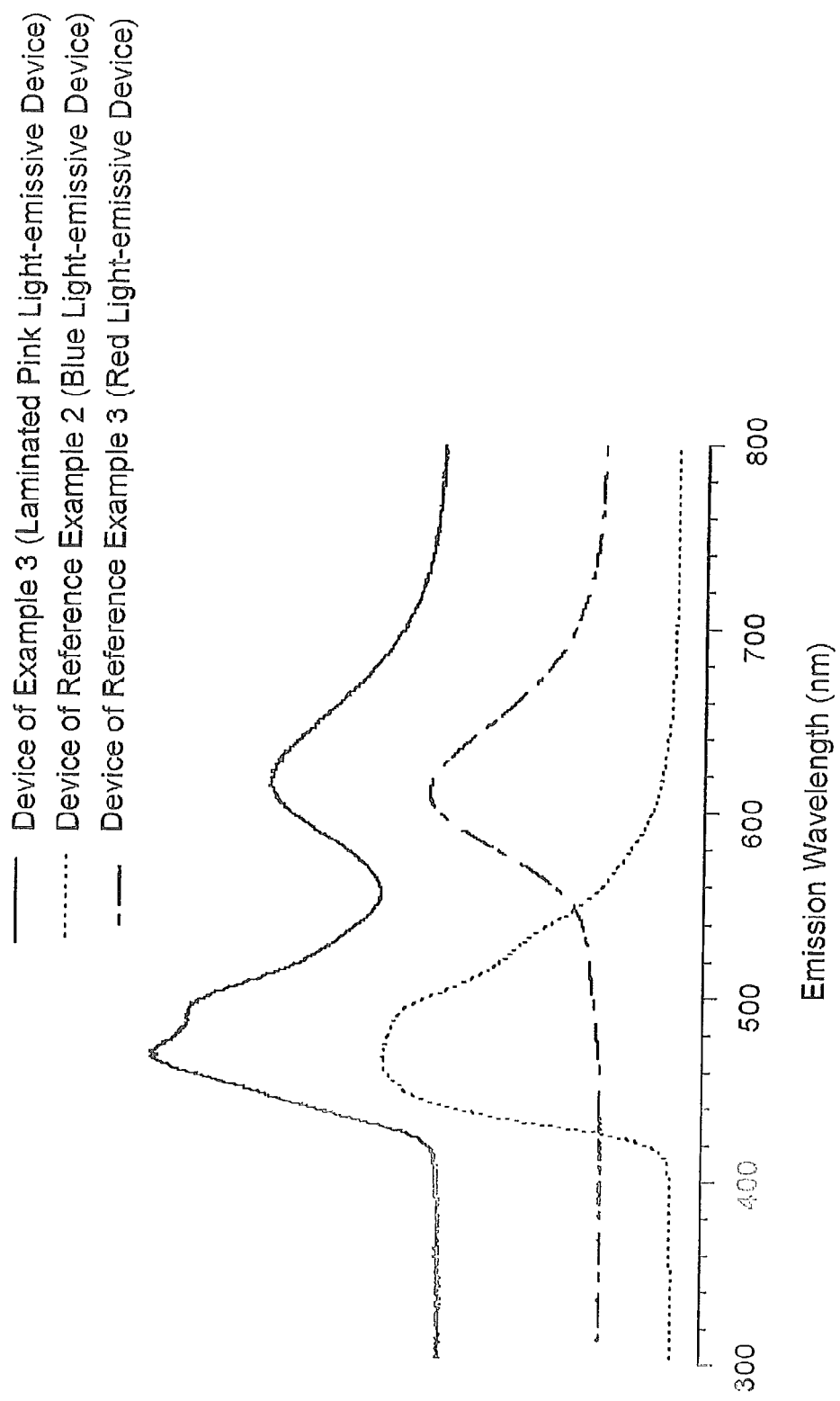
FIG. 17 is a graph of the emission spectrum obtained in Reference Examples 2 and 3, and Example 3.

Finally, aluminum (Al) was deposited through a metal mask 41 for cathode layer formation (see, FIG. 10C) at a deposition rate of about 10 Å/sec onto the electron injection layer 11 to form a cathode electrode having a thickness of about 1,000 Å. An organic EL device having a square light-emissive area of 0.2 cm (length) by 0.2 cm (width) was thus obtained (see, FIG. 10D). In FIG. 17, an emission spectrum of the resultant organic EL device (Reference Example 2) is shown as a dotted line.

Figure 24:
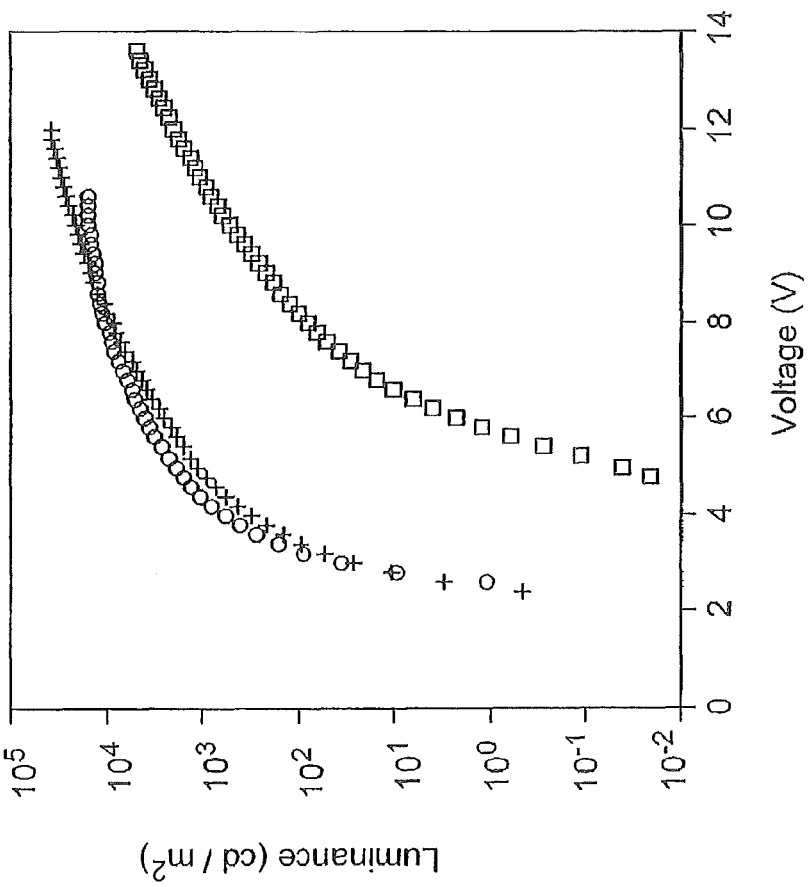
FIG. 24 is a graph of the luminance-voltage curve of the organic EL devices produced in Reference Examples 2 and 3, and Example 3.
Figure 25:
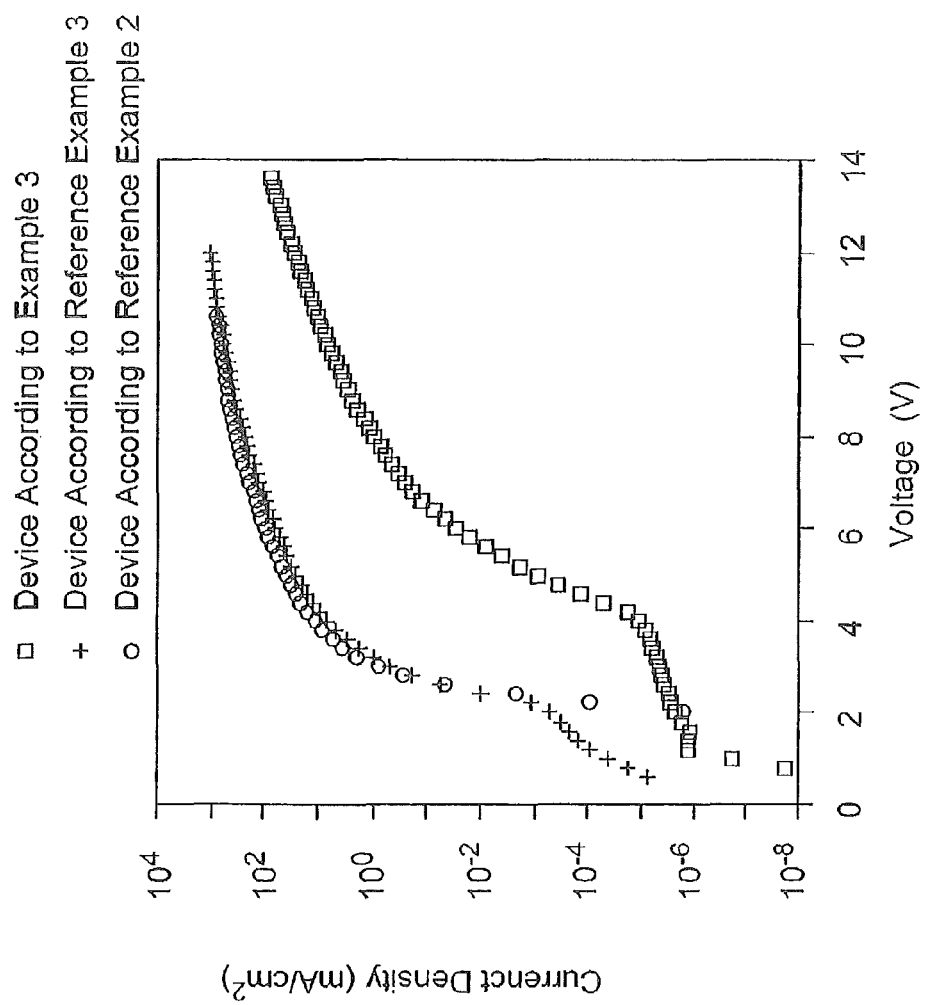
FIG. 25 is a graph of the current density-voltage curve of the EL devices produced in Reference Examples 2 and 3, and Example 3.
Figure 26:
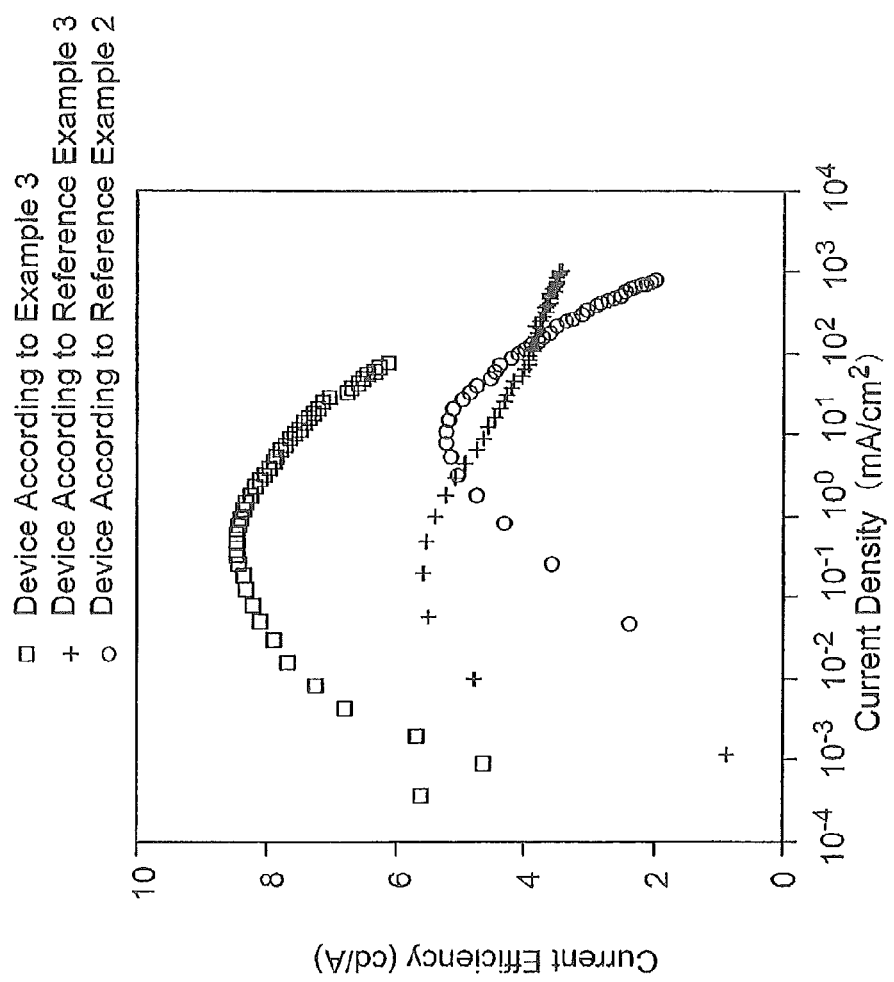
FIG. 26 is a graph of the current efficiency-current density curve of the EL devices produced in Reference Examples 2 and 3, and Example 3.

In this organic EL device, a DC voltage was applied to between the anode electrode (ITO) and the cathode electrode (Al), and the characteristics of the blue light emitted from the light-emissive layer (spiro-DPVBi) 10 were measured to obtain the results plotted in FIGS. 24, 25 and 26.

In FIGS. 24, 25 and 26, white circle symbols (○) represent a graph of luminance (cd/m²)—voltage (v) characteristic curve, a graph of current density (mA/cm²)—voltage (v) characteristic curve and a graph of current efficiency (cd/A)—current density (mA/cm²) characteristic curve, respectively, of the EL device of Reference Example 2.

In the EL device of Reference Example 2, the voltage at which the emission was started was 2.6 volts.

Reference Example 3

Figure 12:
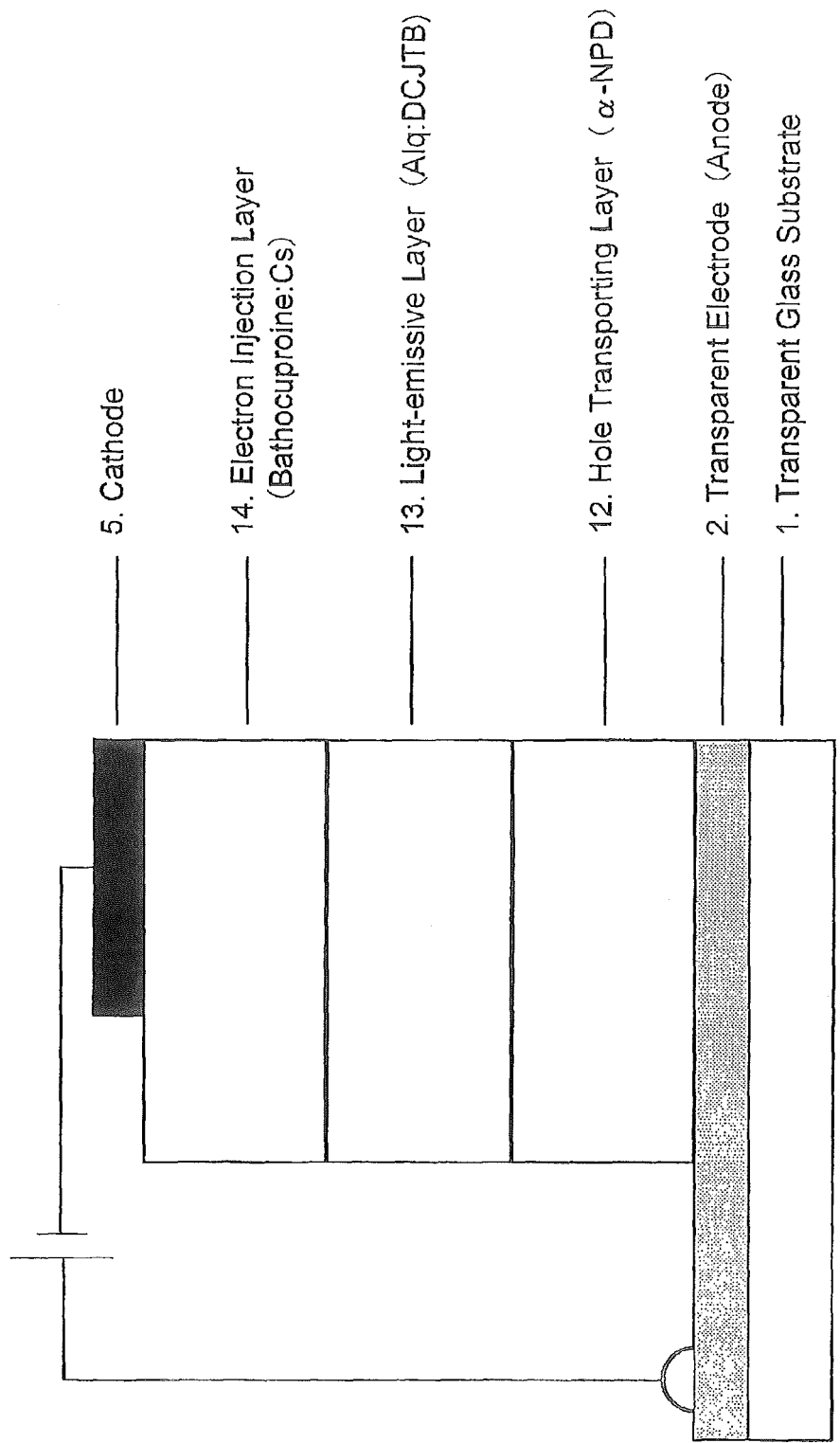
FIG. 12 is a schematic cross-sectional view illustrating a lamination structure of the organic EL device produced in Reference Example 3.

Example for the Production of the Conventional Organic EL Device-Red Light-Emitting Device A conventional organic EL device having a laminate structure shown in FIG. 12 was produced in a manner similar to Reference Example 1 as follows.

A glass substrate 1 used herein includes, coated in the predetermined pattern on a surface thereof, a transparent anode electrode 2 including an ITO (indium-tin oxide, sputtered product commercially available from ASAHI GLASS) having a sheet resistance of about 20Ω/□ (see, FIG. 10A). α-NPD having a hole transporting property was deposited, through a metal mask 40 for organic layer formation (see, FIG. 10B), onto the ITO-coated glass substrate 1 under vacuum of about $10^{-6}$ Torr and at a deposition rate of about 2 Å/sec to form a hole transportation layer 12 having a thickness of about 700 Å.

Alq and a red light-emissive fluorescent dye, "DCJTB" (trade name) commercially available from KODAK, were deposited onto the hole transportation layer 12 under the vacuum vapor deposition conditions to form a light-emissive layer 13 having a thickness of about 400 Å. Each deposition rate was adjusted so that the resulting light-emissive layer 13 contains the fluorescent dye in a concentration of about 1% by weight.

Thereafter, as in Reference Example 1, bathocuproine and metal cesium (Cs) in a molar ratio of about 1:1 were co-deposited under the controlled vacuum vapor deposition conditions to form a metal (Cs)-doped electron injection layer 14 having a thickness of about 200 Å on the light-emissive layer 13.

Finally, aluminum (Al) was deposited through a metal mask 41 for cathode layer formation (see, FIG. 10C) at a deposition rate of about 10 Å/sec onto the electron injection layer 11 to form a cathode electrode having a thickness of about 1,000 Å. An organic EL device having a square light-emissive area of 0.2 cm (length) by 0.2 cm (width) was thus obtained (see, FIG. 10D).

In FIG. 17, an emission spectrum of the resultant organic EL device (Reference Example 3) is shown with a chain line.

In this organic EL device, a DC voltage was applied to between the anode electrode (ITO) and the cathode electrode (Al), and the characteristics of the red light emitted from the light-emissive layer (co-deposited layer of Alq and DCJTB) 13 were measured to obtain the results plotted in FIGS. 24, 25 and 26.

In FIGS. 24, 25 and 26, plus symbols (+) represent a graph of luminance (cd/m²)—voltage (v) characteristic curve, a graph of current density (mA/cm²)—voltage (v) characteristic curve and a graph of current efficiency (cd/A)—current density (mA/cm²) characteristic curve, respectively, of the EL device (Reference Example 3).

In the EL device of Reference Example 3, a voltage at which the emission was started was 2.2 volts.

Example 1

Figure 13:
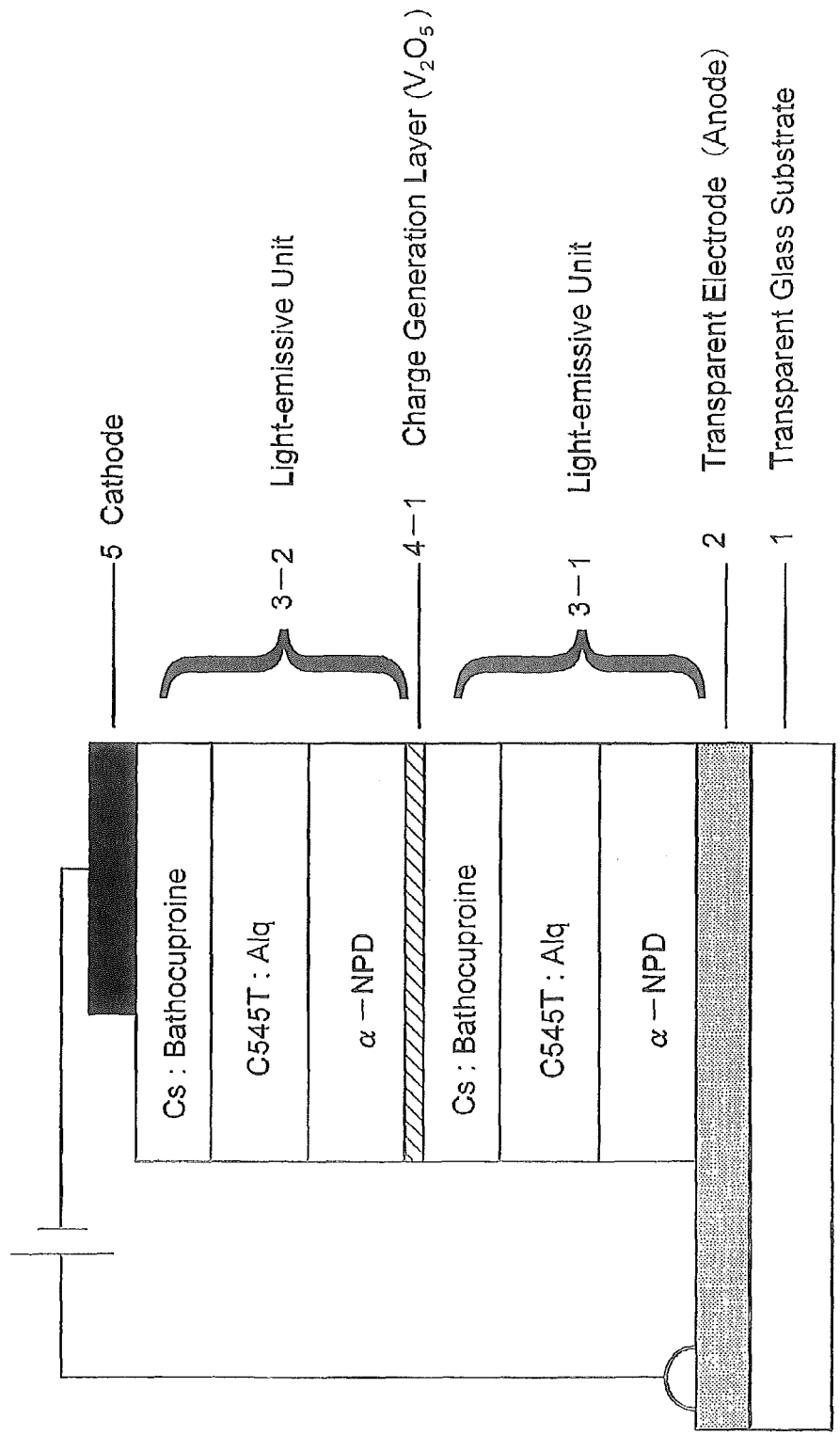
FIG. 13 is a schematic cross-sectional view illustrating a lamination structure of the organic EL device produced in Example 1.

Example for the Production of the Organic EL Device Having a Charge Generation Layer Including $V_2O_5$, Vanadium Pentaoxide The organic EL device according to the present invention having a laminate structure shown in FIG. 13 was produced as follows.

In accordance with the manner and order described in Reference Example 1, a light-emissive unit 3-1 was deposited through a metal mask 40 for organic layer formation (see, FIG. 10B) on an ITO pattern-coated glass substrate 1 shown in FIG. 10A. Namely, a 600 Å-thick α-NPD, a 400 Å-thick layer including Alq:C545T=100:1 (weight ratio), and a 200 Å-thick mixed layer including bathocuproine and metal cesium (Cs) were sequentially deposited.

Subsequently, $V_2O_5$ (vanadium pentaoxide) was deposited onto the metal-doped layer at a deposition rate of about 2 Å/sec to form a charge generation layer 4-1 having a thickness of about 100 Å. The formation of the charge generation layer 4-1 was also carried out in the presence of the metal mask 40 for organic layer formation (see, FIG. 10B).

Thereafter, while the metal mask 40 for organic layer formation (FIG. 10B) is still on the glass substrate 1, the above-described step was again repeated to form a light-emissive unit 3-2. Namely, a 600 Å-thick α-NPD, a 400 Å-thick layer including Alq:C545T=100:1 (weight ratio), and a 200 Å-thick mixed layer including bathocuproine and a metal cesium (Cs) were sequentially deposited.

Finally, aluminum (Al) was deposited through a metal mask 41 for cathode layer formation (see, FIG. 10C) at a deposition rate of about 10 Å/sec onto the light-emissive unit 3-2 to form a cathode electrode 5 having a thickness of about 1,000 Å. An organic EL device having a square light-emissive area of 0.2 cm (length) by 0.2 cm (width) was thus obtained (see, FIG. 10D).

In this organic EL device, a DC voltage was applied to between the anode electrode (ITO) and the cathode electrode (Al), and the characteristics of the green light emitted from the light-emissive layer (co-deposited layer of Alq and C545T) were measured to obtain the results plotted in FIGS. 21, 22 and 23. In FIGS. 21, 22 and 23, white square symbols (□) represent a graph of luminance (cd/m$^2$)—voltage (v) characteristic curve, a graph of current density (mA/cm$^2$)—voltage (v) characteristic curve, and a graph of current efficiency (cd/A)—current density (mA/cm$^2$) characteristic curve, respectively, of the EL device of Example 1.

In this EL device, a voltage at which the emission was started was 4.4 volts, i.e., exactly 2 times of the voltage observed in Reference Example 1.

As can appreciated from the above results, the organic EL device which includes two light-emissive units, each partitioned with a charge generation layer, achieves an increased maximum current efficiency (and thus the quantum efficiency) by about 2 times in comparison with the organic EL device of Reference Example 1.

In the EL device of Example 1, it is considered that an oxidation-reduction reaction was induced between the molecules of vanadium pentaoxide ($V_2O_5$) and α-NPD, an arylamine compound which acts as a hole transporting molecule, to form a charge transfer complex ($V_2O_5^-$+α-NPD$^+$).

Namely, an interfacial surface between the vanadium pentaoxide ($V_2O_5$) layer and the α-NPD layer acts as a charge generation layer.

In FIG. 16, an emission spectrum of the resultant organic EL device is shown by a chain line. Referring to the plotted emission spectrum, it is observed that the spectrum is substantially the same as that of Reference Example 1, however, a full width at half maximum of the spectrum is slightly narrowed in comparison with that of Reference Example 1. It therefore can be concluded that this is due to the generated interference effect. Namely, an interference effect was generated in the two light-emissive units because a light emitted from the firstly formed light-emissive unit 3-1 was reflected on the cathode, and the reflected light had a phase which substantially corresponds to a phase of the light directly projected in the direction of the substrate from the emissive site.

Example 2

Figure 14:
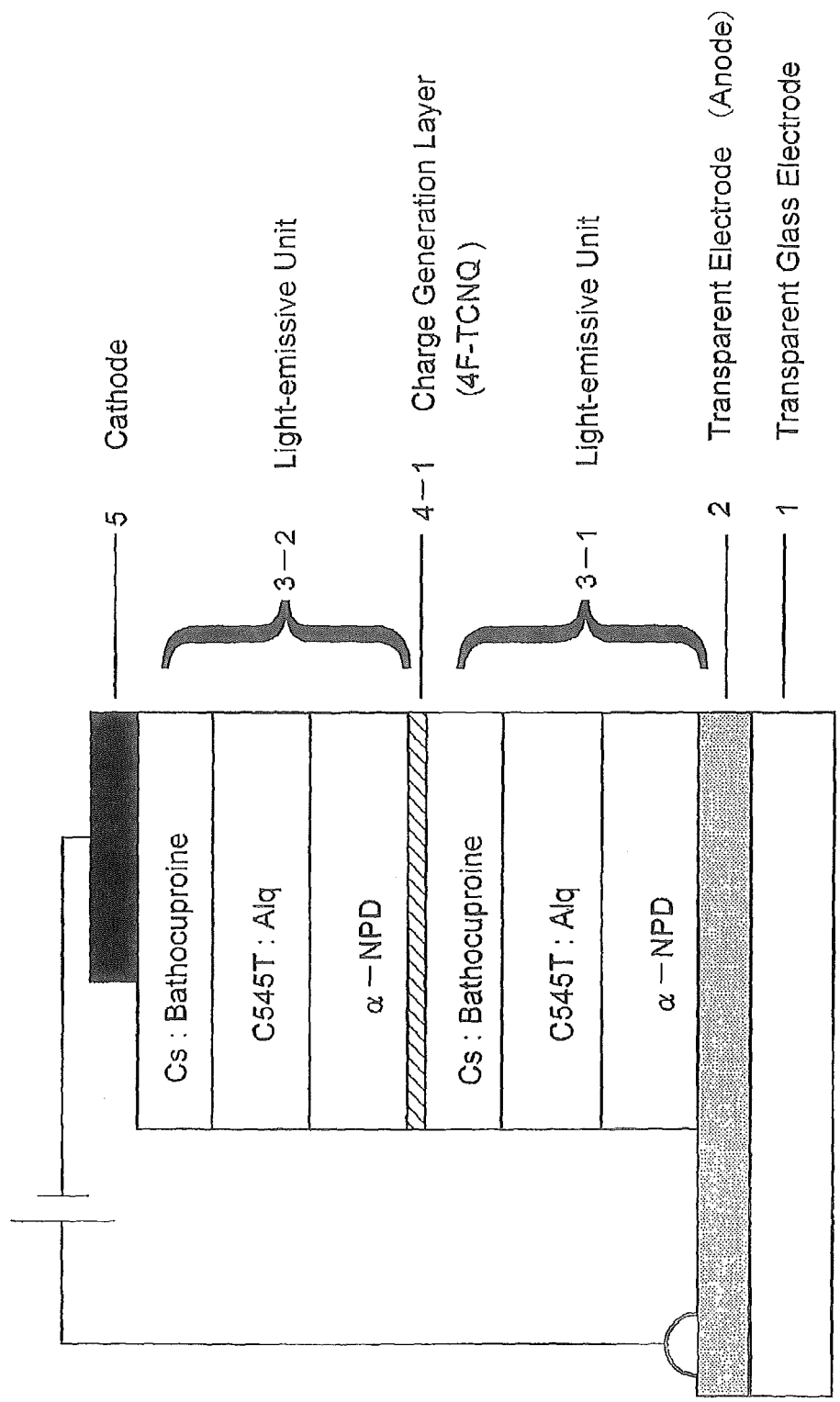
FIG. 14 is a schematic cross-sectional view illustrating a lamination structure of the organic EL device produced in Example 2.

Example for the Production of the Organic EL Device Having a Charge Generation Layer Consisting Only of an Organic Compound The organic EL device according to the present invention having a laminate structure shown in FIG. 14 was produced as follows.

In accordance with the manner which is substantially the same as that described in Reference Example 1, a light-emissive unit 3-1 was deposited through a metal mask 40 for organic layer formation (see, FIG. 10B) on an ITO pattern-coated glass substrate 1 shown in FIG. 10A. Namely, a 700 Å-thick α-NPD, a 400 Å-thick layer including Alq C545T=100:1 (weight ratio), and a 200 Å-thick mixed layer including bathocuproine and metal cesium (Cs) were sequentially deposited.

4F-TCNQ represented by the following formula:

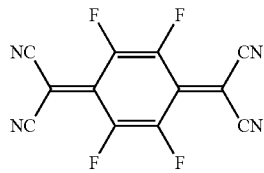 [SMILES: N#CC(C#N)=c1c(F)c(F)c(=C(C#N)C#N)c(F)c1F]

was deposited onto the metal-doped layer at a deposition rate of about 1 Å/sec to form a charge generation layer 4-1 having a thickness of about 20 Å. 2-TNATA (product of BANDO CHEMICAL) was deposited onto the charge generation layer 4-1 at a deposition rate of about 1 Å/sec to obtain a layer thickness of about 50 Å.

Figure 10B:
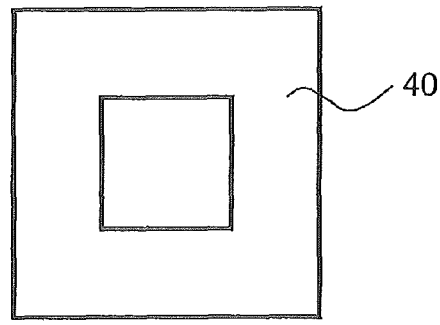
FIG. 10B shows a construction of a metallic mask for organic layer formation.
Figure 10C:
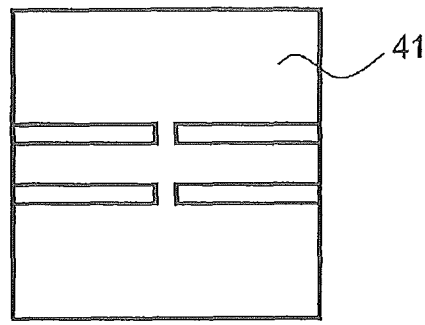
FIG. 10C shows a construction of a metallic mask for cathode electrode formation.
Figure 10D:
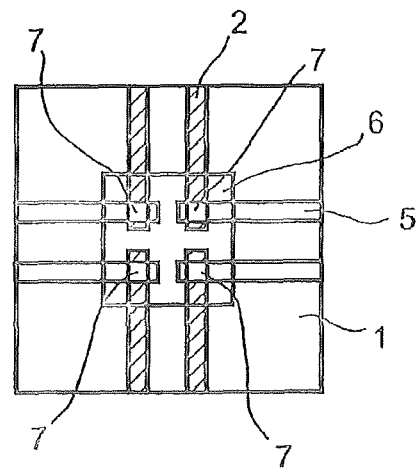
FIG. 10D shows schematic view illustrating a construction of the organic EL device.

The formation of the charge generation layer 4-1 was also carried out in the presence of the metal mask 40 for organic layer formation (see, FIG. 10B).

Thereafter, while the metal mask 40 for organic layer formation (FIG. 10B) is still on the glass substrate 1, the above-described step was again repeated to form a light-emissive unit 3-2. Namely, a 700 Å-thick α-NPD, a 400 Å-thick layer including Alq:C545T=100:1 (weight ratio), and a 200 Å-thick mixed layer including bathocuproine and a metal cesium (Cs) were sequentially deposited.

Finally, aluminum (Al) was deposited through a metal mask 41 for cathode layer formation (see, FIG. 10C) at a deposition rate of about 10 Å/sec onto the light-emissive unit 3-2 to form a cathode electrode 5 having a thickness of about 1,000 Å. The organic EL device having a square light-emissive area of 0.2 cm (length) by 0.2 cm (width) was thus obtained (see, FIG. 10D).

In this organic EL device, a DC voltage was applied between the anode electrode (ITO) and the cathode electrode (Al), and the characteristics of the green light emitted from the light-emissive layer (co-deposited layer of Alq and C545T) were measured to obtain the results plotted in FIGS. 21, 22 and 23.

In FIGS. 21, 22 and 23, the plus symbols represent a graph of luminance ($cd/m^2$)—voltage (v) characteristic curve, a graph of current density ($mA/cm^2$)—voltage (v) characteristic curve and a graph of current efficiency (cd/A)—current density ($mA/cm^2$) characteristic curve, respectively, of the EL device of Example 2.

In the EL device of Example 2, it is considered that a charge transfer complex (4F-TCNQ-+2-TNATA+) was formed between the two organic molecules, i.e., 4F-TCNQ which is a Lewis acid and 2-TNATA which is a hole transporting arylamine molecule. Namely, an interfacial surface between the 4F-TCNQ layer and the 2-TNATA layer acts as a charge generation layer.

Furthermore, in this EL device, it was observed that the current efficiency was gradually reduced from a luminance of about 30 $cd/m^2$ (current density=0.12 $mA/cm^2$), but the maximum current efficiency of about 25.6 cd/A was obtained at a current density range of up to about 0.1 $mA/cm^2$. The maximum current efficiency of about 25.6 cd/A is a value which could not be obtained in the conventional organic EL devices having only one light-emissive unit, and proves that the charge generation layer can be formed by using only an organic compound.

Example 3

Figure 15:
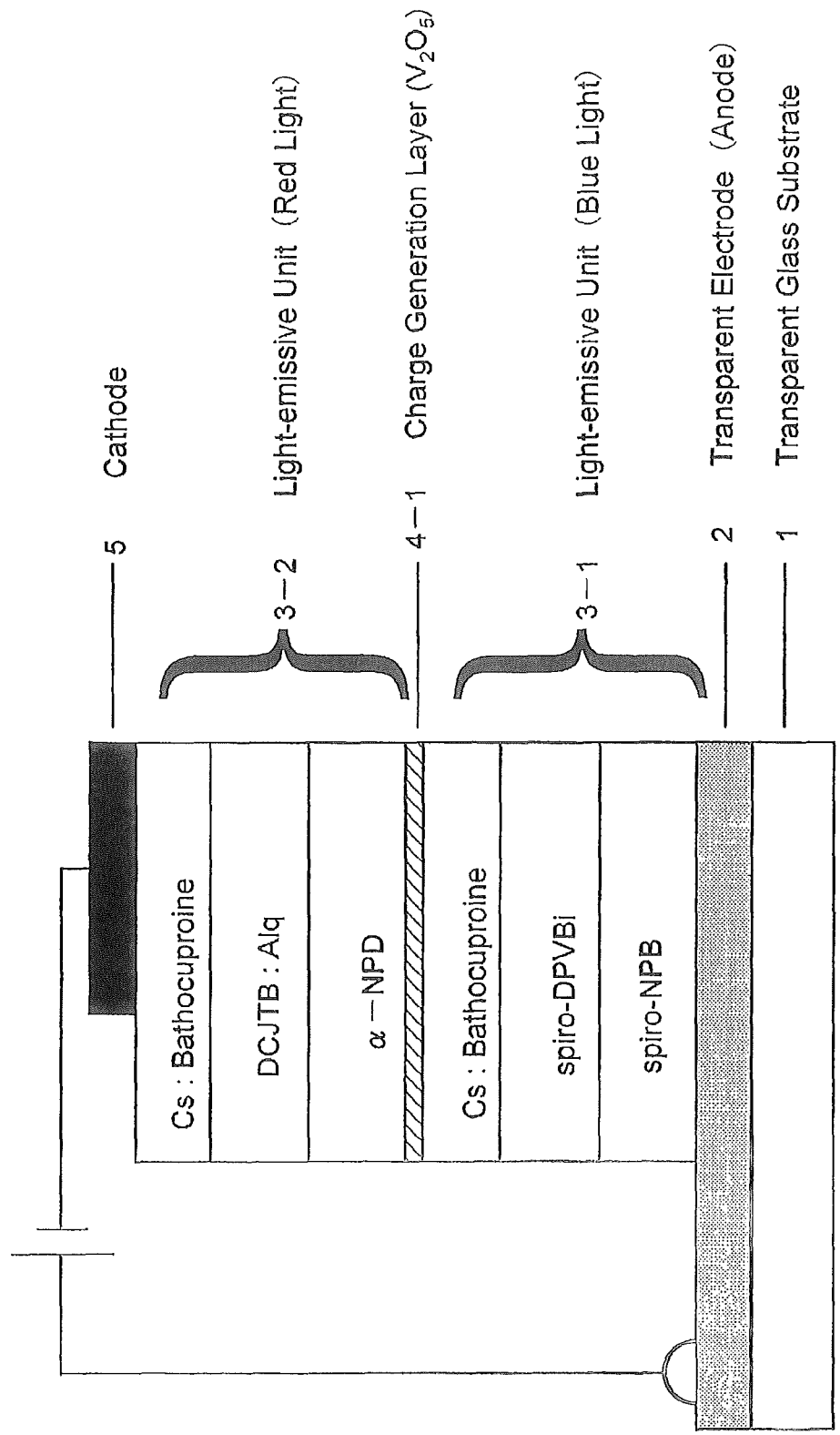
FIG. 15 is a schematic cross-sectional view illustrating a lamination structure of the organic EL device produced in Example 3.

Example for the Production of the Organic EL Device Having Two Light-Emissive Units Having Different Emission Spectrums The organic EL device according to the present invention having a laminate structure shown in FIG. 15 was produced as follows.

As in Reference Example 1, a glass substrate 1 includes, coated in a predetermined pattern on a surface thereof, a transparent anode electrode 2 including an ITO (indium-tin oxide, sputtered product commercially available from ASAHI GLASS) having a sheet resistance of about 20Ω/□ (see, FIG. 10A). On the ITO pattern-coated glass substrate 1, in the same order as in Reference Example 2, spiro-NPB having a hole transporting property (product of COVION) was deposited through a metal mask 40 for organic layer formation (see, FIG. 10B) onto the ITO-coated glass substrate 1 under vacuum of about $10^{-6}$ Torr and at a deposition rate of about 2 Å/sec to form a hole transportation layer of the light-emissive unit 3-1 having a thickness of about 800 Å.

Subsequently, spiro-DPVBi (product of COVION) was deposited onto the hole transportation layer at a deposition rate of about 2 Å/sec to form a blue light-emissive layer of the light-emissive unit 3-1 having a thickness of about 400 Å, followed by depositing a 200 Å-thick mixed layer including bathocuproine and a metal cesium (Cs).

Subsequently, as in Example 1, $V_2O_5$ (vanadium pentaoxide) was deposited onto the mixed layer including bathocuproine and Cs at a deposition rate of about 2 Å/sec to form a charge generation layer 4-1 having a thickness of about 100 Å. The formation of the charge generation layer 4-1 was also carried out in the presence of the metal mask 40 for organic layer formation (see, FIG. 10B).

Thereafter, as in Reference Example 3, α-NPD was deposited at a layer thickness of about 700 Å to form a hole transportation layer of the light-emissive unit 3-2. Subsequently, Alq and a red light-emissive fluorescent dye, "DCJTB" (KODAK), were deposited onto the hole transportation layer to form a red light-emissive layer having a thickness of about 400 Å. Each deposition rate was adjusted so that the resulting red light-emissive layer contains the fluorescent dye in a concentration of about 1% by weight. Subsequently, as in the manner described above, a 200 Å-thick mixed layer including bathocuproine and Cs was deposited.

Finally, aluminum (Al) was deposited through a metal mask 41 for cathode layer formation (see, FIG. 10C) at a deposition rate of about 10 Å/sec onto the mixed layer of bathocuproine and Cs to form a cathode electrode 5 having a thickness of about 1,000 Å. The organic EL device having a square light-emissive area of 0.2 cm (length) by 0.2 cm (width) was thus obtained (see, FIG. 10D).

Figure 39A:
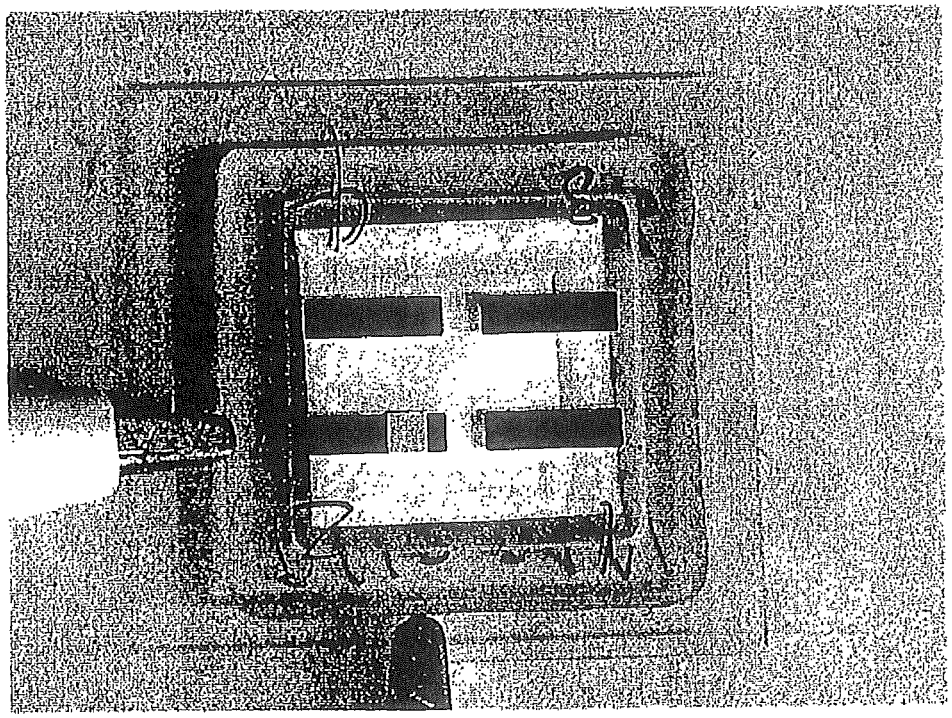
FIG. 39A is a photograph showing an emission state in the organic EL device produced in Example 3.
Figure 39B:
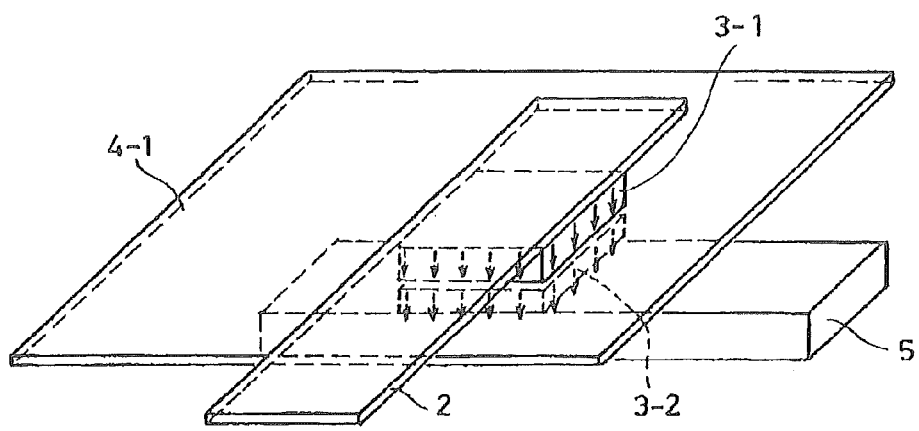
FIG. 39B is a schematic cross-sectional view illustrating a lamination structure of the organic EL device produced in Example 3.

In FIG. 17, an emission spectrum of the organic EL device obtained in Example 3 is shown with a solid line. In this organic EL device, a DC voltage was applied to between the anode electrode (ITO) and the cathode electrode (Al). As a result, a light emission of the mixed color of blue and red (pink-colored emission) could be obtained from the two light-emissive layers. FIG. 39A is a photograph showing an emission state in this device (FIG. 39B).

Subsequently, the characteristics of the device were measured to obtain the results plotted in FIGS. 24, 25 and 26. In these drawings, white square symbols (□) represent a graph of luminance ($cd/m^2$)—voltage (v) characteristic curve, a graph of current density ($mA/cm^2$)—voltage (v) characteristic curve, and a graph of current efficiency (cd/A) current density ($mA/cm^2$) characteristic curve, respectively, of the EL device of Example 3.

In the EL device of Example 3, a voltage at which the emission was started was about 4.8 volts. Namely, the starting voltage of about 4.8 volts is a sum of the starting voltage (2.6 volts) of the device of Reference Example 2 and the starting voltage (2.2 volts) of the device of Reference Example 3.

Furthermore, in the EL device of Example 3, as in Example 1, it is considered that an oxidation-reduction reaction was induced between the molecules of vanadium pentaoxide ($V_2O_5$) and α-NPD, an arylamine compound which acts as a hole transporting molecule, to form a charge transfer complex ($V_2O_5^-$+α-NPD$^+$). Namely, an interfacial surface between the vanadium pentaoxide ($V_2O_5$) layer and the α-NPD layer acts as a charge generation layer.

Example 4

Figure 18:
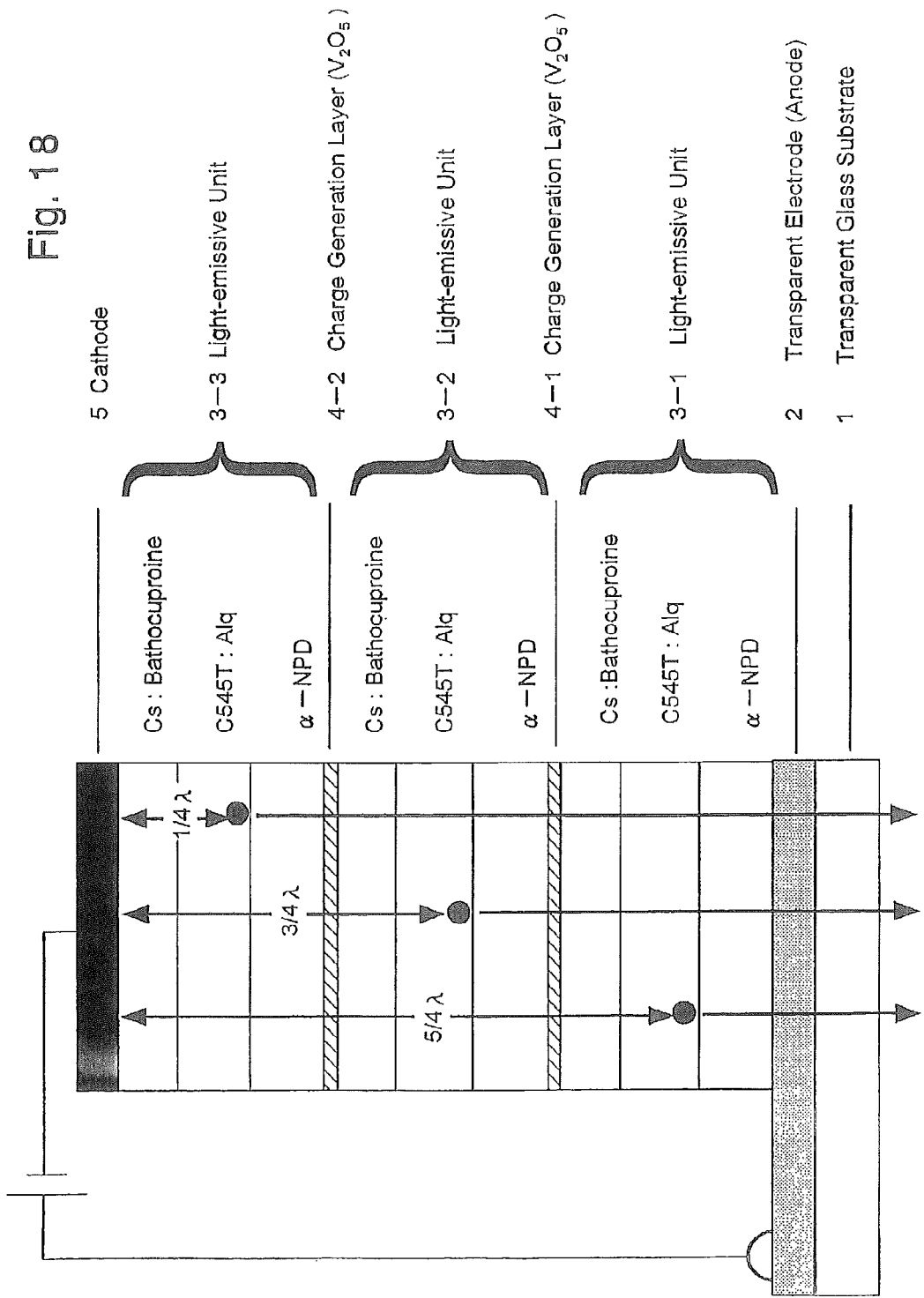
FIG. 18 is a schematic cross-sectional view illustrating a lamination structure of the organic EL device produced in Example 4.

Example for the Production of the Organic EL Device Having Three Light-Emissive Units; Experiments for Optimizing the Optical Path Length, a Distance from Each Light-Emissive Site to a Reflective Cathode The organic EL device according to the present invention having a laminate structure shown in FIG. 18 was produced as follows.

Three sheets of the ITO pattern-coated glass substrate 1 were provided. In, accordance with the manner and order described in Reference Example 1, a light-emissive unit 3-1 was deposited through a metal mask 40 for organic layer formation (see, FIG. 10B) on the ITO pattern-coated glass substrate 1 shown in FIG. 10A. Namely, a 700 Å-thick α-NPD, a 600 Å-thick layer including Alq:C545T=100:1 (weight ratio), and a 100 Å-thick mixed layer including bathocuproine and a metal cesium (Cs) were sequentially deposited on each ITO pattern-coated glass substrate 1.

Subsequently, $V_2O_5$ (vanadium pentaoxide) was deposited onto the metal-doped layer at a deposition rate of about 2 Å/sec to form a charge generation layer 4-1 having a thickness of about 300 Å. The formation of the charge generation layer 4-1 was also carried out in the presence of the metal mask 40 for organic layer formation (see, FIG. 10B).

Thereafter, while the metal mask 40 for organic layer formation (FIG. 10B) is still on the glass substrate 1, the above-described step was again repeated to form a light-emissive unit 3-2 and a light-emissive layer 3-3. Note, in this example, that to ascertain the optimum conditions for an optical path length from each light-emissive site to a reflective cathode, a layer thickness of the hole transportation layer including α-NPD was varied with intention to obtain three different cells having the hole transportation layer of the thickness of about 300, 500 or 700 Å.

Namely, a 300, 500 or 700 Å-thick α-NPD, a 600 Å-thick layer including Alq:C545T=100:1 (weight ratio), and a 100 Å-thick mixed layer including bathocuproine and a metal cesium (Cs) were sequentially deposited on each substrate to form a light-emissive unit 3-2. Subsequently, $V_2O_5$ (vanadium pentaoxide) was deposited at a deposition rate of about 2 Å/sec to form a charge generation layer 4-2 having a thickness of about 300 Å.

After formation of the charge generation layer 4-2, the above-described process was again repeated. That is, a 300, 500, or 700 Å-thick α-NPD, a 600 Å-thick layer including Alq:C545T=100:1 (weight ratio), and a 100 Å-thick mixed layer including bathocuproine and a metal cesium (Cs) were sequentially deposited on the charge generation layer 4-2 to form a light-emissive unit 3-3.

Finally, aluminum (Al) was deposited through a metal mask 41 for cathode layer formation (see, FIG. 10C) at a deposition rate of about 10 Å/sec onto the light-emissive unit 3-3 to form a cathode electrode 5 having a thickness of about 1,000 Å. The organic EL device having a square light-emissive area of 0.2 cm (length) by 0.2 cm (width) was thus obtained (see, FIG. 10D).

Figure 27:
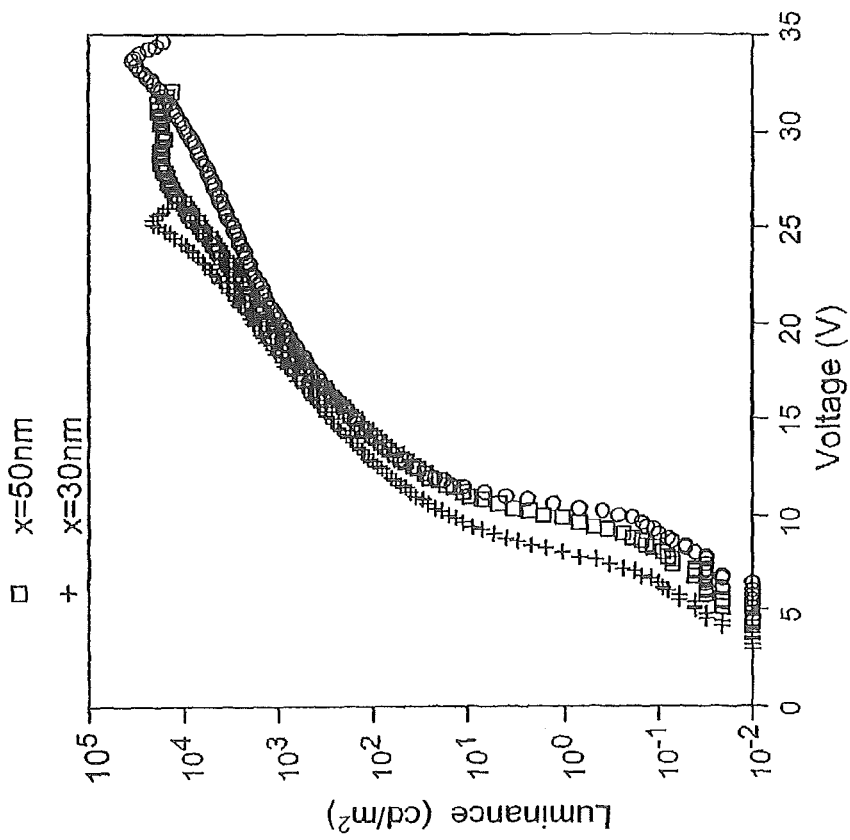
FIG. 27 is a graph of the luminance-voltage curve of three organic EL devices produced in Example 4.
Figure 28:
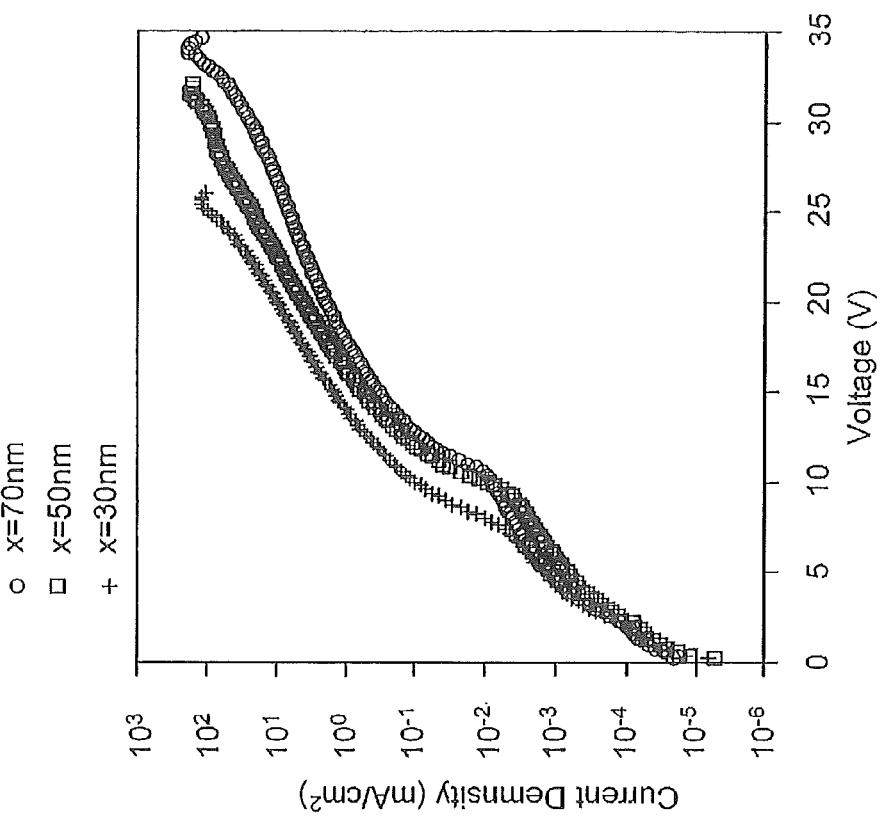
FIG. 28 is a graph of the current density-voltage curve of three EL devices produced in Example 4.

In the resulting organic EL device, a DC voltage was applied to between the anode electrode (ITO) and the cathode electrode (Al) to measure the characteristics of the green light emitted from the light-emissive layer (co-deposited layer of Alq and C545T). The results plotted in FIGS. 27, 28 and 29 were obtained. In these figures, the symbols ○, □ and + each represents a graph of the luminance ($cd/m^2$)—voltage (v) characteristic curve, a graph of the current density (mA/$cm^2$)—voltage (v) characteristic curve, and a graph of the current efficiency (cd/A)—current density ($mA/cm^2$) characteristic curve, respectively, of each of the EL devices having the three different thickness described above.

Figure 29:
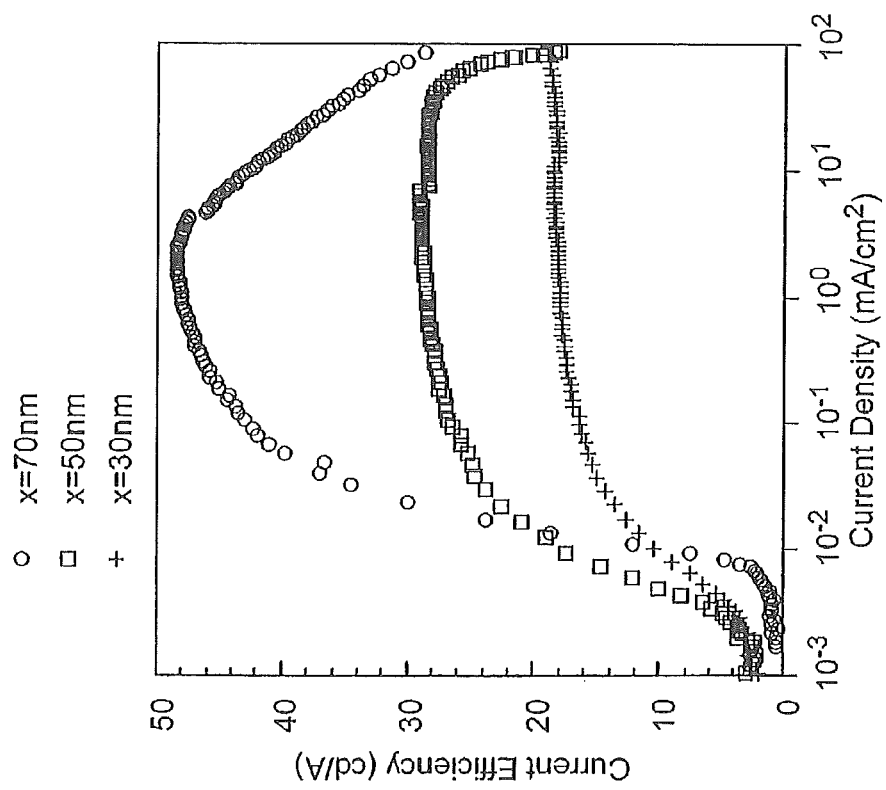
FIG. 29 is a graph of the current efficiency-current density curve of three EL devices produced in Example 4.

As shown in FIG. 29, the EL devices having the three different thickness each have a largely varied current efficiency (cd/A). In the devices having the light-emissive units 3-2 and 3-3 having a thickness of about 700 Å in the hole transportation layer, a maximum current density exceeding about 48 cd/A was obtained, while in the devices including the light-emissive units 3-2 and 3-3 having a thickness of about 300 or 500 Å in the hole transportation layer the current density obtained was only about 18 or 28 cd/A.

The EL device including the light-emissive units 3-2 and 3-3 having a thickness of about 700 Å in the hole transportation layer show that they have a current efficiency of about 16 cd/A (48/3 cd/A) per a light-emissive unit, and thus they represent the optimized examples in which in all of the three light-emissive sites, an optical path length (product of a real layer thickness and an index of refraction) from the light-emissive site to the Al cathode (light reflective cathode) is always approximately an odd-numbered times a quarter wavelength of light, i.e., in this example, the layer thickness is ¼ wavelength, ¾ wavelength and ⁵⁄₄ wavelength of the emission wavelength, respectively, from an Al cathode side of the device.

Figure 19:
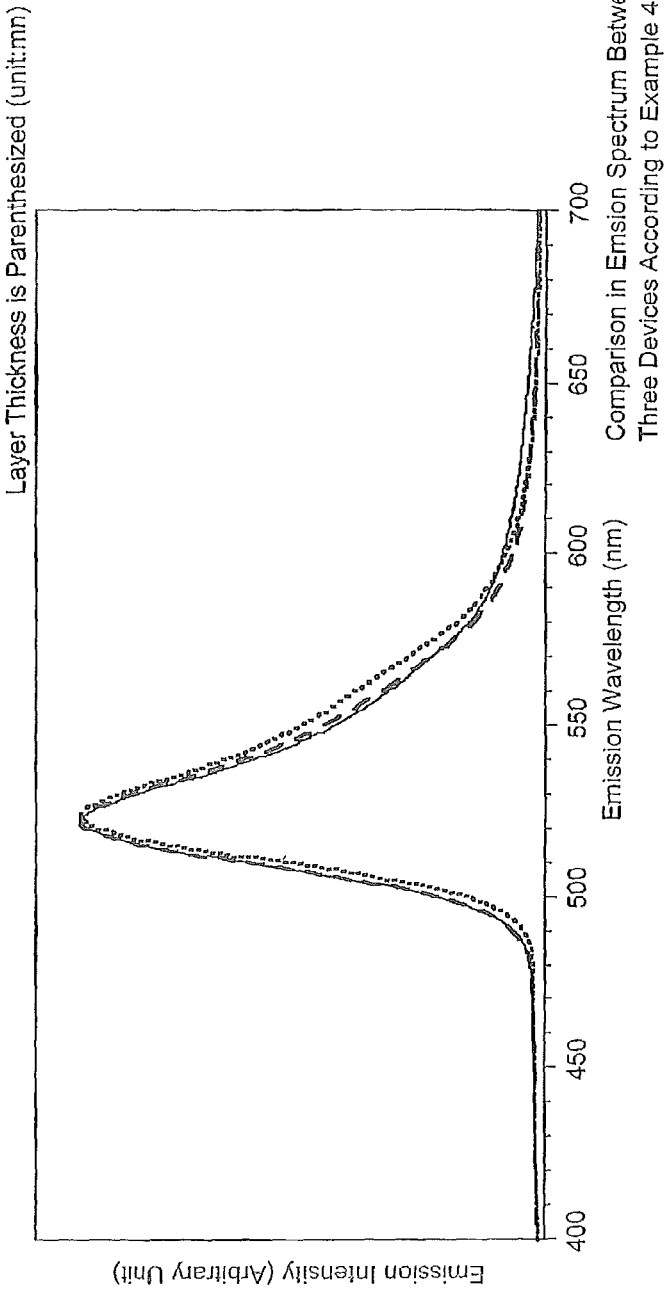
FIG. 19 is a graph of the emission spectrum of three EL devices produced in Example 4.

An emission spectrum of each of the three organic EL devices obtained in Example 4 is shown in FIG. 19. Furthermore, the emission spectrum of the device showing the maximum current efficiency (48 cd/A), selected from all the emission spectrums of the devices of Example 4, is also plotted in FIG. 16 for the comparison with the spectrum of the device (one light-emissive unit) of Reference Example 1 and the spectrum of the device (two light-emissive units) of Example 1.

Example 5

Example for the Production of the Organic EL Device Including Two Light-Emissive Units Having Different Emission Spectrums; Experiments for Optimizing the Optical Path Length, a Distance from Each Light-Emissive Site to a Reflective Electrode Three sheets of the ITO pattern-coated glass substrate were provided, and in accordance with the process which is substantially the same as that of Example 3, a blue light-emissive unit and a red light-emissive unit were deposited through a $V_2O_5$ (vanadium pentaoxide) of the charge-generation layer 4-1 with the proviso that, in this example, for the purpose of ascertaining the optimum conditions for an optical path length of from a blue light-emissive site of the light-emissive unit 3-1 to the light reflective electrode, a layer thickness of the hole transportation layer including α-NPD of the light-emissive unit 3-2 was varied with intention to obtain three different cells having the hole transportation layer of the thickness of about 300, 500 or 700 Å. Other layer deposition conditions and measurement conditions are with the same as those of Example 3.

Figure 30:
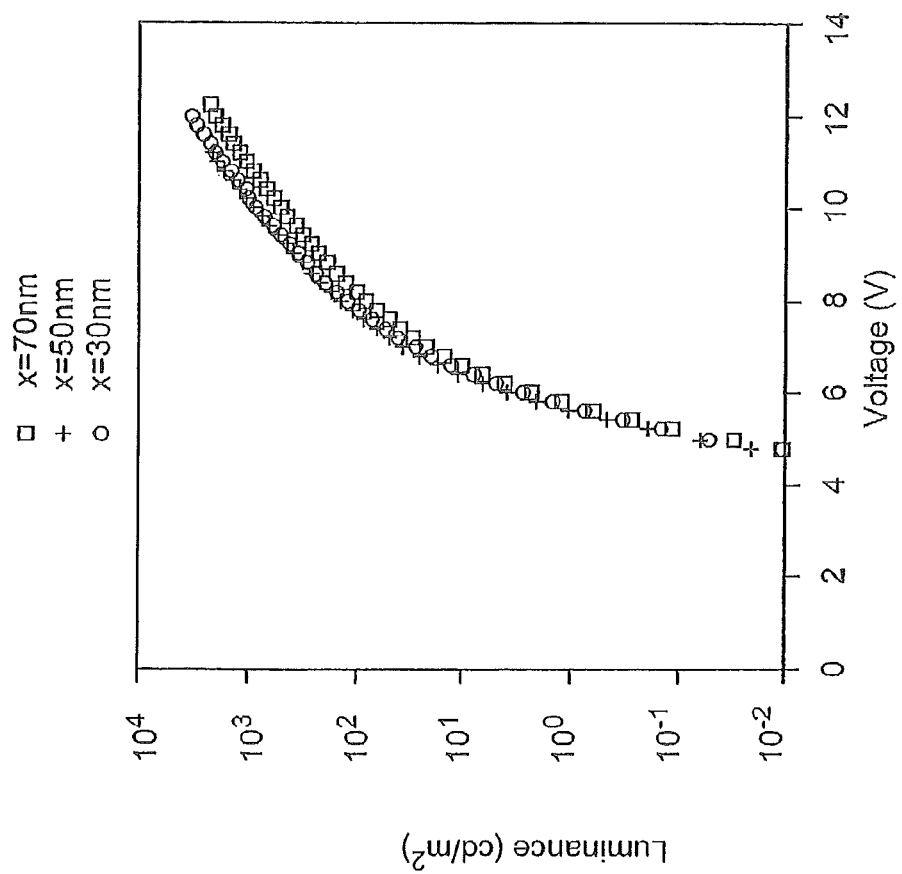
FIG. 30 is a graph of the luminance-voltage curve of three organic EL devices produced in Example 5.
Figure 31:
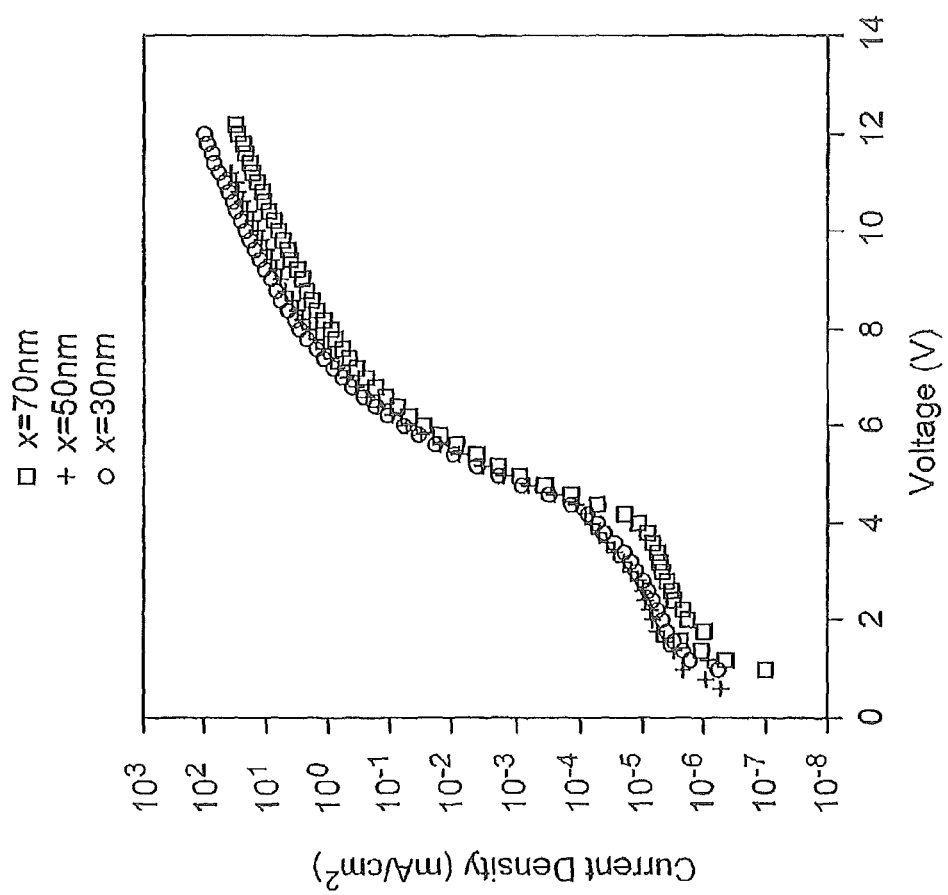
FIG. 31 is a graph of the current density-voltage curve of three EL devices produced in Example 5.
Figure 32:
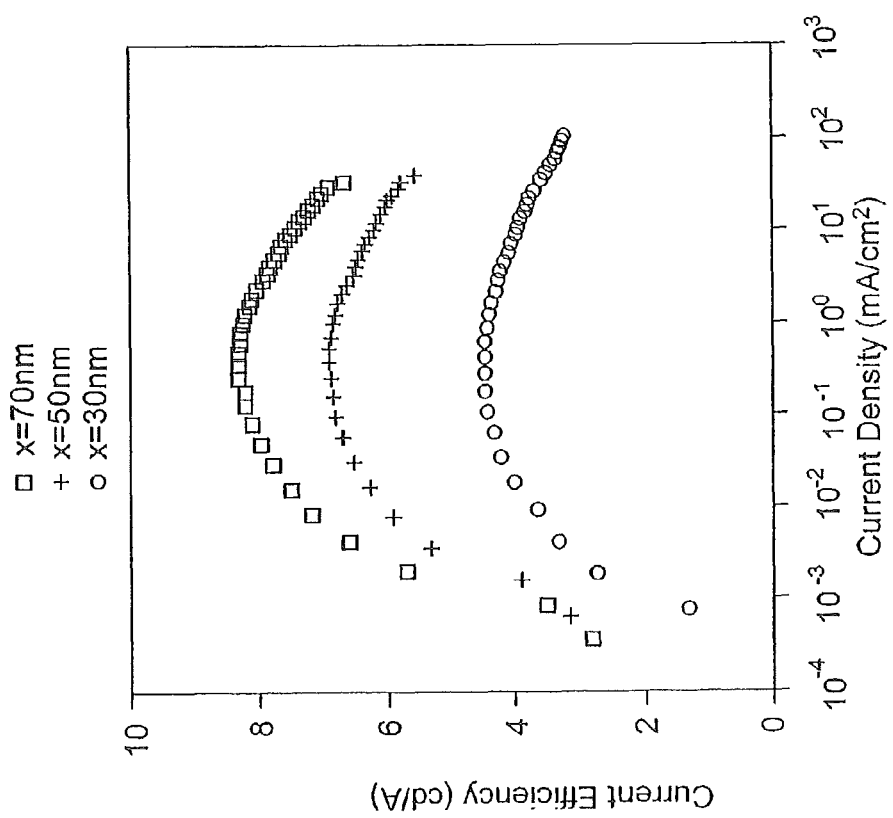
FIG. 32 is a graph of the current efficiency-current density curve of three. EL devices produced in Example 5.

In FIGS. 30, 31 and 32, the symbols □, + and ○ each represents a graph of the luminance ($cd/m^2$)—voltage (v) characteristic curve, a graph of the current density (mA/$cm^2$)—voltage (v) characteristic curve, and a graph of the current efficiency (cd/A)—current density (mA/cm) characteristic curve, respectively, of each of the EL devices having the three different thickness obtained in this example.

Figure 20:
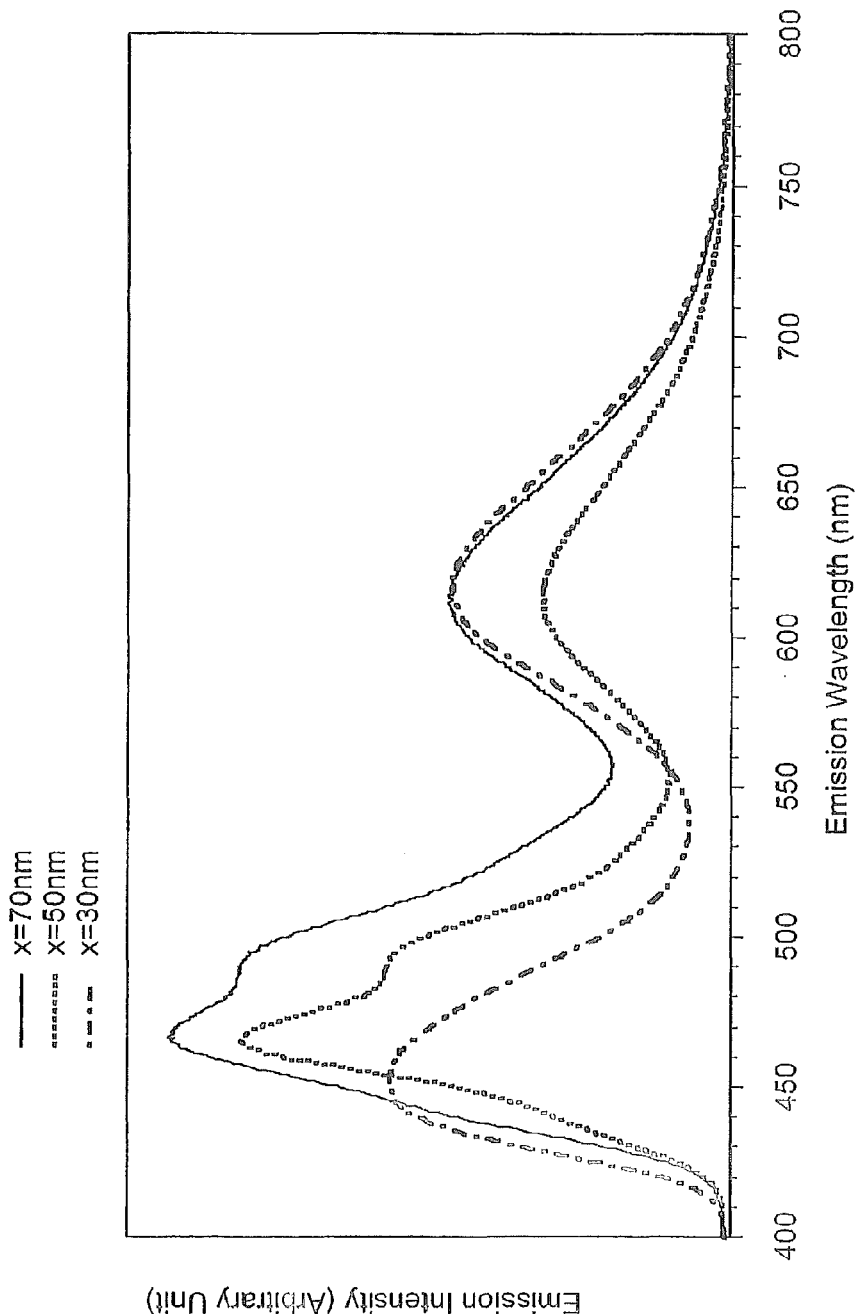
FIG. 20 is a graph of the emission spectrum of three EL devices produced in Example 5.

Furthermore, an emission spectrum of each of the three organic EL devices obtained in this example (Example 5) is shown in FIG. 20.

As shown in FIG. 32, the EL devices having the three different thicknesses each had a largely varied current efficiency (cd/A). In the devices including the light-emissive unit 3-2 having a thickness of about 700 Å in the hole transportation layer, a maximum current density exceeding about 8 cd/A was obtained, while in the devices including the light-emissive unit 3-2 having a thickness of about 300 or 500 Å in the hole transportation layer, the current density obtained was only about 6.5 or 4 cd/A.

The EL device including the light-emissive unit 3-2 having a thickness of about 700 Å had an optical path length (product of a real layer thickness and an index of refraction) from the light-emissive site of spiro-DPVBi (blue light-emissive material) to the Al cathode (light reflective electrode) of about three times a quarter wavelength of light. Namely, the EL device is an example of an optimized device.

Example 6

Figure 41:
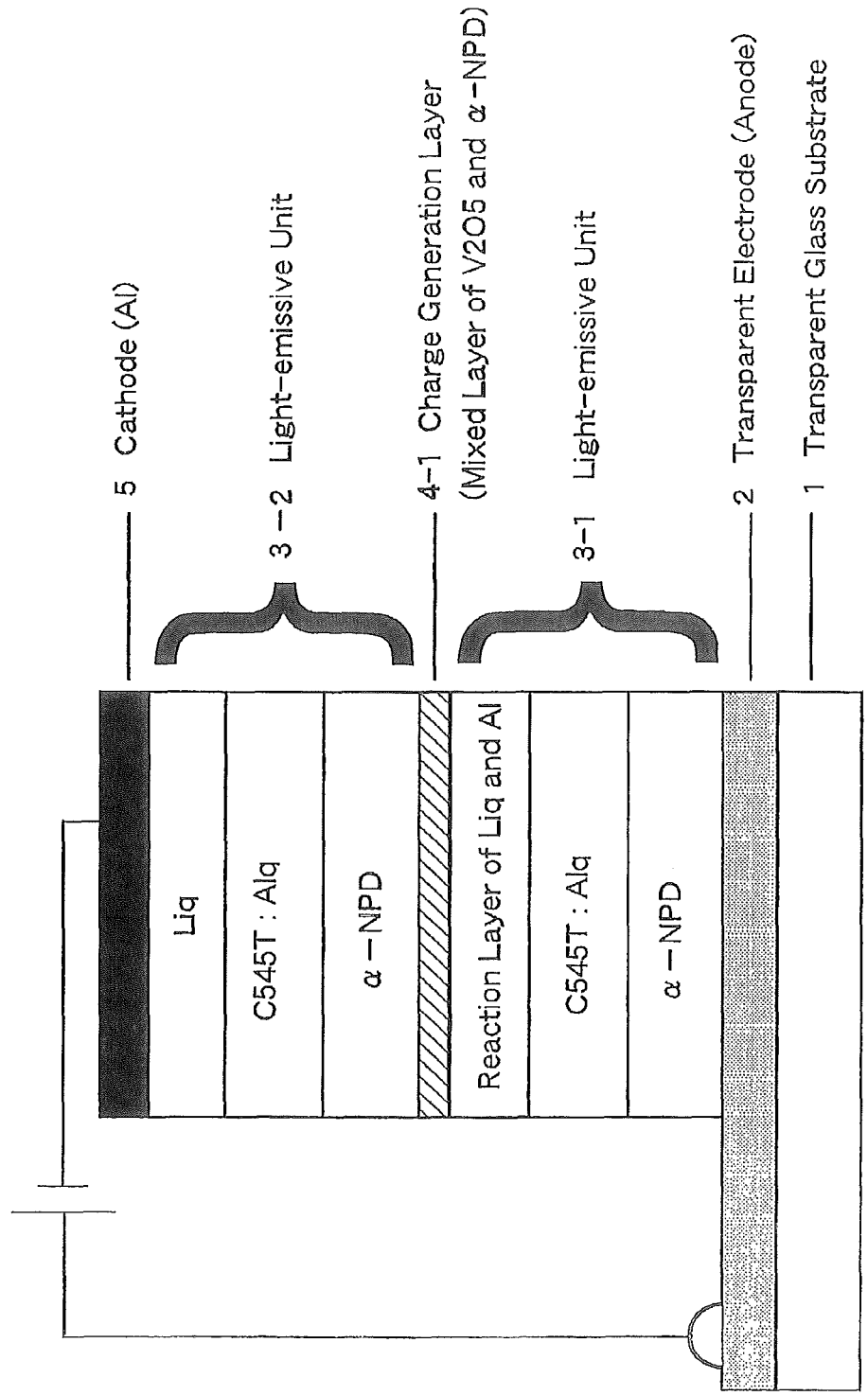
FIG. 41 is a schematic cross-sectional view illustrating a lamination structure of the organic EL device produced in Example 6.
Figure 42:
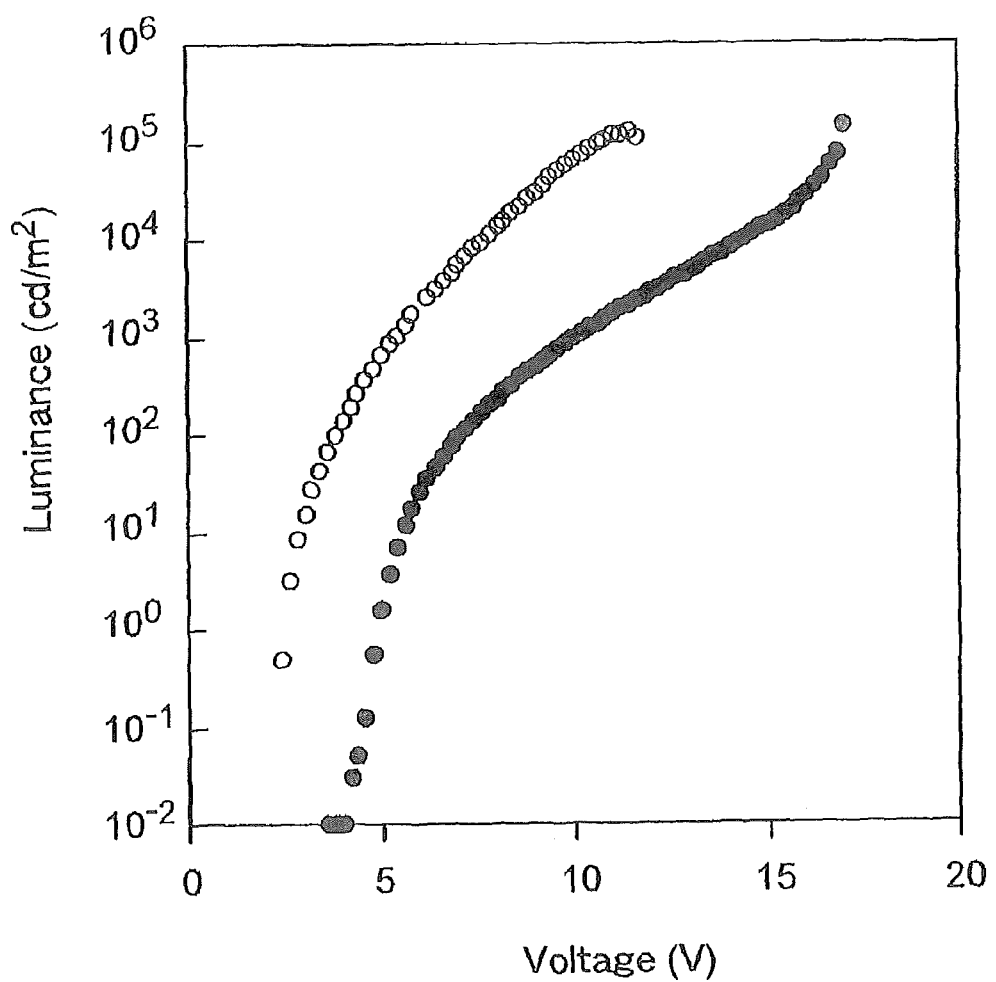
FIG. 42 is a graph of the luminance-voltage curve of the organic EL devices produced in Example 6 and a conventional device.
Figure 43:
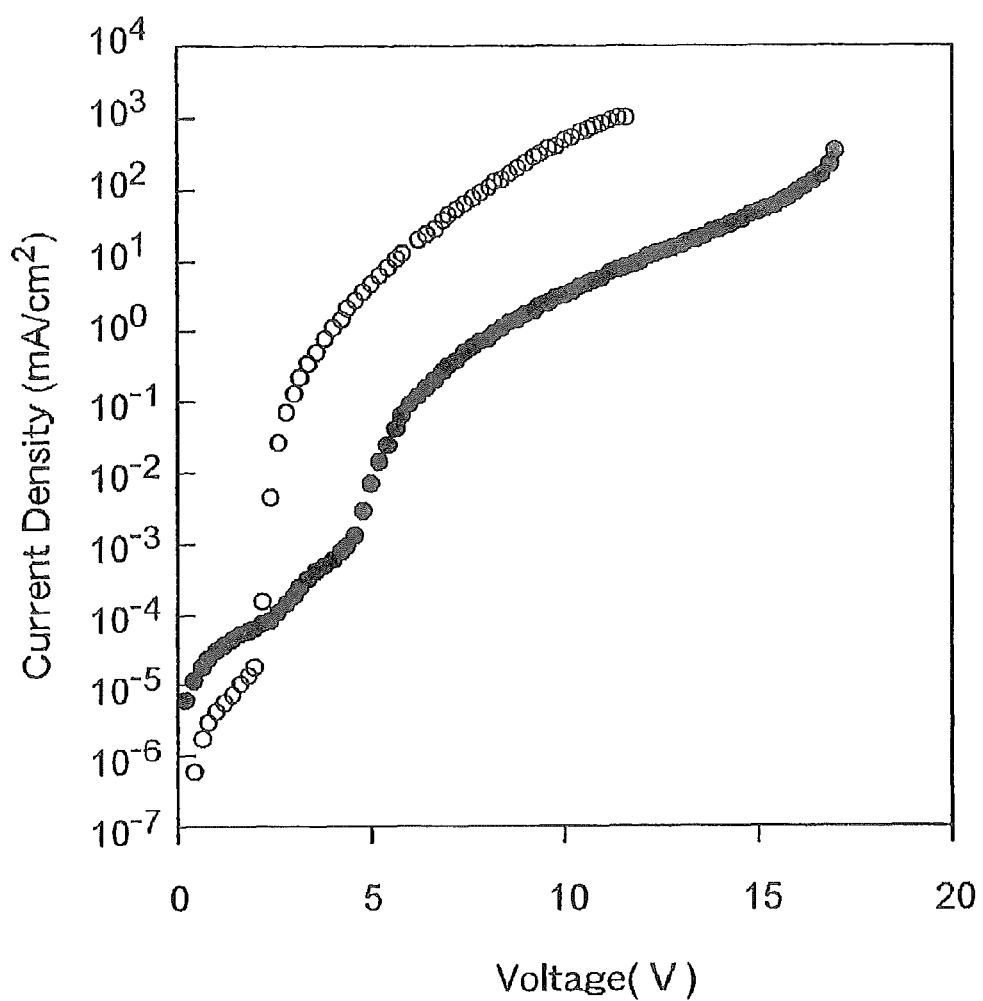
FIG. 43 is a graph of the current density-voltage curve of the EL devices produced in Example 6 and a conventional device.
Figure 44:
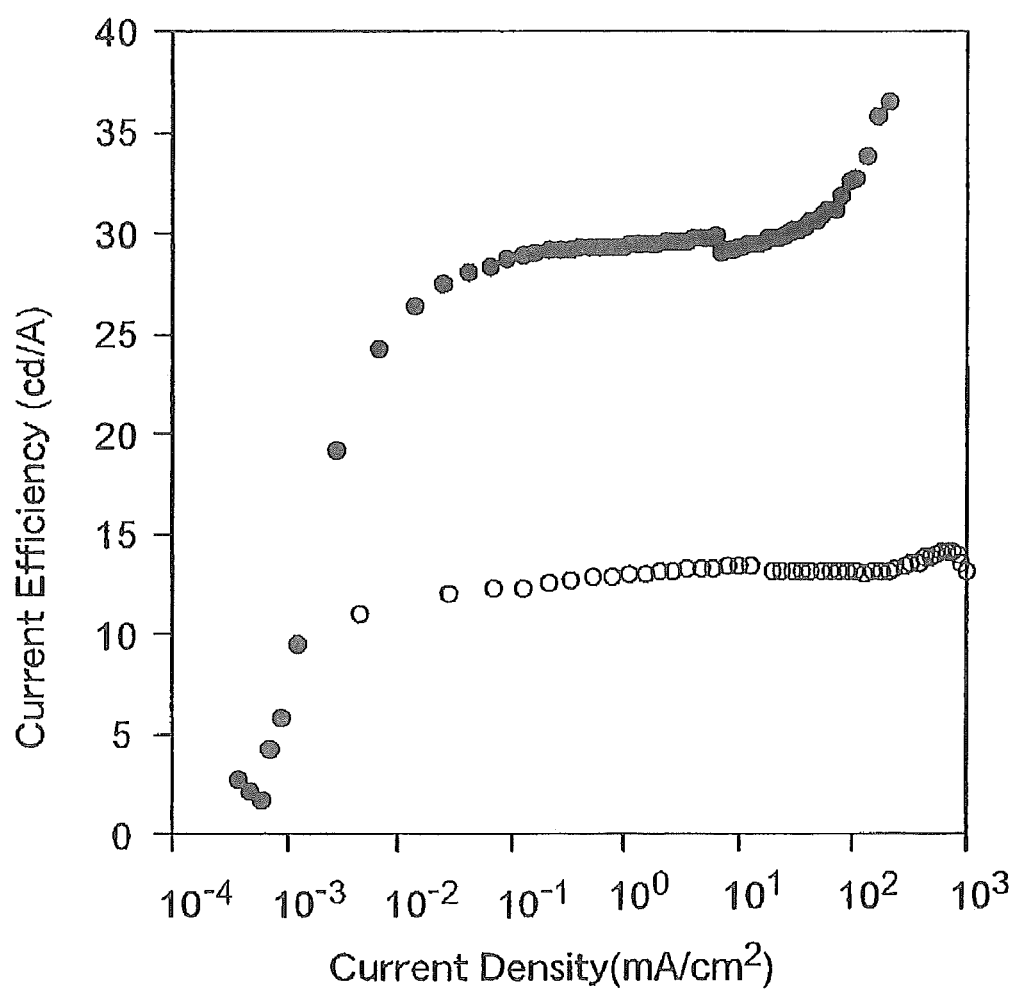
FIG. 44 is a graph of the current efficiency-current density curve of the EL devices produced in Example 6 and a conventional device.
Figure 45:
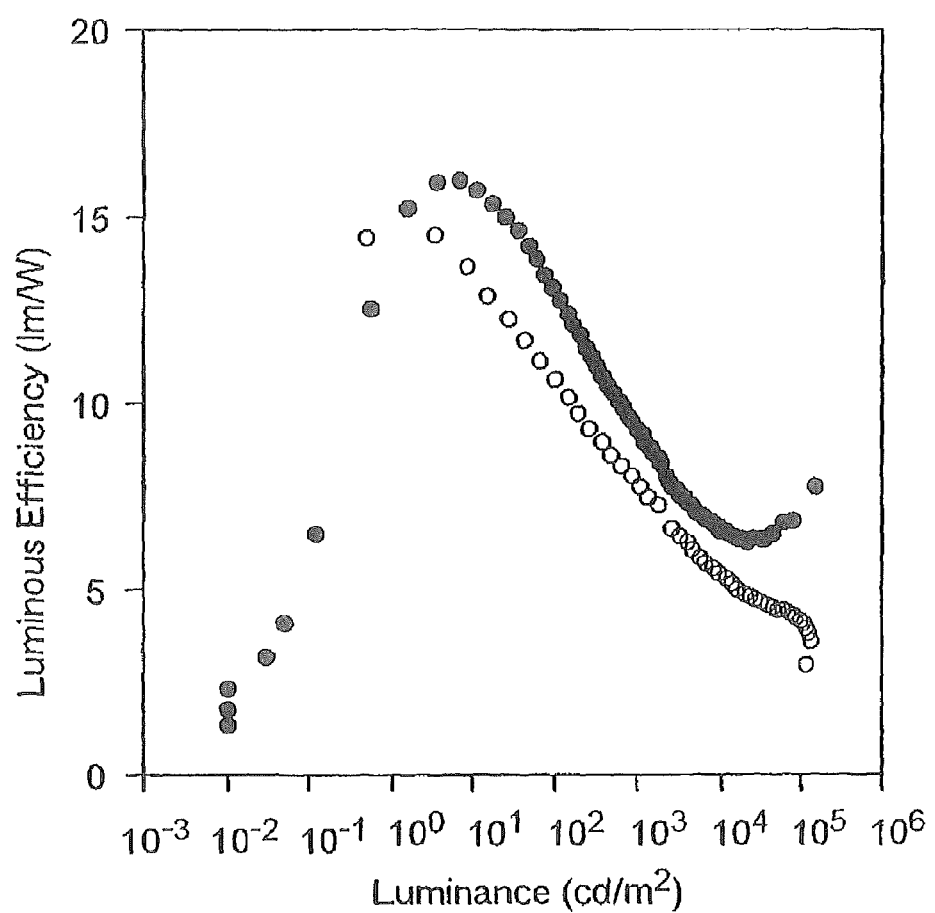
FIG. 45 is a graph of the luminous efficiency-luminance curve of the organic EL devices produced in Example 6 and a conventional device.

Example for the Production of the Organic EL Device in Which a Layer Contacting a Charge Generation Layer on an Anode Side is an In-Situ Reaction Generating Layer, and Having a Charge Generation Layer Consisting of the Mixture of $V_2O_5$ and Arylamine Compound The organic EL device according to the present invention having a laminate structure shown in FIG. 41 was produced as follows.

In accordance with the manner which is substantially the same as that described in Reference Example 1, a light-emissive unit 3-1 was deposited through a metal mask 40 for organic layer formation (see, FIG. 10B) on an ITO pattern-coated glass substrate 1 shown in FIG. 10A. Namely, a 600 Å-thick α-NPD and a 700 Å-thick layer including Alq:C545T=100:1 (weight ratio) were sequentially deposited. Thereafter the in-situ reaction generating layer was formed thereon.

Namely, a metal-organic complex of 8-quinolinolato lithium (hereinafter, briefly referred to as "Liq") represented by the following formula

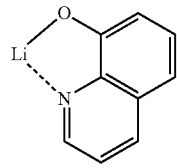

was deposited by 10 Å. Thereafter Al was deposited as a thermally reducible metal at a deposition rate of about 1 Å/sec to form an in-situ reaction generating layer having a thickness of 15 Å.

Subsequently, $V_2O_5$ (vanadium pentaoxide) and α-NPD was co-deposited at a molar ratio ($V_2O_5$:α-NPD=4:1) on the in-situ reaction generating layer at a deposition rate of 2 Å/sec to form the charge generation layer 4-1 having a thickness of 200 Å. The charge generation layer was also deposited via the metal mask 40 for organic layer formation (see, FIG. 10B).

Thereafter, while the metal mask 40 for organic layer formation (FIG. 10B) is still on the glass substrate 1, the above-described step was again repeated to form a light-emissive unit 3-2. Namely, a 600 Å-thick α-NPD, a 700 Å-thick layer including Alq:C545T=100:1 (weight ratio), and a 10 Å-thick Liq were sequentially deposited. Finally, aluminum (Al) was deposited through a metal mask 41 for cathode layer formation (see, FIG. 10C) at a deposition rate of 10 Å/sec to form a cathode electrode 5 having a thickness of about 1,000 Å. The organic EL device having a square light-emissive area of 0.2 cm (length) by 0.2 cm (width) was thus obtained (see, FIG. 10D).

In this organic EL device, a DC voltage was applied between the anode electrode (ITO) and the cathode electrode (Al), and the characteristics of the green light emitted from the light-emissive layer (co-deposited layer of Alq and C545T) were measured to obtain the results in FIGS. 42, 43, 44 and 45. In FIGS. 42, 43, 44 and 45, the circle symbols (●) represent a graph of luminance ($cd/m^2$)—voltage (v) characteristic curve, a graph of current density ($mA/cm^2$)—voltage (v) characteristic curve, a graph of current efficiency (cd/A)—current density ($mA/cm^2$) characteristic curve and a graph of luminous efficiency (lm/W)—luminance ($cd/m^2$) characteristic curve, respectively, of the EL device of Example 6.

For comparison, a result of a reference device (ITO/α-NPD, 600 Å/Alq:C545T=100:1, 700 Å/Liq, 10 Å/Al) having a conventional structure was plotted in FIGS. 42, 43, 44 and 45, using the circle symbols (○).

As shown in the drawings, in the organic EL device in which the light-emissive unit was partitioned into 2 units, a maximum current efficiency (and quantum efficiency) is improved to twice as the organic EL device in the above reference device.

In the EL device of Example 6, it is considered, like in Example 1, that a charge transfer complex ($V_2O_5^-$+α-$NPD^+$) was formed between molecules of the $V_2O_5$ and the α-NPD, a hole transporting arylamine molecule, by an oxidation reduction reaction. A mixed layer of the $V_2O_5$ and the α-NPD is functioned as the charge generation layer.

Furthermore, in this EL device, a material constituting the in-situ reaction generating layer includes only the organic metal complex having an alkaline metal ion (Lithium ion in the EXAMPLE 6). The material can be, however, a mixed layer of the electron transporting compound such as bathocuproine and Alq and the organic metal complex (see Japanese Laid-open Patent Application No. 2000-182774) or a layer including the organic metal complex containing one of said metal ion.

The in-situ reaction using inorganic compound containing one of said metal ion can also be adopted for the layer contacting the charge generation layer on an anode side, because such in-situ reaction has been observed conventionally also in using an inorganic alkaline metal compound as a contacting material to Al cathode and so on (see a reference document "J. Endo, T. Matsumoto, and J. Kido, Jpn. J. Appl. Phys. Vol. 41 (2002) pp. L800-L803").

Test Example

Measurement of Resistivity in the Charge Generation Layer and the Like

In this example, the resistivity (Ωcm) was measured with two different methods depending on the range of the resistivity of the test sample.

The first measuring method can be suitably applied to a test samples having a relatively large resistivity. The measurement is carried out by sandwiching a vapor deposition layer of the test sample with electrodes (see FIGS. 33 and 34). The resistivity of the test sample is then calculated from a ratio of the electric field E(V/cm), obtained from an applied voltage (V) and a layer thickness (cm) of the deposition layer of the sample, i.e., distance between the electrodes, and a current density ($A/cm^2$) obtained from an observed current value (A) and a cross-sectional area ($cm^2$) of the current flowing region, i.e., resistivity (Ωcm)=(V/cm)/($A/cm^2$).

Figure 33:
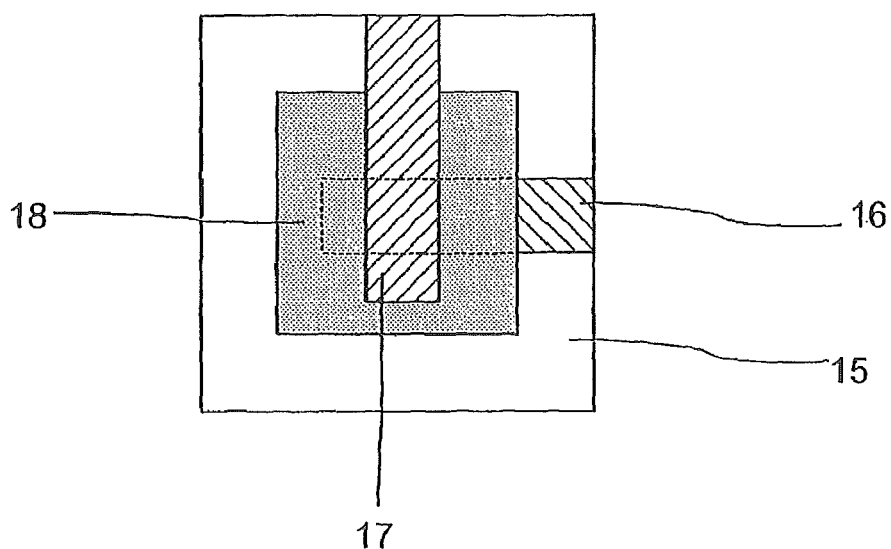
FIG. 33 is a plan view showing a device having a sandwiched structure used in the evaluation of the resistivity.
Figure 34:
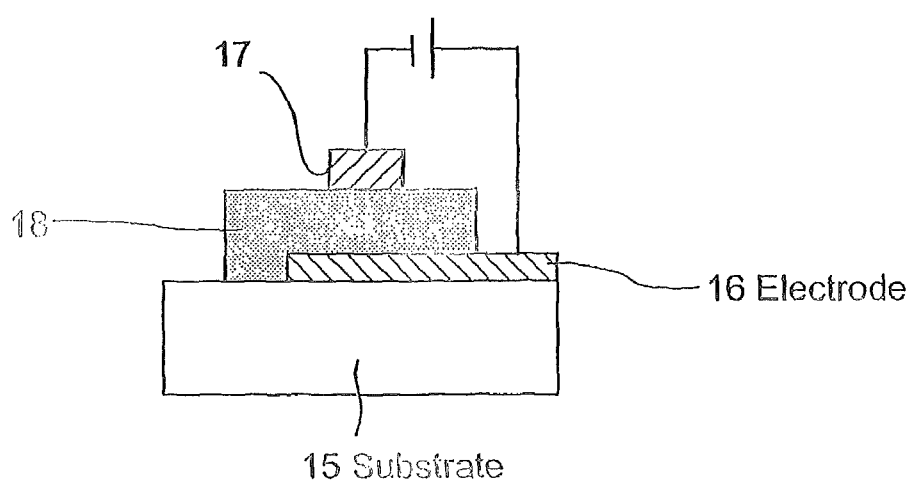
FIG. 34 is a cross-sectional view showing a device having a sandwiched structure used in the evaluation of the resistivity.

The resistivity evaluation device for use in this measuring method can be produced in accordance with the following method. FIG. 33 is a plan view of the evaluation device, and FIG. 34 is a cross-sectional view thereof.

As in the Examples and the Reference Examples described above, a metal mask 40 shown in FIG. 10B is used. A test sample (material, a resistivity of which is intended to be measured) 18 is deposited, through a shadow mask for forming both an organic layer and a charge generation layer, at a desired thickness on an ITO electrode 16 having a width of about 2 mm or, alternatively, an aluminum electrode having a width of about 2 mm. Finally, an aluminum electrode 17 having a width of about 2 mm is deposited in such a manner that it is crossed with the ITO electrode 16. A desired evaluation device is thus obtained.

Figure 35:
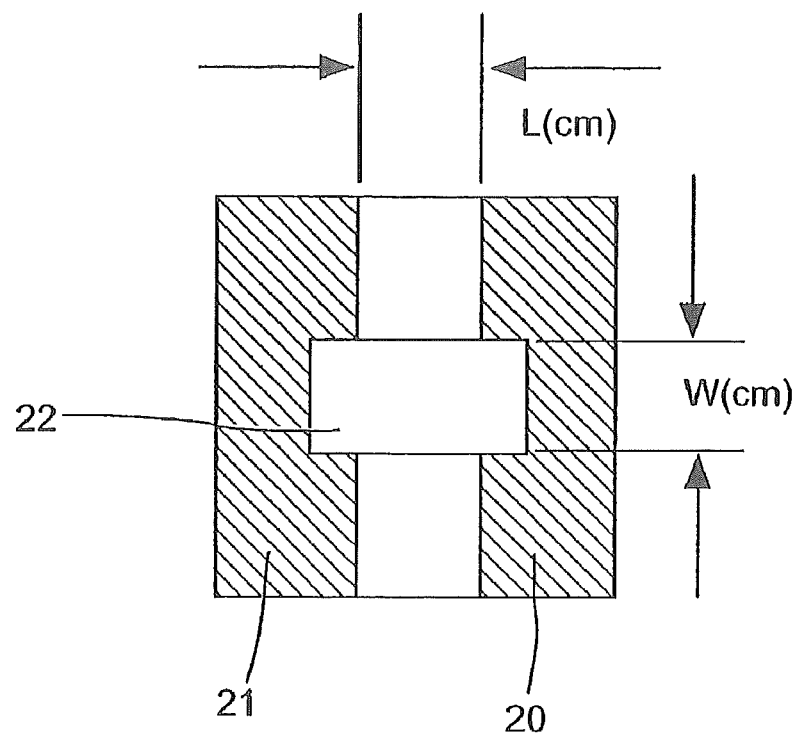
FIG. 35 is a plan view showing a device having a coplanar arrangement structure used in the evaluation of the resistivity.
Figure 36:
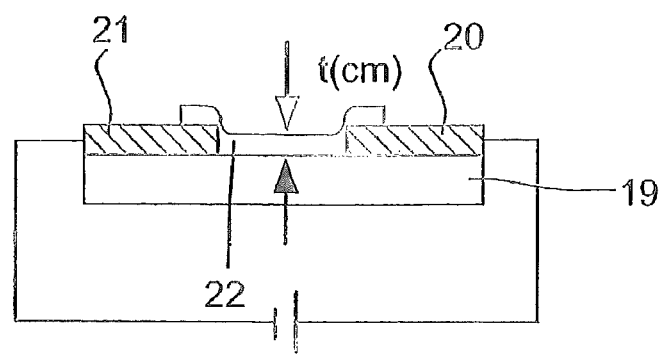
FIG. 36 is a cross-sectional view showing a device having a coplanar arrangement structure used in the evaluation of the resistivity.

The second measuring method can be suitably applied to the test samples having a relatively small resistivity. The measurement is carried out by using a resistivity evaluation device having a coplanar arrangement structure. Namely, as shown in FIGS. 35 and 36, a substrate 19 is provided, and on the same plane surface of the substrate 19, electrodes which are used as an anode 20 and a cathode 21 are previously deposited at a certain distance of L cm. A test material 22 is deposited through a metal mask for defining a deposition area having an opening with the certain width (W cm) on the electrodes-deposited substrate 19 to obtain a deposited layer having a desired thickness (t cm). In this measuring method, an electric field E(V/cm) of the test sample is calculated by dividing an applied voltage (V) with a distance (L cm) between the electrodes, and a current density (A/cm$^2$) is calculated by dividing an observed current value (A) by a cross-sectional area of the current flowing region (in this example, W×t cm$^2$). The resistivity (Ωcm) of the test sample can be calculated from the equation described above with regard to the first measuring method (sandwich method).

Figure 37:
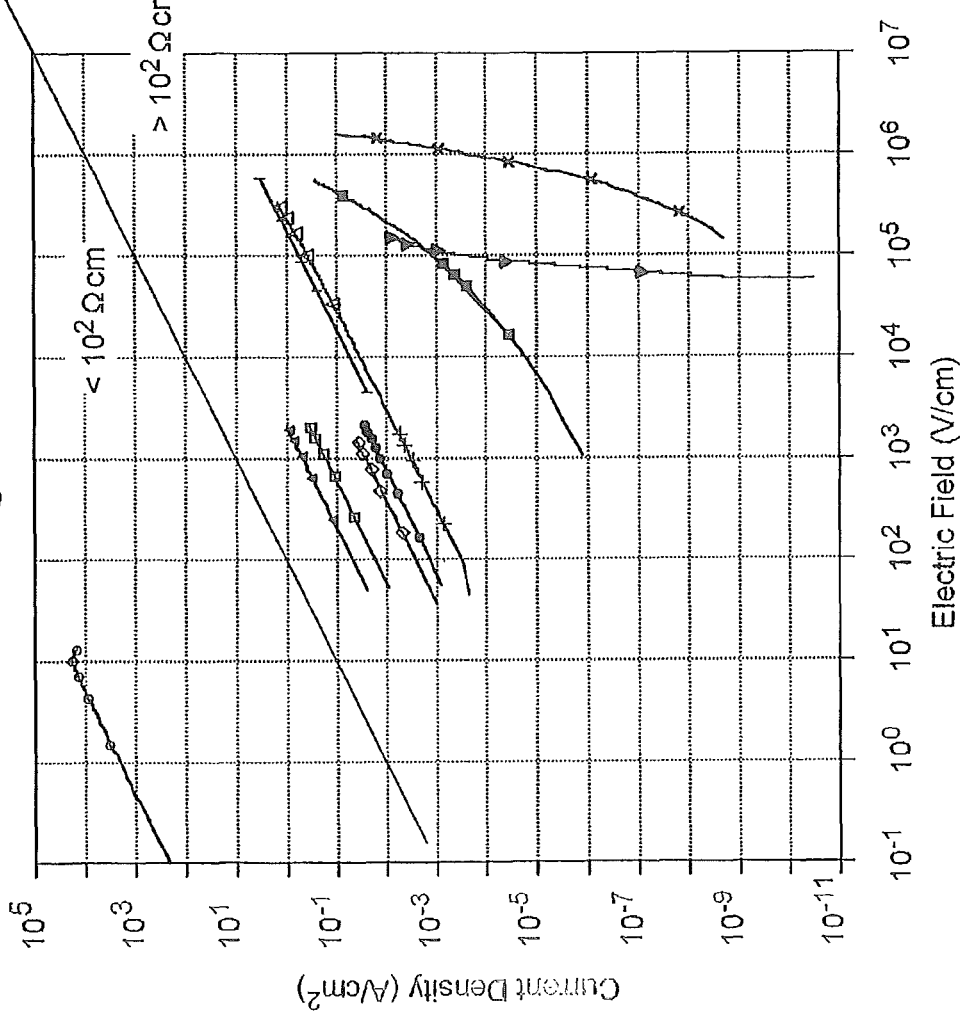
FIG. 37 is a graph of the electric field-current density curve for calculating a resistivity determined in a Test Example.
Figure 38A:
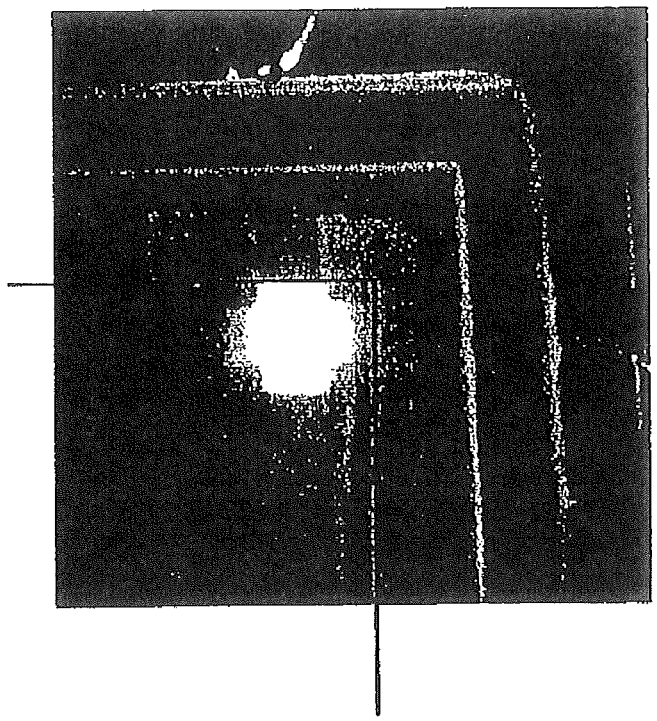
FIG. 38A is a photograph showing an emission state in the organic EL device described in Japanese Patent Application No. 2001-225847.
Figure 38B:
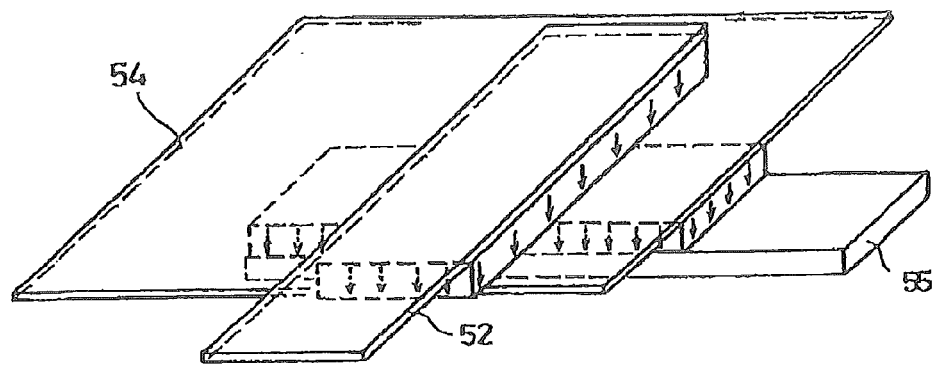
FIG. 38B is a schematic cross-sectional view illustrating a lamination structure of the organic EL device.

FIG. 37 is a graph showing the measurement results of the resistivity. The test samples used herein are ITO (transparent electrode material), $V_2O_5$ (a charge generation layer according to the present invention), a co-deposition layer of $V_2O_5$ and α-NPD (three kinds of molar ratios of $V_2O_5$:α-NPD=4:1, 1:1, 1:2) (a charge generation layer according to the present invention), a co-deposition layer of $V_2O_5$ and 2-TNATA [$V_2O_5$:2-TNATA=4:1 (molar ratio) (a charge generation layer according to the present invention)], a co-deposition layer of α-NPD, Cs and bathocuproine [Cs bathocuproine=1:1 (molar ratio) (electron injecting layer in the light-emissive unit)], and Alq (light emitting material).

For the ITO, the co-deposition layer of $V_2O_5$ and α-NPD, and the co-deposition layer of $V_2O_5$ and 2-TNATA, the resistivity was measured using a measuring device having a coplanar arrangement structure (coplanar arrangement method), and for the α-NPD, the co-deposition layer of Cs and bathocuproine, and Alq$_a$, the resistivity was measured using a measuring device having sandwich structure (sandwich method). Furthermore, the α-NPD having a thickness of 1000 Å was measured by a measuring device having the sandwich structure wherein the mixed layer of $V_2O_5$ and α-NPD (the composition of the charge generation layer according to the present invention) was formed thinly by 50 Å on a portion contacting both electrodes to make the charge injection from the electrode ohmic.

Furthermore, with regard to $V_2O_5$, the resistivity thereof was measured by using both of the coplanar arrangement method and the sandwich method with the result that a substantially same resistivity can be measured regardless of the difference of the applied methods.

Figure 40:
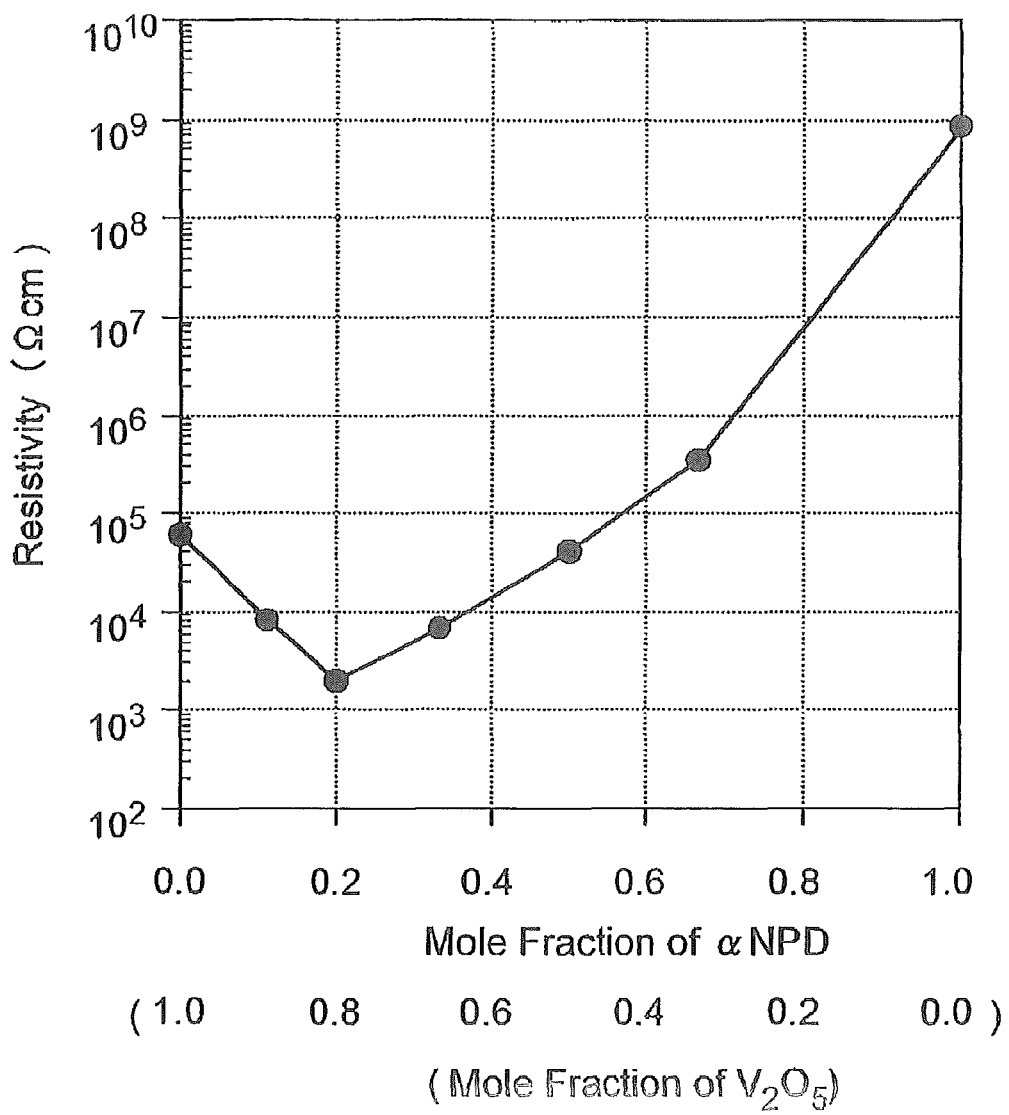
FIG. 40 is a graph showing a relation between mixed ratio (molar fraction) of the co-deposition layer of $V_2O_5$ and α-NPD, and resistivity.

Coplanar Arrangement Method:
○ ITO 4.6×10$^{-4}$ Ωcm
● $V_2O_5$ 7.2×10$^5$ Ωcm
▲ co-deposition layer of $V_2O_5$ and α-NPD ($V_2O_5$: α-NPD=4:1) 2.0×10$^3$ Ωcm
◇ co-deposition layer of $V_2O_5$ and α-NPD ($V_2O_5$:α-NPD=1:1) 3.6×10$^4$ Ωcm
+ co-deposition layer of $V_2O_5$ and α-NPD ($V_2O_5$: α-NPD=1:2) 2.9×10$^5$ Ωcm
□ co-deposition layer of $V_2O_5$ and 2-TNATA ($V_2O_5$:2-TNATA=4:1) 5.8×10$^3$ Ωcm Sandwich Method:
Δ ITO/$V_2O_5$/Al 2.8×10$^5$ Ωcm
▼ ITO/α-NPD/Al 1.5×10$^{13}$ Ωcm.
■ ITO/$V_2O_5$: α-NPD (50 Å)/α-NPD (1000 Å)/$V_2O_5$: α-NPD (50 Å)/Al 8.0×10$^8$ Ωcm
X Al/Alq$_3$/Al 6×10$^{13}$ Ωcm
| ITO/Cs:bathocuproine/Al 2×10$^5$ Ωcm FIG. 40 shows a relationship between a mixed ratio (molar fraction) of the co-deposition layer of $V_2O_5$ and α-NPD, and resistivity. As shown in FIG. 40, due to the mixing of both materials, the charge generation layer according to the present invention indicates a resistivity lower than that of each material. This result suggests a presence of oxidation reduction reaction caused by the transfer of electrons, i.e. formation of the charge transfer complex. Accordingly, it was found that the resistivity of the charge generation layer can be varied depending the way of contacting the electron accepting material such as $V_2O_5$ with the hole transporting material, using an appropriate method such as laminating or mixing.

As described above, since the EL device of the present invention has a structure wherein two or more light-emissive units were arranged between the electrodes while the light-emissive units are partitioned with an electrically insulating charge generation layer, an EL device having a long operational lifetime and a high luminance region can be achieved without increasing a current density so much. Furthermore, it is not necessary to frequently change and to precisely position shadow masks for defining a vapor deposition area during production, especially during the formation of two or more light-emissive units and a charge generation layer. Furthermore, in the production of simple matrix-type display devices, it is not required to perform an operation which may cause a risk of disconnection in formation of a cathode line, thus enabling to retain high productivity, and effectively and stably produce an organic EL device with a high luminance and long operational lifetime.

Moreover, when the EL device was applied to the production of an illumination apparatus, since a voltage reduction due to the resistance of the electrode material can be diminished, it becomes possible to achieve an uniform light emission over a large surface area. Similarly, if the EL device was applied to the production of a display device having a simple matrix structure, since a voltage reduction due to the wiring resistance and an increase of the substrate temperature can be largely diminished, it becomes possible to achieve a large surface area simple matrix display device which could not be obtained using the conventional EL devices.

Obvious changes may be made in the specific embodiments of the present invention described herein, such modifications being within the spirit and scope of the invention claimed. It is indicated that all matter contained herein is illustrative and does not limit the scope of the present invention.

What is claimed is:

1. An organic electroluminescent device-comprising a plurality of light-emissive units on a substrate, the plurality of light-emissive units provided between a cathode electrode and an anode electrode opposed to said cathode electrode, said plurality of light-emissive units comprising at least one light-emissive layer, wherein respective neighboring units of each of said light-emissive units is partitioned from each other by a charge generation layer wherein said charge generation layer comprises an electron accepting material and an electron donating material; and wherein each said light emissive layer in each said light-emissive unit is arranged to only emit light in an intersecting area between said cathode electrode and said anode electrode.

2. The organic electroluminescent device according to claim 1 wherein said charge generation layer comprises a mixed layer formed from different materials, one component of said charge generating material being a metal oxide, and
wherein said metal oxide forms a charge transfer complex upon an oxidation-reduction reaction.

3. The organic electroluminescent device according to claim 1, wherein one component included in said charge generation layer is
an organic compound having an ionization potential of less than 5.7 eV.

4. The organic electroluminescent device according to claim 3, wherein said organic compound included in said charge generation layer comprises an arylamine compound, wherein said arylamine compound is represented by the following formula (1):

wherein Ar1, Ar2 and Ar3 each independently represents an aromatic hydrocarbon group which may have substituents.

5. The organic electroluminescent device according to claim 4, wherein said arylamine compound included in said charge generation layer has a glass transition temperature of not lower than 90° C.

6. The organic electroluminescent device according to claim 1, wherein one layer included in said charge generation layer comprises a metal oxide.

7. The organic electroluminescent device according to claim 6, wherein said metal oxide comprises one of vanadium pentaoxide and rhenium heptaoxide.

8. The organic electroluminescent device according to claim 1, wherein said charge generation layer comprises an insulating layer.

9. The organic electroluminescent device according to claim 8, wherein the charge generation layer constitutes an electrically insulating layer having a resistivity of not less than $1.0 \times 10^5$ Ωcm.

10. The organic electroluminescent device according to claim 1, wherein even if a short-circuiting due to a pin-hole in a charge generation layer occurs, said organic electroluminescent device is arranged to emit light in said light-emissive units other than a light emissive unit which has the charge generation layer including the pin-hole.

11. The organic electroluminescent device according to claim 1, wherein one layer included in said charge generation layer has metal halide which is said electron accepting/material.

12. The organic electroluminescent device according to claim 1, wherein one layer included in said charge generation layer comprises an electron accepting organic compound which constitutes said electron accepting material.

13. The organic electroluminescent device according to claim 12, wherein said electron accepting organic compound included in said charge generation layer comprises at least one fluorine as a substituent group.

14. The organic electroluminescent device according to claim 13, wherein said electron accepting organic compound included in said charge generation layer comprises at least one cyano group as a substituent group.

15. The organic electroluminescent device according to claim 1, wherein said light-emissive unit includes, as a layer in contact with said charge generation layer on an anode side thereof, an electron injection layer formed from a mixed layer including an organic compound and a metal electron donating dopant.

16. The organic electroluminescent device according to claim 15, wherein said electron donating dopant comprises a metal selected from a group including an alkaline metal, an alkaline earth metal and a rare earth metal.

17. The organic electroluminescent device according to claim 1, wherein said light-emissive unit comprises, as a layer in contact with said charge generation layer on an anode side thereof, a metal layer having a thickness of not more than 5 nm formed from a metal selected from an alkaline metal, an alkaline earth metal and a rare earth metal,
wherein said metal layer diffuses in an electron accepting organic compound provided in the adjacent electron transporting layer, which has an electron accepting property, to react with said electron accepting organic compound, and
wherein an electron injection layer, formed from a mixed layer of a metal functioning as an electron donating dopant and said electron accepting organic compound, is formed as a result of said diffusion.

18. The organic electroluminescent device according to claim 1, wherein said light-emissive unit comprises a structure, as a layer in contact with said charge generation layer on an anode side thereof, in which an electron injection layer formed from a mixed layer of an organic compound and a metal functioning as an electron donating dopant is formed, and thereafter, a reaction generating layer is generated by an in-situ reduction reaction when a thermally reducible metal, which can reduce an alkaline metal ion, an alkaline earth metal ion or a rare earth metal ion to a metal in a vacuum, is deposited on an organic metal complex compound containing at least one metal ion selected from an alkaline metal ion, an alkaline earth metal ion and a rare earth metal ion.

19. The organic electroluminescent device according to claim 1, wherein said light-emissive unit comprises a structure, as a layer in contact with said charge generation layer on an anode side thereof, in which an electron injection layer of an organic compound and metal functioning as an electron donating dopant is formed, and thereafter, a reaction generating layer is generated by an in-situ reduction reaction when a thermally reducible metal, which can reduce an alkaline metal ion, an alkaline earth metal ion or a rare earth metal ion to a metal in a vacuum, is deposited on an inorganic compound containing at least one metal ion selected from an alkaline metal ion, an alkaline earth metal ion and a rare earth metal ion.

20. The organic electroluminescent device according to claim 1, wherein said light-emissive unit comprises, as a layer in contact with said charge generation layer on a cathode side thereof, a hole injection layer including a mixture of an organic compound and an electron accepting compound having a property capable of oxidizing said organic compound in terms of Lewis acid chemistry.

* * * * *